(12) United States Patent
Wang et al.

(10) Patent No.: US 10,058,572 B2
(45) Date of Patent: Aug. 28, 2018

(54) PLACENTA-DERIVED MULTIPOTENT STEM CELLS

(71) Applicant: The Regents of the University of California, Oakland, CA (US)

(72) Inventors: Aijun Wang, Davis, CA (US); Diana L. Farmer, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/912,066

(22) PCT Filed: Aug. 14, 2014

(86) PCT No.: PCT/US2014/051155
§ 371 (c)(1),
(2) Date: Feb. 12, 2016

(87) PCT Pub. No.: WO2015/023901
PCT Pub. Date: Feb. 19, 2015

(65) Prior Publication Data
US 2016/0184365 A1  Jun. 30, 2016

Related U.S. Application Data

(60) Provisional application No. 61/866,524, filed on Aug. 15, 2013, provisional application No. 61/982,804, filed on Apr. 22, 2014.

(51) Int. Cl.
| | | |
|---|---|---|
| *A61K 35/50* | (2015.01) | |
| *A61K 35/28* | (2015.01) | |
| *C12N 5/073* | (2010.01) | |
| *C12N 5/0775* | (2010.01) | |
| *A61K 9/00* | (2006.01) | |
| *A61K 9/06* | (2006.01) | |

(52) U.S. Cl.
CPC ............. *A61K 35/28* (2013.01); *A61K 35/50* (2013.01); *C12N 5/0605* (2013.01); *C12N 5/0668* (2013.01); *A61K 9/0085* (2013.01); *A61K 9/06* (2013.01)

(58) Field of Classification Search
CPC ................................ A61K 35/50; A61K 35/28
See application file for complete search history.

(56) References Cited

U.S. PATENT DOCUMENTS

| | | | | |
|---|---|---|---|---|
| 2005/0058631 | A1* | 3/2005 | Kihm .................. | C12N 5/0607 424/93.7 |
| 2005/0124003 | A1 | 6/2005 | Atala et al. | |
| 2006/0014287 | A1 | 1/2006 | Sherwood et al. | |
| 2012/0269786 | A1 | 10/2012 | Woods et al. | |

FOREIGN PATENT DOCUMENTS

| | | |
|---|---|---|
| WO | WO-2013/028625 A1 | 2/2013 |
| WO | WO-2013/067038 A1 | 5/2013 |

OTHER PUBLICATIONS

Hollis et al, "Neurotrophins: Potential Therapeutic Tools for the Treatment of Spinal Cord Injury" Neurotherapeutics, 2011, vol. 8, pp. 694-703.*
International Search Report and Written Opinion (ISA/US) for International Application No. PCT/US2014/051155, dated Dec. 18, 2014.
Zavan, et al., "Neural potential of a stem cell population in the adipose and cutaneous tissues," Neurological Research, A journal of Progress in Neurosurgery, Neurology and Neuro Sciences, published online: Jul. 19, 2013.
Bacenkova, D. et al. (2011) "Isolation and basic characterization of human term amnion and chorion mesenchymal stromal cells," Cytotherapy 13:1047-1056.
Barlow, S. et al. (2008) "Comparison of Human Placenta- and Bone Marrow-Derived Multipotent Mesenchymal Stem Cells," Stem Cells and Development 17:1095-1108.
Calzarossa, C. et al. (2013) "Neurorescue Effects and Stem Properties of Chorionic Villi and Amniotic Progenitor Cells," Neuroscience 234:158-172.
Farmer, D.L. et al. (2003) "In Utero Repair of Myelomeningocele," Arch Surg. 138:872-878.
Fauza, D.O. et al. (2008) "Neural stem cell delivery to the spinal cord in an ovine model of fetal surgery for spina bifida," Surgery 144:367-373.
Fichter, M.A. et al. (2008) "Fetal Spina Bifida Repair—Current Trends and Prospects of Intrauterine Neurosurgery," Fetal Diag Ther. 23:271-283.
Guillot, P.V. et al. (2007) "Human First-Trimester Fetal MSC Express Pluripotency Markers and Grow Faster and Have Longer Telomeres Than Adult MSC," Stem Cells 25:646-654.
Hass, R. et al. (2011) "Different populations and sources of human mesenchymal stem cells (MSC): A comparison of adult and neonatal tissue-derived MSC," Cell Communication and Signaling 9:12, 14 pgs.
Lee, J.M. et al. (2012) "Comparison of immunomodulatory effects of placenta mesenchymal stem cells with bone marrow and adipose mesenchymal stem cells," International Immunopharmacology 13:219-224.

(Continued)

*Primary Examiner* — Allison M Fox
(74) *Attorney, Agent, or Firm* — Foley & Lardner LLP; Antoinette F. Konski; Peng Sun

(57) ABSTRACT

This disclosure provides isolated cells and compositions comprising one or more isolated cell(s) as described herein. In one aspect, the isolated cell is a pre-term placenta-derived stem cell (also referred to placenta-derived multi potent stem cells (pmSCs). As used herein, the term "pre-term placenta-derived multipotent stem cell or placenta-derived stem cells" intends a cell isolated from placental tissue prior to delivery of the fetus by surgery or birth. In another aspect, the isolated cell is a chorionic villus (CV)-derived multipotent placental stem cells (C-mpSCs). Also provided are compositions comprising these cells, wherein the composition comprises an effective amount of the isolated cells as described herein.

13 Claims, 25 Drawing Sheets

(56) References Cited

OTHER PUBLICATIONS

Liang, X. et al. (2014) "Paracrine Mechanisms of Mesenchymal Stem Cell-Based Therapy: Current Status and Perspectives," Cell Transplantation 23:1045-1059.

Martinez, A.M.B. et al. (2014) "Neurotrauma and mesenchymal stem cells treatment: From experimental studies to clinical trials," World J Stem Cells 6(2):179-194.

Murphy, S.V. et al. (2013) "Amniotic Fluid and Placental Membranes: Unexpected Sources of Highly Multipotent Cells," Semin Reprod Med. 31:62-68.

Portmann-Lanz, C.B. et al. (2006) "Placental mesenchymal stem cells as potential autologous graft for pre- and perinatal neuroregeneration," American Journal of Obstetrics and Gynecology 194:664-673.

Quertainmont, R. et al. (2012) "Mesenchymal Stem Cell Graft Improves Recovery after Spinal Cord Injury in Adult Rats through Neurotrophic and Pro-Angiogenic Actions," PLoS ONE 7(6):e39500, 15 pgs.

Saadai, P. et al. (2011) "Fetal neurosurgery: current state of the art," Future Neurol. 6(2):165-171.

Uccelli, A. et al. (2011) "Neuroprotective features of mesenchymal stem cells," Best Practice & Research Clinical Haematology 24:59-64.

Vellasamy, S. et al. (2012) "Isolation and characterisation of mesenchymal stem cells derived from human placenta tissue," World J Stem Cells 4(6):53-61.

\* cited by examiner

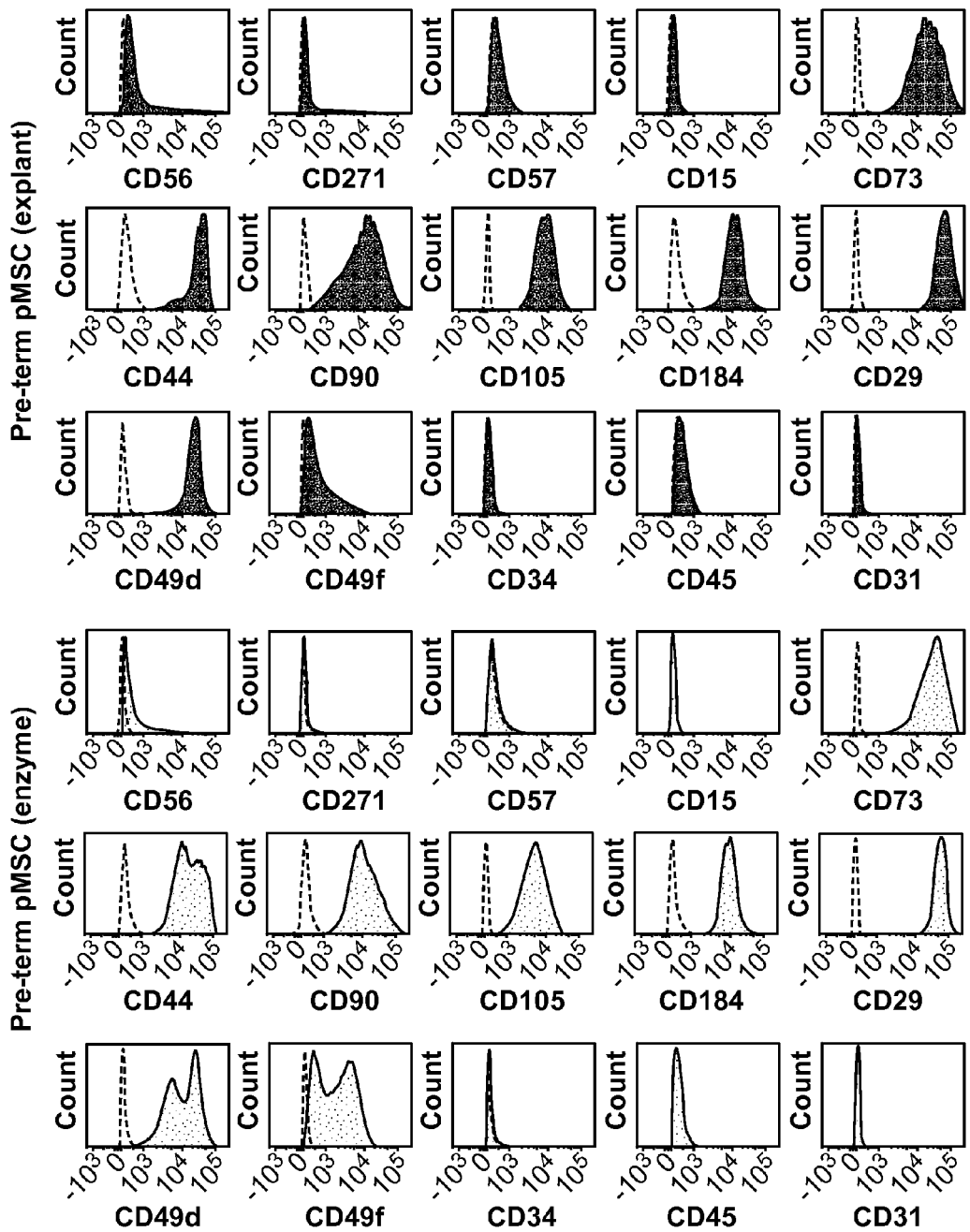
FIG. 6 (Cont. 1)

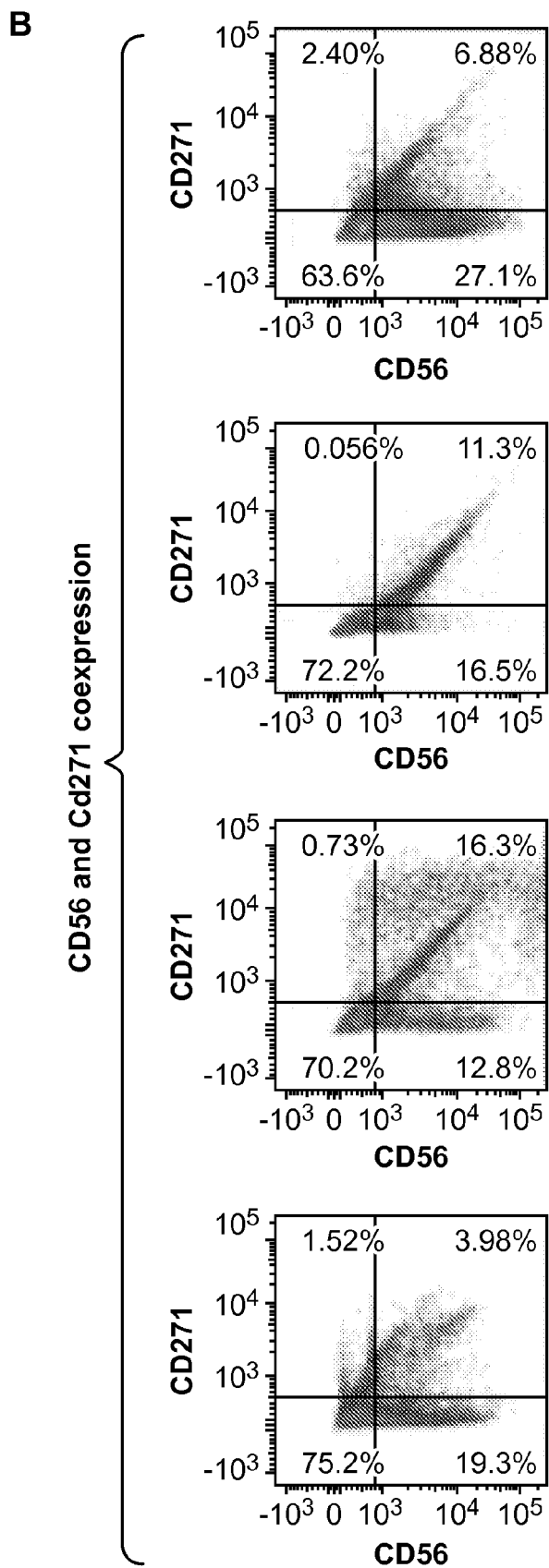
FIG. 6 (Cont. 2)

A

Bone Marrow MSCs    Term pMSCs    Pre-Term pMSCs

Schwann: S100β, GFAP, S100β, GFAP, S100β, GFAP
Neuron: NFM, TUJ1, NFM, TUJ1, NFM, TUJ1

B

Bone Marrow MSCs    Term pMSCs    Pre-Term pMSCs

Osteo: ALP, Alizarin Red, ALP, Alizarin Red, ALP, Alizarin Red
Adipo: Phase, Oil Red, Phase, Oil Red, Phase, Oil Red
Chondro: Collagen II, Alcian Blue, Collagen II, Alcian Blue, Collagen II, Alcian Blue

| LIMB MOVEMENT | | | | | STANCE WITH HELP/ ASSISTANCE | | LOCOMOTION | | |
|---|---|---|---|---|---|---|---|---|---|
| HINDLIMB | | | | | | | STEPPING Total# | | FORLIMB-HINDLIMB COORDINATION |
| Hip | | Knee | | Ankle | Total Score | No | Yes | HINDLIMB | None / Occasional / Frequent |
| L | R | L | R | L | R | | | | |
| 0 | 0 | 0 | 0 | 0 | 0 | | SPONTANEOUS Hindlimb weight support | 0 | |
| S | S | S | S | S | S | No | Yes L R | 1-4 | occ<50% freq>50% |
| E | E | E | E | E | E | | SPONTANEOUS Standing | >5 | CLEARANCE TEST |
| 0=none  S=slight  E=extensive | | | | | | No | Yes | | Fail |
| 0=0 points  S=1 point  E=2 points | | | | | | | | | Pass |

B

| | |
|---|---|
| SEVERE | Grade 0: complete paraplegia, no movement of any joints |
| | Grade 1: total of 1-3 points for joint movement |
| | Grade 2: total of 4-6 points for joint movement |
| | Grade 3: total of 7-9 points for joint movement |
| | Grade 4: total of 10-12 points for joint movement |
| MODERATE | Grade 5: capable of stance with help, ≥4 joints with slight movement |
| | Grade 6: capable of stance with help, ≥4 joints with extensive movement |
| | Grade 7: capable of spontaneous hindlimb weight support, ≥4 joints with slight movement |
| | Grade 8: capable of spontaneous hindlimb weight support, ≥4 joints with extensive movement 0 |
| | Grade 9: capable of stance with help, capable of 1-4 steps |
| MILD | Grade 10: capable of stance with help, capable of ≥5 steps with no or occasional forelimb-hindlimb coordination |
| | Grade 11: capable of stance with help, capable of ≥5 steps with frequent forelimb-hindlimb coordination |
| | Grade 12: capable of standing up spontaneously on hindlimbs, capable of 0-4 steps |
| | Grade 13: capable of standing up spontaneously on hindlimbs, capable of ≥5 steps with no or occasional forelimb-hindlimb coordination |
| | Grade 14: capable of standing up spontaneously on hindlimbs, capable of ≥5 steps with frequent forelimb-hindlimb coordination, not able to pass hindlimb clearance test |
| NORMAL | Grade 15: capable of standing up spontaneously on hindlimbs, capable of ≥5 steps with frequent forelimb-hindlimb coordination, able to pass hindlimb clearance test |

FIG. 18

PLACENTA-DERIVED MULTIPOTENT STEM CELLS

CROSS-REFERENCE TO RELATED APPLICATIONS

This application is a national stage application under 35 U.S.C. § 371 of International Application No. PCT/US2014/05115, filed Aug. 14, 2014, which claims priority under 35 U.S.C. § 119(e) to U.S. Provisional Application Nos. 61/866,524 and 61/982,804, filed Aug. 15, 2013 and Apr. 22, 2014, respectively, the content of each of which is incorporated herein by reference in its entirety.

BACKGROUND

Spinal cord injury (SCI) is a devastating trauma which results in functional impairments varying from motor and sensory dysfunction to irreversible paralysis (Sahni, V. et al. (2010) Nature Reviews Neurology 6:363-372). 1,275,000 Americans suffer from some form of SCI (Paralysis Facts & FIGS. 2010) The Christopher and Dana Reeve Foundation Paralysis Resource Center) and, depending on the severity of injury and age at injury, lifetime healthcare costs associated with that injury may exceed 4.5 million dollars (Spinal Cord Injury Facts and Figures at a Glance (2012) J. Spinal Cord Med. 35:480-481). Stem cell therapy for SCI with a variety of cell sources has been investigated in numerous preclinical and a few clinical trials (Reier, P. J. (2004) NeuroRx: The Journal of the American Society for Experimental NeuroTherapeutics 1:424-451). Despite promising findings in predominantly rodent models (Lu, P. et al. (2012) Cell 150:1264-1273; Busch, S. A. et al. (2011) The Journal of Neuroscience: the Official Journal of the Society for Neuroscience 31:944-953; Parr, A. M. et al. (2007) Bone Marrow Transplantation 40:609-619), clinical trials have not yet substantiated the clinical utility of these stem cell therapies. This discrepancy has in part been linked to differences between rodent and higher order mammalian spinal cords, and differences in the severity or mechanism of SCI (Sahni, V. et al. (2010) Nature Reviews Neurology 6:363-372). As discussed below, Applicants' research on a congenital form of SCI is providing critical leads in the search for a clinically relevant, stem cell based therapy or cure for SCI.

Myelomeningocele (MMC), a form of spina bifida (SB), is a devastating birth defect caused by incomplete closure of the neural tube during development. Intrauterine damage to the exposed spinal cord leaves afflicted children with lifelong paralysis, fecal and urinary incontinence, musculoskeletal deformities and cognitive disabilities. Healthcare costs for children with MMC are 13 times greater than those for children without MMC. Even as adults, individuals born with MMC shoulder almost 7 times the medical expenses of peers with no history of MMC (Ouyang, L. et al. (2007) Birth Defects Research Part A: Clinical and Molecular Teratology. 79:552-558). In the US alone, approximately 4 children a day are born with this personally and financially costly disease (Parker, S. E. et al. (2010) Birth Defects Res. A Clin. Mol. Teratol. 88(12):1008-1016). The recent Management of Myelomeningocele Study (MOMS) randomized-controlled clinical trial demonstrated that in utero coverage of the spinal cord improves the paralysis of some MMC patients compared to postnatal repair (Adzick, N. S. et al. (2011) N. Engl. J. Med. 364:993-1004). While promising, these improvements were limited and sporadic. Covering the spinal cord may prevent further in utero damage, but simple closure fails to reverse injury incurred prior to repair. In utero stem cell therapy can build upon this surgical advance to cure MMC. The fetal environment contains numerous qualities which can facilitate stem cell therapy. (Tiblad, E. et al. (2008) Best Pract. Res Clin. Obstet. Gynaecol. 22(1):189-201; Flake, A. W. (2004) Best Pract. Res Clin. Obstet. Gynaecol. 18:941-958) Chief among them, the natural receptivity of the gestational environment to remodeling and regeneration of fetal tissues by stem cells. While a diverse array of autologous and allogeneic cells have been investigated for in utero therapy (Flake, A. W. et al. (1999) Blood 94:2179-2191; Roybal, J. L. et al. (2010) Semin. Fetal Neonatal. Med. 15:46-51; Fuchs, J. R. et al. (2003) J. Pediatr. Surg. 2003; 38:984-987; Fuchs, J. R. et al. (2005) Stem Cells 23:958-964; Fuchs, J. R. et al. (2004) J. Pediatr. Surg. 39:834-838; Kaviani, A. et al. (2003) J. Am. Coll. Surg. 196:592-597; Kaviani, A. et al. (2001) J. Pediatr. Surg. 36:1662-1665), substantive advances in cell therapy for MMC have not yet been made.

Thus, a need exists in the art for compositions and method to treat CSI and related disorders. This disclosure satisfies this need and provides related advantages as well.

SUMMARY

This disclosure provides isolated cells and compositions comprising one or more isolated cell(s) as described herein. In one aspect, the isolated cell is a pre-term placenta-derived stem cell (also referred to placenta-derived multipotent stem cells (PMSCs). As used herein, the term "pre-term placenta-derived multipotent stem cell or placenta-derived stem cells" intends a cell isolated from placental tissue prior to delivery of the fetus by surgery or birth. In another aspect, the isolated cell is a chorionic villus (CV)-derived multipotent placental stem cells (C-mpSCs).

Also provided are compositions comprising these cells, wherein the composition comprises an effective amount of the isolated cells as described herein and a pharmaceutically acceptable carrier or matrix. In one aspect, the isolated placenta-derived stem cells or C-mpSCs are present in a concentration greater than physiological concentration or conditions, e.g., a concentration of greater than 10%.

Also provided are diagnostic, research and therapeutic uses of the cells and compositions comprising, or alternatively consisting essentially of, or yet further consisting of, the cells. Examples of such uses include: methods for treating Myelomeningocele (MCC) or spina bifida (SB) in a subject; methods for treating spinal cord injury or paralysis in a subject; and/or methods for treating a damaged neuron, in vitro or in vivo.

Further provided is a population of damaged neurons treated by the methods disclosed herein, and optionally a pharmaceutically acceptable carrier, matrix or biocompatible scaffold. In one aspect, the population is characterized by increased MAP2 expression and/or decreased Casp3 expression, as compared to a control population. The neuron to be treated is damaged by a neurodegenerative disease or disorder, an ischemic brain injury, a moderate or a catastrophic brain injury, a chemical neurotoxin exposure, a spinal cord injury, a traumatic brain injury, Parkinson's disease or a spinal cord contusion. These populations and compositions containing them can be used in screening assays to identify new therapeutic agents or methods to treat neurodegenerative disease or injury.

Yet further provided is a method for forming a matrix, comprising, or alternatively consisting essentially of, or yet further consisting of, combining a population of PMSCs and/or C-mpSCs with an implantable scaffolding substrate or biocompatible matrix or scaffold, optionally suitable for implantation in vivo e.g., in utero.

Kits are also provided, having an isolated, purified or cultured cell(s) as described herein and and optionally, reagents and instructions for use of one or more of: diagnostically, as a research tool or therapeutically.

Applicants have determined that the placenta, a unique organ containing tissue autologous to the fetus, is an ideal cell source for in utero stem cell therapy for MMC and other disorders. In one aspect, placental tissue can be obtained via chorionic villous sampling (CVS), an established diagnostic technique (Ahmed, S. (2006) J. Coll. Physicians Surg. Pak. 16:204-207). Unlike allogeneic cells, autologous cells carry no risk of triggering an adverse immune reaction. Most fetal autologous cell sources can only be accessed at considerable risk to the fetus or provide cells difficult to expand on a prenatal timeline (Kunisaki, S. M. et al. (2006) J. Pediatr. Surg. 41:675-682; Golombeck, K. et al. (2006) Am. J. Obstet. Gynecol. 194:834-839). In contrast, the placenta can be accessed via CVS relatively safely early in the pregnancy (Alfirevic, Z. et al. (2009) The Cochrane Library 1:1-143). Using CVS-sized samples of preterm placenta, Applicants developed a protocol to isolate CVS-derived multipotent placental stem cells (C-mpSCs) and mpSCs, characterized the cells and determined that they are a variant of mesenchymal stem cell (MSC) that can differentiate into mesodermal (osteogenic, adipogenic, chondrogenic) and ectodermal (Schwann cell-like cells, neuron-like cells) lineages. These cells can be used for autologous therapy. Cytokine array assays have shown that the cells express numerous immunomodulatory and angiogenic cytokines, indicating that the cells have the potential to affect tissue healing via paracrine activity.

Prior research (Liechty, K. W. et al. (2000) Nature Medicine 6:1282-1286; Almeida-Porada, G. et al. (2004) Yonsei Medical Journal 45:7-14) has shown that fetal lambs are immunotolerant, a quality that uniquely permits xenogeneic fetal stem cell transplantation. In addition, in utero trauma to the spinal cord in the fetal lamb MMC model occurs in the same manner as in human pathogenesis. Extensive prior literature supports the applicability of findings in this model to clinical application (von Koch, C. S. et al. (2005) American Journal of Obstetrics and Gynecology 193(4):1456-1462; Meuli, M. et al. (1995) J. Pediatr. Surg. 30:1028-1033; Paek, B. W. et al. (2000) Am. J. Obstet. Gynecol. 183:1119-1123), reinforcing the relevance of this model in evaluating cell therapies for MMC. Building upon earlier work establishing the well-accepted fetal lamb model of MMC (von Koch, C. S. et al. (2005) American Journal of Obstetrics and Gynecology 193(4):1456-1462), Applicants have revolutionarily shown that mpSCs and C-mpSCs applied during in utero repair can effect a functional cure of MMC. This research represents the first clinically-feasible treatment to consistently and dramatically improve paralysis in MMC.

Applicants also disclose herein that multipotent placenta-derived stem cells can be isolated and expanded from chorionic villous sample-sized biopsies (CVS) of pre-term human placental tissue. While CVS previously have been used to prenatally diagnose certain genetic conditions, they have not to date been used therapeutically in this way. As disclosed herein, Applicants have thoroughly characterized human mpSCs, and demonstrated their viability in hydrogel and scaffold delivery vehicles for application in utero to treat birth defects, including spina bifida. Spina bifida is a devastating birth defect resulting from incomplete closure of the neural tube during development. The exposed spinal cord is vulnerable to in utero damage, which ultimately results in lifelong lower limb paralysis. While in utero stem cell therapy for congenital anomalies has been proposed previously, it has only been effectively and safely used clinically in an extremely small number of patients with congenital immunodeficiency disorders. As C-mpSCs isolated from human placenta are autologous to the fetus, they will not instigate or participate in an immune response compromising the integrity of the graft or the efficacy of the treatment; while others have proposed using allogeneic cells for in utero therapy, the in utero and long term safety of these cells remains to be tested. Applicants have combined human mpSCs with collagen, and applied them during prenatal repair of spina bifida in Applicants' well-established, immunotolerant fetal lamb model. Untreated lambs cannot bear weight on their hind limbs and cannot stand. Treated lambs can independently stand, walk and run.

This and other advantages of Applicants' disclosure are described in more detail herein.

BRIEF DESCRIPTION OF THE DRAWINGS

FIGS. 9A-9B show differentiation into ectodermal and mesodermal lineages. Directed differentiation of bone marrow MSCs, term pMSCs (via explant), and pre-term pMSCs (via enzyme dissociation) into (A) ectodermal lineages (Schwann cells and neurons) and (B) mesodermal lineages (osteogenic, adipogenic, and chondrogenic). Scale bars=100 μm.

FIGS. 18A-18B show a Sheep Locomotor Rating Scale. (A) This table demonstrates the 7 motor function categories used to grade the newborn lambs. (B) Scores resulted in a numeric grade ranging from 0 (complete hindlimb paralysis) to 15 (normal locomotion) based on the grading system presented here.

DETAILED DESCRIPTION

Definitions

Figure 1:
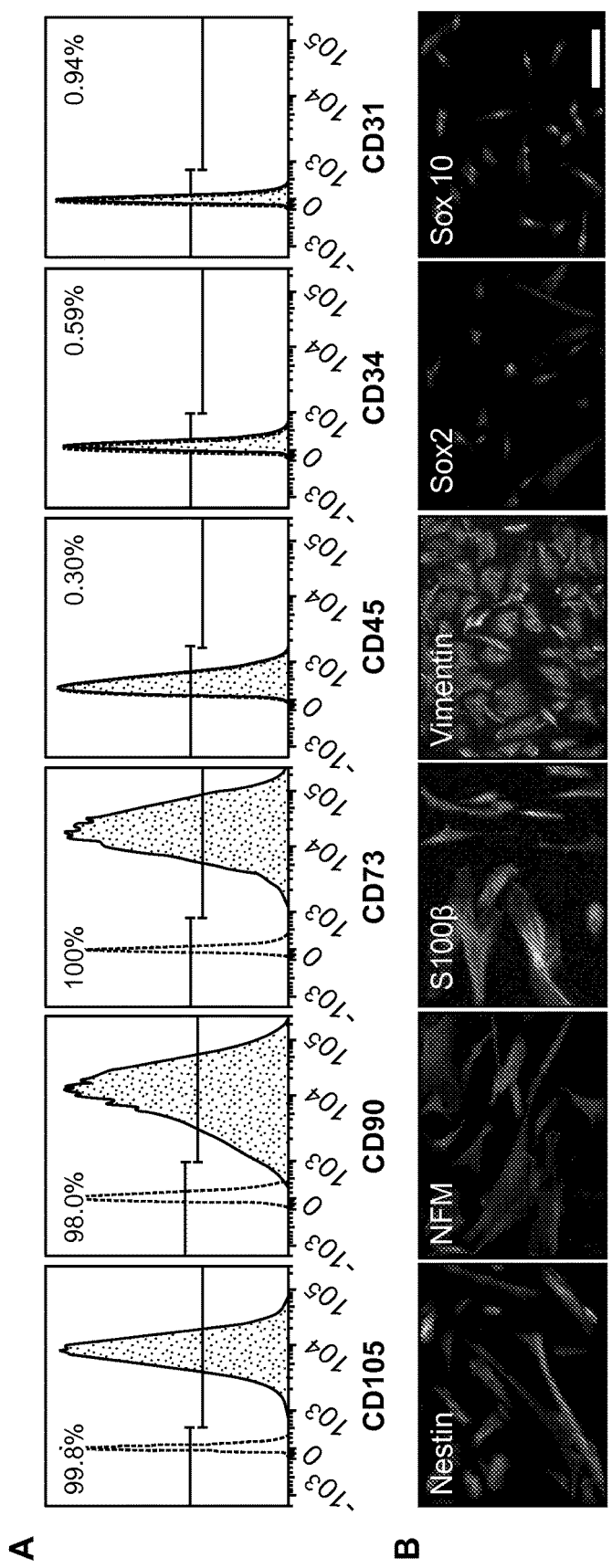
FIG. 1A shows flow cytometry analysis of 14 week GA C-mpSCs showing positivity for MSC markers CD105, CD90, and CD73 and negativity for hematopoietic and endothelial markers CD45, CD34, and CD31.
FIG. 1B shows immunocytochemical staining of C-mpSCs for intracellular proteins Nestin, NFM, S100β, and Vimentin, as well as transcription factors Sox2 and Sox10. Scale bars=100 µm.

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis (1989) Molecular Cloning: A Laboratory Manual, $2^{nd}$ edition; F. M. Ausubel, et al. eds. (1987) Current Protocols In Molecular Biology; the series Methods in Enzymology (Academic Press, Inc.): PCR 2: A Practical Approach (1995) (M. J. MacPherson, B. D. Hames and G. R. Taylor eds.); Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, or 98%. The term "isolated" is also used herein to refer to cells or tissues that are isolated from other cells or tissues and can encompass cultured and/or engineered cells or tissues.

As used herein, "stem cell" defines a cell with the ability to divide for indefinite periods in culture and give rise to specialized cells. At this time and for convenience, stem cells are categorized as somatic (adult), embryonic or induced pluripotent stem cells. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. Non-limiting examples of embryonic stem cells are the HES2 (also known as ES02) cell line available from ESI, Singapore and the H1 or H9 (also known as WA01) cell line available from WiCell, Madison, Wis. Pluripotent embryonic stem cells can be distinguished from other types of cells by the use of markers including, but not limited to, Oct-4, alkaline phosphatase, CD30, TDGF-1, GCTM-2, Genesis, Germ cell nuclear factor, SSEA1, SSEA3, and SSEA4. An induced pluripotent stem cell (iPSC) is an artificially derived stem cell from a non-pluripotent cell, typically an adult somatic cell, produced by inducing expression of one or more stem cell specific genes.

A "parthenogenetic stem cell" refers to a stem cell arising from parthenogenetic activation of an egg. Methods of creating a parthenogenetic stem cell are known in the art. See, for example, Cibelli et al. (2002) Science 295(5556): 819 and Vrana et al. (2003) Proc. Natl. Acad. Sci. USA 100(Suppl. 1)11911-6 (2003).

"Embryoid bodies or EBs" are three-dimensional (3-D) aggregates of embryonic stem cells formed during culture that facilitate subsequent differentiation. When grown in suspension culture, EBs cells form small aggregates of cells surrounded by an outer layer of visceral endoderm. Upon growth and differentiation, EBs develop into cystic embryoid bodies with fluid-filled cavities and an inner layer of ectoderm-like cells.

The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue. In yet another embodiment, the tissue is comprised of neuronal progenitor cells or neuronal cells.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells. A "cultured" cell is a cell that has been separated from its native environment and propagated under specific, pre-defined conditions.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

A "marrow stromal cell" also referred to as "mesenchymal stem cells," or MSC, is a multipotent stem cell that can differentiate into a variety of cell types. Cell types that MSCs have been shown to differentiate into in vitro or in vivo include osteoblasts, chondrocytes, myocytes, and adipocytes. Mesenchyme is embryonic connective tissue that is derived from the mesoderm and that differentiates into hematopoietic and connective tissue, whereas MSCs do not differentiate into hematopoietic cells. Stromal cells are connective tissue cells that form the supportive structure in which the functional cells of the tissue reside. Methods to isolate such cells, propogate and differentiate such cells are known in the technical and patent literature, e.g., U.S. Patent Application Publication Nos. 2007/0224171, 2007/0054399 and 2009/0010895, which are incorporated by reference in their entirety.

"pMSC" or "PMSC" or "mpSCs" are acronyms for mesenchymal stem cells isolated or purified from placental tissue prior to delivery of the fetus by surgery or birth. Within this disclosure, the cells also are referred to as pre-term placenta-derived stem cell (mpSCs) or when isolated by chorionic villus sampling, they are identified as C-mpSCs. In one aspect, the PMSC express angiogenic and immunomodulatory cytokines (e.g. Angiogenin, Angiopoietin-1, HGF, VEGF, IL-8, MCP-4, uPA).

Chorionic Villus Sampling (CVS) is a technique to diagnose complications during a pregnancy. A small section of placental tissue is collected without disturbing the pregnancy, and these cells are examined for disease. The tissue sampled is the chorionic villus, and CVS is the technique used to obtain chorionic villus samples.

"BDNF" is an acronym for Brain Derived Neurotropic Factor that is vital to healing in the nervous system. An exemplary sequence for human BDNF protein is disclosed at Accession No.: NP_00137277 and mRNA is disclosed at NM_001143805. An exemplary murine BDNF is disclosed at NP_001041604 and mRNA is disclosed at NM_001048139.

CD56 is also known as N-CAM (neural cell adhesion molecule) and is reported to act as a hemophilic binding glycoprotein with a role in cell-cell adhesion. The human protein sequence is disclosed at P13591 (niProtKB/Swiss-Prot). A polynucleotide and protein encoded by the polynucleotide are at GenBank number NM_001076682. Additional information regarding the gene and transcripts is disclosed at genecards.org/cgi-bin/carddisp.pl?gene=NCAM1 (last accessed on Aug. 13, 2014). Antibodies to the marker and polynucleotides encoding the marker are commercially available from Sino Biological (old.sinobiological.com/NCAM1-CD56-a-6632.html, last access on Aug. 13, 2014) and Life Technologies.

CD271 is also known as the Nerve Growth Factor Receptor (NGFR). The protein is reported to contain an extracellular domain containing four 40-amino acid repeats with cysteine residues at conserved positions followed by a serine/threonine-rich region, a single transmembrane domain and a 155 amino acid cytoplasmic domain. The human protein sequence is disclosed at TNR16 HUMAN, P08138 (uniprot.org/uniprot/P08138#section_comments, last accessed on Aug. 13, 2014). A polynucleotides encoding the marker is under GenBank No. NM_002507 (see also genecards.org/cgi-bin/carddisp.pl?gene=NGFR, last accessed on Aug. 13, 2014). Antibodies are commercially available from Miltenyi Biotech and other vendors.

CD105 is also known as Endoglin (ENG) is reported to be a 658 amino acid sequence and a homodimer that forms a heteromeric complex with the signaling receptors for transforming growth factor-beta (TGFBR). A polynucleotide encoding the marker and an amino acid sequence is disclosed under GenBank No. M_001278138 (see also genecards.org/cgi-bin/carddisp.pl?gene=ENG, last accessed on Aug. 13, 2014). Antibodies to the marker are commercially available from numerous vendors, e.g., R&D Systems Antibodies, Novus Biologicals and Abcam antibodies.

CD90 also is known as Thy-1. A polynucleotide encoding the marker and an amino acid sequence are disclosed under GenBank number NM_006288. Additional information regarding the marker and vendors that provide antibodies to the marker are disclosed under Genecards reference: genecards.org/cgi-bin/carddisp.pl?gene=THY1, last accessed on Aug. 13, 2014.

CD73 also is known as NT5E. The protein is reported to be a gene is a plasma membrane protein that catalyzes the conversion of extracellular nucleotides to membrane-permeable nucleosides. The encoded protein is used as a determinant of lymphocyte differentiation. Defects in this gene can lead to the calcification of joints and arteries. Two transcript variants encoding different isoforms have been reported for this gene. See genecards.org/cgi-bin/carddisp.pl?gene=NT5E, last accessed on Aug. 13, 2014. A polynucleotides encoding the protein and an encoded amino acid sequences are disclosed under GenBank number BC065937. Antibodies to the marker are commercially available from several vendors, e.g., R&D Systems Antibodies.

CD44 is reported to be a cell-surface glycoprotein involved in cell-cell interactions, cell adhesion and migration. It is a receptor for hyaluronic acid (HA) and can also interact with other ligands, such as osteopontin, collagens, and matrix metalloproteinases (MMPs). A polynucleotide and encoded amino acid sequence are disclosed under GenBank number FJ216964 (last accessed Aug. 13, 2014). Additional information regarding the marker and commercially available antibodies to the marker are disclosed at genecards.org/cgi-binicarddisp.pl?gene=CD44, last accessed on Aug. 13, 2014.

CD29 also is known as Integrin Beta 1, Fibronectin Receptor, Beta Polypeptide (see Genecards: genecards.org/cgi-binicarddisp.pl?gene=ITGB1, last accessed on Aug. 13, 2014). A polynucleotide and protein encoded by the polynucleotide are disclosed under GenBank number NG_029012. Additional information regarding the marker and commercially available antibodies to the marker are disclosed at genecards.org/cgi-binicarddisp.pl?gene=CD44, last accessed on Aug. 13, 2014.

CD184 also is known as "chemockine (C-X-C Motif) receptor." The protein is reported to have transmembrane regions and is located on the cell surface. It acts with the CD4 protein to support HIV entry into cells and is also highly expressed in breast cancer cells. A polynucleotide and encoded amino acid sequence are disclosed under GenBank number NM_003467. Additional information regarding the marker and commercially available antibodies to the marker are disclosed at genecards.org/cgi-binicarddisp.pl?gene=CXCR4, last accessed on Aug. 13, 2014.

CD49d (also known as ITGA4) is an integrin alpha subunit. It makes up half of the α4β1 lymphocyte horning receptor. The product of this gene is reported to be a member of the integrin alpha chain family of proteins. Integrins are heterodimeric integral membrane proteins composed of an alpha chain and a beta chain. The gene encoding CD49d encodes an alpha 4 chain. A polynucleotide and amino acid sequence encoded by it is reported under GenBank number NM_000885. Additional information regarding the marker and commercially available antibodies to the marker are disclosed at genecards.org/cgi-binicarddisp.pl?gene=TRIM49D1, last accessed on Aug. 13, 2014.

CD49f is also known as integrin, alpha 6 or ITGA6. The product of this gene is reported to be a member of the integrin alpha chain family of proteins. A polynucleotide and amino acid sequence encoded by it is reported under GenBank number NM_000210. Additional information regarding the marker and commercially available antibodies to the marker are disclosed at genecards.org/cgi-binicarddisp.pl?gene=ITGA6, last accessed on Aug. 13, 2014.

CD31 also is known as platelet/endothelial cell adhesion molecule 1 (PECAM1). A polynucleotide and amino acid sequence encoded by it is reported under GenBank number AF281301. Additional information regarding the marker and commercially available antibodies to the marker are disclosed at genecards.org/cgi-binicarddisp.pl?gene=PECAM1, last accessed on Aug. 13, 2014.

CD34 is a cell surface marker. A polynucleotide and amino acid sequence encoded by it is reported under GenBank number M81104 (X60172). Additional information regarding the marker and commercially available antibodies to the marker are disclosed at genecards.org/cgi-binicarddisp.pl?gene=CD34, last accessed on Aug. 13, 2014.

CD45 also is known as protein tyrosine phosphatase, receptor type C (PTPRC). A polynucleotide and amino acid sequence encoded by it is reported under GenBank number AY538691. Additional information regarding the marker and commercially available antibodies to the marker are disclosed at genecards.org/cgi-binicarddisp.pl?gene=PTPRC, last accessed on Aug. 13, 2014.

The acronym "HGF" intends "hepatocyte growth factor". A polynucleotide encoding HGF and amino acid sequence encoded therefrom is deposited under GenBank Accession number D90334.2. Information regarding HGF and antibodies to detect and quantify HGF as well as commercially available assay kits are describe at genecards.org/cgi-binicardisp.pl?gene=HGF, last accessed on Aug. 14, 2014.

The acronym "IL-8" intends "interleukin 8". Information regarding IL-8 and antibodies to detect and quantify as well as commercially available assay kits are describe at genecards.org/cgi-binicarddisp.pl?gene=IL8, last accessed on Aug. 13, 2014.

As used herein, the term "integrin receptor" or "integrin" intends the cell surface marker to which a ligand can bind.

As used herein, the term "differentiates or differentiated" defines a cell that takes on a more committed ("differentiated") position within the lineage of a cell. "Dedifferentiated" defines a cell that reverts to a less committed position within the lineage of a cell.

As used herein, a "pluripotent cell" defines a less differentiated cell that can give rise to at least two distinct (genotypically and/or phenotypically) further differentiated progeny cells.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin).

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include biocompatible scaffolds, pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

A "biocompatible scaffold" refers to a scaffold or matrix for tissue-engineering purposes with the ability to perform as a substrate that will support the appropriate cellular activity to generate the desired tissue, including the facilitation of molecular and mechanical signaling systems, without eliciting any undesirable effect in those cells or inducing any undesirable local or systemic responses in the eventual host. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. No. 6,638,369.

A neuron is an excitable cell in the nervous system that processes and transmits information by electrochemical signaling. Neurons are found in the brain, the vertebrate spinal cord, the invertebrate ventral nerve cord and the peripheral nerves. Neurons can be identified by a number of markers that are listed on-line through the National Institute of Health at the following website: "stemcells.nih.gov/info/scireport/appendixe.asp#eii," and are commercially available through Chemicon (now a part of Millipore, Temecula, Calif.) or Invitrogen (Carlsbad, Calif.).

As used herein and known to the skilled artisan, a "marker" is a receptor or protein expressed by the cell or internal to the cell which can be used as an identifying and/or distinguishing factor. If the marker is noted as ("+"), the marker is positively expressed. If the marker is noted as ("−"), the marker is absent or not expressed. Variable expression of markers are also used, such as "high" and "low" and relative terms.

A neural stem cell is a cell that can be isolated from the adult central nervous systems of mammals, including humans. They have been shown to generate neurons, migrate and send out aconal and dendritic projections and integrate into pre-existing neuroal circuits and contribute to normal brain function. Reviews of research in this area are found in Miller (2006) Brain Res. 1091(1):258-264; Pluchino et al. (2005) Brain Res. Brain Res. Rev. 48(2):211-219; and Goh et al. (2003) Stem Cell Res. 12(6):671-679. Neural stem cells have previously been identified and isolated by neural stem cell specific markers including, but limited to, CD133, ICAM-1, MCAM, CXCR4 and Notch 1. Neural stem cells can be isolated from animal or human by neural stem cell specific markers with methods known in the art. See, e.g., Yoshida et al. (2006) Stem Cells 24(12):2714-22.

A "precursor" or "progenitor cell" intends to mean cells that have a capacity to differentiate into a specific type of cell. A progenitor cell may be a stem cell. A progenitor cell may also be more specific than a stem cell. A progenitor cell may be unipotent or multipotent. Compared to adult stem cells, a progenitor cell may be in a later stage of cell differentiation. An example of progenitor cell include, without limitation, a progenitor nerve cell.

A "neural precursor cell", "neural progenitor cell" or "NP cell" refers to a cell that has a capacity to differentiate into a neural cell or neuron. A NP cell can be an isolated NP cell, or derived from a stem cell including but not limited to an iPS cell. Neural precursor cells can be identified and isolated by neural precursor cell specific markers including, but limited to, nestin and CD133. Neural precursor cells can be isolated from animal or human tissues such as adipose tissue (see, e.g., Vindigni et al. (2009) Neurol. Res. 2009 Aug. 5. [Epub ahead of print]) and adult skin (see, e.g., Joannides (2004) Lancet. 364(9429):172-8). Neural precursor cells can also be derived from stem cells or cell lines or neural stem cells or cell lines. See generally, e.g., U.S. Patent Application Publications Nos. 2009/0263901, 2009/0263360 and 2009/0258421.

A nerve cell that is "terminally differentiated" refers to a nerve cell that does not undergo further differentiation in its native state without treatment or external manipulation. In one embodiment, a terminally differentiated cell is a cell that has lost the ability to further differentiate into a specialized cell type or phenotype.

A population of cells intends a collection of more than one cell that is identical (clonal) or non-identical in phenotype and/or genotype.

The term neurodegenerative condition (or disorder) is an inclusive term encompassing acute and chronic conditions, disorders or diseases of the central or peripheral nervous system. A neurodegenerative condition may be age-related, or it may result from injury or trauma, or it may be related to a specific disease or disorder. Acute neurodegenerative conditions include, but are not limited to, conditions associated with neuronal cell death or compromise including cerebrovascular insufficiency, focal or diffuse brain trauma, diffuse brain damage, spinal cord injury or peripheral nerve trauma, e.g., resulting from physical or chemical burns, deep cuts or limb severance. Examples of acute neurodegenerative disorders are: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), as well as whiplash and shaken infant syndrome. Chronic neurodegenerative conditions include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neuro-degeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia), demyelination diseases and disorders including multiple sclerosis and hereditary diseases such as leukodystrophies.

Other neurodegenerative conditions include dementias, regardless of underlying etiology, including age-related dementia and other dementias and conditions with memory loss including dementia associated with Alzheimer's disease, vascular dementia, diffuse white matter disease (Binswanger's disease), dementia of endocrine or metabolic origin, dementia of head trauma and diffuse brain damage, dementia pugilistica and frontal lobe dementia.

The term treating (or treatment of) a neurodegenerative disorder or condition refers to ameliorating the effects of, or delaying, halting or reversing the progress of, or delaying or preventing the onset of, a neurodegenerative condition as defined herein. In one aspect, "treatment" is an improvement in locomoter function as compared to untreated controls, such as for example, the ability for self-care, to bear weight and/or become ambulatory (walk).

The term effective amount refers to a concentration or amount of a reagent or composition, such as a composition as described herein, cell population or other agent, that is effective for producing an intended result, including cell growth and/or differentiation in vitro or in vivo, or for the treatment of a neurodegenerative condition as described herein. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or composition to achieve its intended result, e.g., the differentiation of cells to a pre-determined cell type.

The term patient or subject refers to animals, including mammals, such as bovines, canines, felines, ovines, equines, preferably humans, who are treated with the pharmaceutical compositions or in accordance with the methods described herein.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

A "control" is an alternative subject or sample used in an experiment for comparison purpose. A control can be "positive" or "negative". For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype). Additionally, when the purpose of the experiment is to determine if an agent effects the differentiation of a stem cell, it is preferable to use a positive control (a sample with an aspect that is known to affect differentiation) and a negative control (an agent known to not have an affect or a sample with no agent added).

The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

As used herein, a "pluripotent cell" defines a less differentiated cell that can give rise to at least two distinct (genotypically and/or phenotypically) further differentiated progeny cells. In another aspect, a "pluripotent cell" includes a Induced Pluripotent Stem Cell (iPSC) which is an artificially derived stem cell from a non-pluripotent cell, typically an adult somatic cell, produced by inducing expression of one or more stem cell specific genes. Such stem cell specific genes include, but are not limited to, the family of octamer transcription factors, i.e., Oct-3/4; the family of Sox genes, i.e. Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e. OCT4, NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

DETAILED DESCRIPTION

Cells and Compositions

This disclosure provides isolated cells and compositions comprising one or more isolated cell as described herein. In one aspect, the isolated cell is a pre-term placenta-derived stem cell (PMSCs or mpSCs). As used herein the term "pre-term placenta-derived stem cell" intends a cell isolated from placental tissue prior to delivery of the fetus by surgery or birth. In one aspect, the cell is isolated in the first or second trimester.

In another aspect, the isolated cell is isolated by a procedure known as chorionic villous sampling and therefore termed (CVS)-derived multipotent placental stem cells (C-mpSCs). This cell population can be used for autologous cell therapy.

Whether the cells are PMSCs, mpSCs or C-mpSCs, the cells are characterized by expression of one or both markers of the group $CD56^+$ and $CD271^+$. In a further aspect, the PMSCs are further characterized by one or more of:

expression of one or more markers of the group: $CD105^+$, $CD90^+$, $CD73^+$, $CD44^+$ and $CD29^+$;

by expression of the marker $CD184^+$;

by expression of an integrin receptor, optionally CD49d and/or CD49f;

by expression of an intracellular marker, optionally of Nestin, Vimentin, S100β and/or neurofilament medium (NFM);

by expression of an transcriptional factor, optionally one or more of Sox2, Sox10, Sox17 and/or Slug;

by lack of expression of one or more of endothelial markers and/or hematopoietic markers, such as CD31, CD34 and CD45.

In one aspect, the cells are characterized by expression of one or both markers of the group $CD56^+$ and $CD271^+$. In another aspect, the cells are further characterized by expression of one or more markers of the group: $CD105^+$, $CD90^+$, $CD73^+$, $CD44^+$ and $CD29^+$.

In another aspect the cells are characterized by expression of two or more, three or more, four or all five additional markers. In another aspect, the cells are further characterized by expression of the marker $CD184^+$.

The cells can be further characterized by expression of an integrin receptor, optionally CD49d and/or CD49f. In another aspect, both integrin receptors are expressed.

The cells can be further characterized by the expression of an intracellular marker, optionally one or more of Nestin, Vimentin, S100β and/or neruofilament medium (NFM), or two or more or three or all four intracellular markers.

The cells can be further characterized by expression of one or more transcriptional factor, e.g., one or more of Sox2, Sox10, Sox17 and/or Slug, or two or more, or three or all four.

The cells are further characterized by lack of expression of one or more of endothelial markers and/or hematopoietic markers.

The composition of claim 9, wherein said marker is one or more of the group of: CD31, CD34 and CD45, or two or all three.

Applicants have characterized the cells and compared them to bone marrow MSCs, term pMSCs and pre-term pMSCs, and found differences among the two cell types. Pre-term pMSCs and bone marrow MSCs expressed the transcriptional repressor Snail, although it was found to be lacking in term pMSCs. As well, term pMSCs lacked Sox2 expression and showed very dim staining of Sox17, where the other cell types were observed positive for both. Importantly, the PMSCs also exhibited a unique secretory profile. The PMSCs secreted substantially and significantly more HGF, IL-8 and BDNF than BM-MSCs. They also secreted at least 2×, or alternatively at least 3×, or alternatively at least 4×, BNDF as compared to BM-MSCs. Thus, the cells isolated and disclosed herein are not identical to BM-MSCs.

Methods to identify and separate or purify the cells are known to those of skill in the art and described herein.

Further provided is a population of cells, as described above. The population can be substantially homogenous, e.g., having greater than 50%, or alternatively greater than 60%, or alternatively greater than 70%, or alternatively greater than 80%, or alternatively greater than 85%, or alternatively greater than 90%, or alternatively greater than 95%, or alternatively greater than 98% or alternatively a clonal population of cells.

In one aspect, the population of cells comprises, or alternatively consists essentially of, or yet further consists of, isolated cell placenta-derived stem cells that are present at a concentration of greater than 10%, or alternatively greater than 20%, or alternatively greater than 30%, or alternatively greater than 40%, than the cells exist in nature.

The cells can be used diagnostically, as a research reagent or therapeutically as described herein. The isolated cells also can be cultured and expanded to maintain a desired phenotype, e.g., an identical phenotype or a clonal population of cells (as determined by identifying markers) and/or cultured and differentiated into a cell of another desired phenotype, using methods and reagents as known in the art. The cells are cultured under suitable conditions to provide the desired population of cells.

In one aspect, the cell to be cultured is a damaged neuron (e.g., cortical neuron or a spinal cord neuron) that is cultured in the presence of an effective amount of concentrated mesenchymal stem cell culture conditional media (MSC CM) for an effective time. In one aspect, the the neuron to be treated is damaged by a neurodegenerative disease or disorder, an ischemic brain injury, a moderate or a catastrophic brain injury, a chemical neurotoxin exposure, a spinal cord injury, a traumatic brain injury, Parkinson's disease, or an injury, e.g., or a spinal cord contusion.

Non-limiting examples of MSC CMs include those collected from bmMSC or PMSC cultures and concentrated in an amount selected from the group of at least about 5 fold; or at least about 10 fold; or at least about 15 fold; or at least about 20 fold; or at least about 25 fold; or at least about 30 fold; or at least about 35 fold; or at least about 40 fold; or at least about 45 fold; or at least about 50 fold; or at least about 55 fold; or at least about 60 fold; or at least about 65 fold; or at least about 70 fold; or at least about 75 fold; or at least about 80 fold; or at least about 85 fold; or at least about 90 fold. A population of cells treated or cultured by the method can optionally contain a pharmaceutically acceptable carrier, matrix or a biocompatible scaffold. In one aspect, the cell or the population of cells is characterized by increased MAP2 expression and/or decreased Casp3 expression, as compared to a control population.

Cells treated by this method are further provided herein as well as methods to isolate and culture the cells.

The isolated cell, population of cells, or composition of cells can be modified by transfection of a gene that may or may not provide an additional therapeutic or diagnostic function to the cell or population of cells. For example, a gene expressing a detectable label can be inserted into the cell or alternatively linked or coupled to the cell to facilitate diagnostic and/or therapeutic use. Alternatively, the cell or additional agent can assist with the preparation of a therapeutic or diagnostic composition, e.g., by facilitating the isolation of a desired phenotype of cell.

Also provided herein are compositions comprising one or more of the isolated cells as described herein. In one aspect, composition is provided, wherein the composition comprises, or alternatively consists essentially of, or yet further consists of, an effective amount of pre-term placenta-derived stem cells, e.g., chorionic villous sampling (CVS)-derived multipotent placental stem cells (C-mpSCs) and a pharmaceutically acceptable carrier or matrix. In one aspect, the effective amount is a therapeutically effective amount.

Also provided is a composition containing at least one isolated cell or a population of cells as described herein. The compositions include, for example, pharmaceutical and diagnostic compositions/kits, comprising a pharmaceutically acceptable carrier and at least one cell or population of cells and can further comprise a detectable marker, an additional growth factors and/or therapeutic agents which in combination, provide multiple therapies tailored to provide the maximum therapeutic benefit.

In one aspect, the pharmaceutically acceptable carrier or matrix is a biocompatible matrix suitable for in vivo implantation of the stem cells. Non-limiting examples of such include, a hydrogel, a thixotropic agent, a phase changing agent, a collagen gel, a collagen matrix, an extracellular matrix (ECM), an amnion patch, a nanofiber scaffold (aligned and nonaligned) and fibrin glue.

The cells can be of any appropriate species, e.g., a mammal such as a bovine, ovine, feline, canine, equine, or a human cell. When used therapeutically, the cells and populations can be autologous or allogeneic to the subject to be treated.

Further provided are methods to prepare the composition comprising admixing an effective amount of the cell or population of cells with a carrier as described herein. In one aspect, between 50,000 and $1 \times 10^6$ cells are mixed, or alternatively between 50,000 and $0.75 \times 10^6$, or alternatively between 100,000 and $0.75 \times 10^6$, or alternatively between 200,000 and $7 \times 10^5$, or alternatively between 300,000 and 600,000, or alternatively about 500,000 cells are mixed per ml or carrier.

Alternatively, a composition of this invention can be co-administered with other therapeutic agents, whether or not linked to them or administered in the same dosing. They can be co-administered simultaneously with such agents (e.g., in a single composition or separately) or can be administered before or after administration of such agents. Compositions for these purposes are further provided herein.

Methods to Identify Therapeutic Agents

The present invention also provides compositions and methods to identify leads and methods for neurodegenerative diseases, MCC, or spinal cord injury. In one aspect, the screen identifies lead compounds or biologics agents that mimic the cells identified above and which are useful to treat these disorders or to treat or ameliorate the symptoms associated with the disorders. Test substances for screening can come from any source. They can be libraries of natural products, combinatorial chemical libraries, biological products made by recombinant libraries, etc. The source of the test substances is not critical to the invention. The present invention provides means for screening compounds and compositions which may previously have been overlooked in other screening schemes.

To practice the screen or assay in vitro, suitable cell cultures or tissue cultures are first provided. The cell can be a cultured cell or a genetically modified cell which expresses a pre-determined marker. The cells are cultured under conditions (temperature, growth or culture medium and gas ($CO_2$)) and for an appropriate amount of time to attain exponential proliferation without density dependent constraints. It also is desirable to maintain an additional separate cell culture; one which does not receive the agent being tested as a control.

As is apparent to one of skill in the art, suitable cells may be cultured in microtiter plates and several agents may be assayed at the same time by noting genotypic changes or the expression of lack thereof of certain identifiable markers.

When the agent is a composition other than a DNA or RNA nucleic acid molecule, the suitable conditions may be by directly added to the cell culture or added to culture medium for addition. As is apparent to those skilled in the art, an "effective" amount must be added which can be empirically determined.

The screen involves contacting the agent with a test cell and then assaying the cell for its ability to provide a biological response similar to the cell of this disclosure.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. It should be understood, although not always explicitly stated that the agent is used alone or in combination with another agent, having the same or different biological activity as the agents identified by the disclosed screen. The agents and methods also are intended to be combined with other therapies. They can be administered concurrently or sequentially.

Methods of Use of the Cells, Populations and Compositions

In one aspect, the cells and compositions are useful in a method for treating Myelomeningocele (MCC) or spina bifida (SB) in a subject in need thereof, the method comprising, or alternatively consisting essentially of, or yet further consisting of, administering to a subject in need thereof a therapeutically effective amount of an isolated cell or composition as described herein. In one aspect, the subject is a fetus and the composition is administered to the fetus in utero. The subject typically is a mammal, e.g., an equine, a bovine, a canine, a ovine, a rat, a lamb, or a human patient. The cells are allogeneic or autologous to the subject being treated. In one aspect, the cell or population of cells are combined with a pharmaceutically acceptable carrier such as a biocompatible matrix or gel, and surgically implanted to the site of neural injury or site for regeneration, e.g., the neural placode. The cells in the matrix can be secured in vivo by overlay with a commercially available ECM patch. In one aspect, between 50,000 and $1 \times 10^6$ cells are administered, or alternatively between 50,000 and $0.75 \times 10^6$, or alternatively between 100,000 and $0.75 \times 10^6$, or alternatively between 200,000 and $7 \times 10^5$, or alternatively between 300,000 and 600,000, or alternatively about 500,000 cells are administered per dose.

Also provided is a method for treating spinal cord injury or paralysis in a subject in need thereof, the method comprising, or alternatively consisting essentially of, or yet further consisting of, administering to the subject a therapeutically effective amount of an isolated cell or composition as described herein. The subject typically is a mammal, e.g., an equine, a bovine, a canine, a ovine, a rat, a lamb, or a human patient. The cells are allogeneic or autologous to the subject being treated. In one aspect, the cell or population of cells are combined with a pharmaceutically acceptable carrier such as a biocompatible matrix or gel, and surgically implanted to the site of injury or for regeneration, e.g., the neural placode. Non-limiting examples of such include, a hydrogel, a thixotropic agent, a phase changing agent, a collagen gel, a collagen matrix, an extracellular matrix (ECM), an amnion patch, a nanofiber scaffold (aligned and nonaligned) and fibrin glue. The cells in matrix can be secured in vivo by overlay with a commercially available ECM patch. In one aspect, between 50,000 and $1\times10^6$ cells are administered, or alternatively between 50,000 and $0.75\times10^6$, or alternatively between 100,000 and $0.75\times10^6$, or alternatively between 200,000 and $7\times10^5$, or alternatively between 300,000 and 600,000, or alternatively about 500,000 cells are administered per dose.

Yet further provided is a method for treating a damaged neuron, comprising or alternatively consisting essentially of, or yet further consisting of, contacting the neuron with an effective amount of concentrated mesenchymal stem cell culture conditional media (MSC CM) for an effective amount of time, thereby treating the damaged neuron. In one aspect, the neuron is an isolated cortical neuron or a spinal cord neuron. In a further aspect, the MSC CMs is collected from bmMSC or pMSC cultures and concentrated in an amount selected from the group of at least about 5 fold; or at least about 10 fold; or at least about 15 fold; or at least about 20 fold; or at least about 25 fold; or at least about 30 fold; or at least about 35 fold; or at least about 40 fold; or at least about 45 fold; or at least about 50 fold; or at least about 55 fold; or at least about 60 fold; or at least about 65 fold; or at least about 70 fold; or at least about 75 fold; or at least about 80 fold; or at least about 85 fold; or at least about 90 fold. The contacting can be in vitro or in vivo.

Subjects that can be treated with the methods of this disclosure include a mammal, e.g., a mouse, a rat, a lamb, a canine, a feline, an equine, an ovine, a bovine or a human patient. The cells can be autologous or allogeneic to the subject and can be further modified as described herein. In addition, the methods can further comprise, or alternatively consist essentially of, or yet further consist of, administration of an effective amount of an additional agent, e.g., a growth factor and/or therapeutic agents which in combination, provide multiple therapies tailored to provide the maximum therapeutic benefit. A non-limiting example of such is administration of an effective amount of BNDF. These can be combined in the same composition for administration or co-administered in separate formulations. They can be co-administered simultaneously with such agents (e.g., in a single composition or separately) or can be administered before or after administration of such agents.

An "effective amount" is an amount sufficient to effect beneficial or desired results. An effective amount can be administered in one or more administrations, applications or dosages. Such delivery is dependent on a number of variables including the time period for treatment, the route of administration, etc. It is understood, however, that specific dose levels of the cell or population of cells for any particular subject depends upon a variety of factors including the activity of the cell, population or composition, the age, body weight, general health, sex, and diet of the subject, the time of administration, any drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the cell, population or composition of this disclosure to provide the therapeutic benefit in vitro or in vivo by at least 10%, 25%, 40%, 60%, 80%, 90% or 95% as compared to control. Determination of these parameters is well within the skill of the art. These considerations, as well as effective formulations and administration procedures are well known in the art and are described in standard textbooks.

The "therapeutically effective amount" will vary depending on the cell, composition, or population, the disease and its severity and the age, weight, etc., of the patient to be treated all of which is within the skill of the attending clinician. It is contemplated that a therapeutically effective amount of a cell, population or composition described herein will provide the therapeutic benefit to the patient as compared to the absence of treatment. In Applicants' large animal studies, the dose was defined as $5\times10^5$ PMSCs in a 1 ml of collagen based matrix. The exact final dose for administration to humans or other mammals can be determined by extrapolation of this dosing by the treating physician or veterinarian. A single product dose will be topically applied to the open wound of the fetal spinal defect during in utero surgical repair. No further doses may be needed, but the treatment protocol will be determined by the treating physician, the condition being treated and the subject undergoing treatment. In one aspect, a dose is between about $1\times10^5$ to $1\times10^{10}$ cells, or alternatively $2\times10^5$ to $1\times10^9$ cells, or alternatively from about $3\times10^5$ to $1\times10^8$ cells, or alternatively from about $3\times10^5$ to $1\times10^7$ cells, or alternatively from about $3\times10^5$ to $1\times10^8$ cells, or alternatively from about $2\times10^5$ to $1\times10^7$ cells, or alternatively from about $4\times10^5$ to $1\times10^6$ cells, or alternatively about $4\times10^5$ to $6\times10^5$ cells, or alternatively from about $5\times10^5$ cells per dose. In one aspect, the carrier is a biocompatible matrix, e.g., a collagen based matrix and the cells are contained in an amount of from about 0.5 ml to about 3 ml, or about 0.5 ml to about 2 ml, or about 1 ml of matrix or carrier.

Administration in vivo can be effected in one dose, continuously or intermittently throughout the course of treatment. Methods of determining the most effective means and dosage of administration are well known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents can be found below.

While it is possible for the cell or population of cells to be administered alone, it may be preferable to present it as a pharmaceutical formulation comprising at least one cell or population as defined above, together with one or more pharmaceutically acceptable carriers therefor and optionally other therapeutic agents. Each carrier must be "acceptable" in the sense of being compatible with the other ingredients of the formulation and not injurious to the patient. In one aspect, an effective amount of BNDF is combined and/or co-administered in a separate formulation with the cells.

Kits

A kit comprising an isolated cell, a population of cells or a composition as described herein is further provided herein.

The kits and optionally, reagents and instructions for use of one or more diagnostically, as a research tool or therapeutically.

The following examples are provided to illustrate and not limit the inventions as disclosed herein.

EXPERIMENTAL

Experiment 1
Isolation and Characterization of C-mpSCs

Applicants established a protocol to isolate C-mpSCs from human preterm placenta using CVS tissue explant culture. Applicants' in vitro studies demonstrated that a substantial quantity of C-mpSCs can be isolated and expanded on the 7-14 week surgical timeline between conventional CVS (10-14 weeks) and MMC repair (21-24 weeks). C-mpSCs express MSC markers CD105, CD90, CD73, CD44, and CD29 but do not express hematopoietic and endothelial markers CD31, CD34 and CD45. Applicants also found that C-mpSCs uniquely express cytokine receptor CD184 (CXCR4), integrins CD49d and CD49f, intracellular markers Nestin, Vimentin, S100β, and NFM and transcriptional factors Sox2, Sox10, Sox17 and Slug (representatively shown in FIG. 1).

Figure 2:
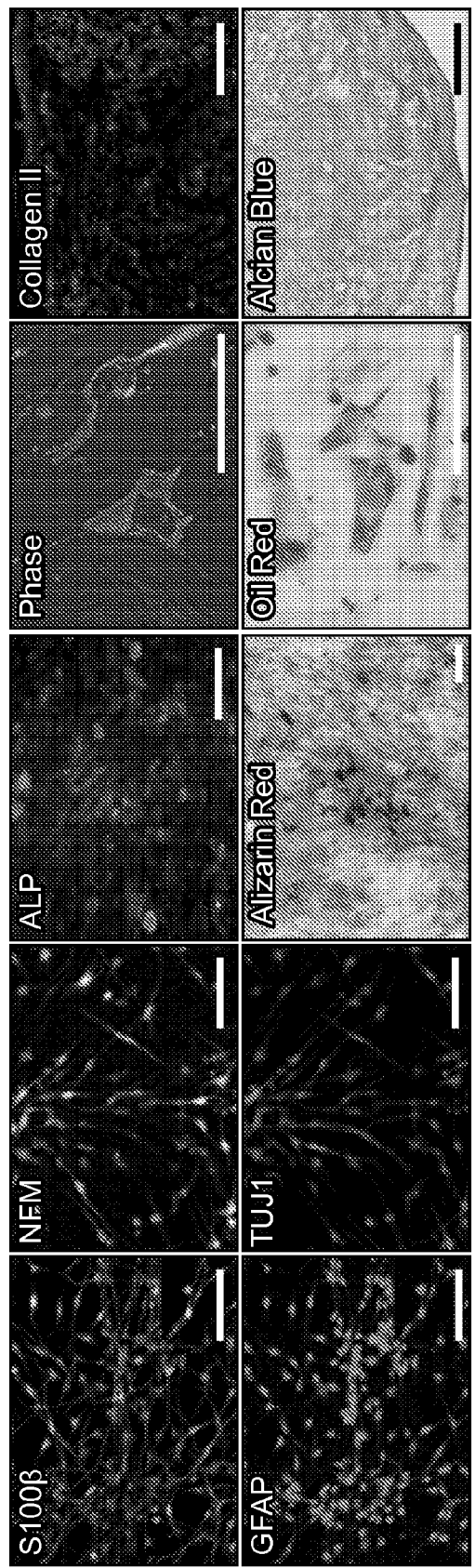
FIG. 2 shows directed differentiation of C-mpSCs. Differentiation into Schwann cells confirmed by S100β and GFAP immunostaining, into neuron-like cells by NFM and TUJ1 immunostaining Osteogenic differentiation confirmed by ALP immunostaining and Alizarin Red staining, adipogenic differentiation by phase contrast and Oil Red imaging, and chondrogenic differentiation by collagen II immunostaining and Alcian Blue staining, (images reproduced in gray-scale). Scale bars=100 µm

Multipotency assays showed that early gestation C-mpSCs can differentiate into mesodermal (osteogenic, adipogenic and chondrogneic) and ectodermal (Schwann cell-like and neuron-like cells) lineages (FIG. 2).

Figure 3:
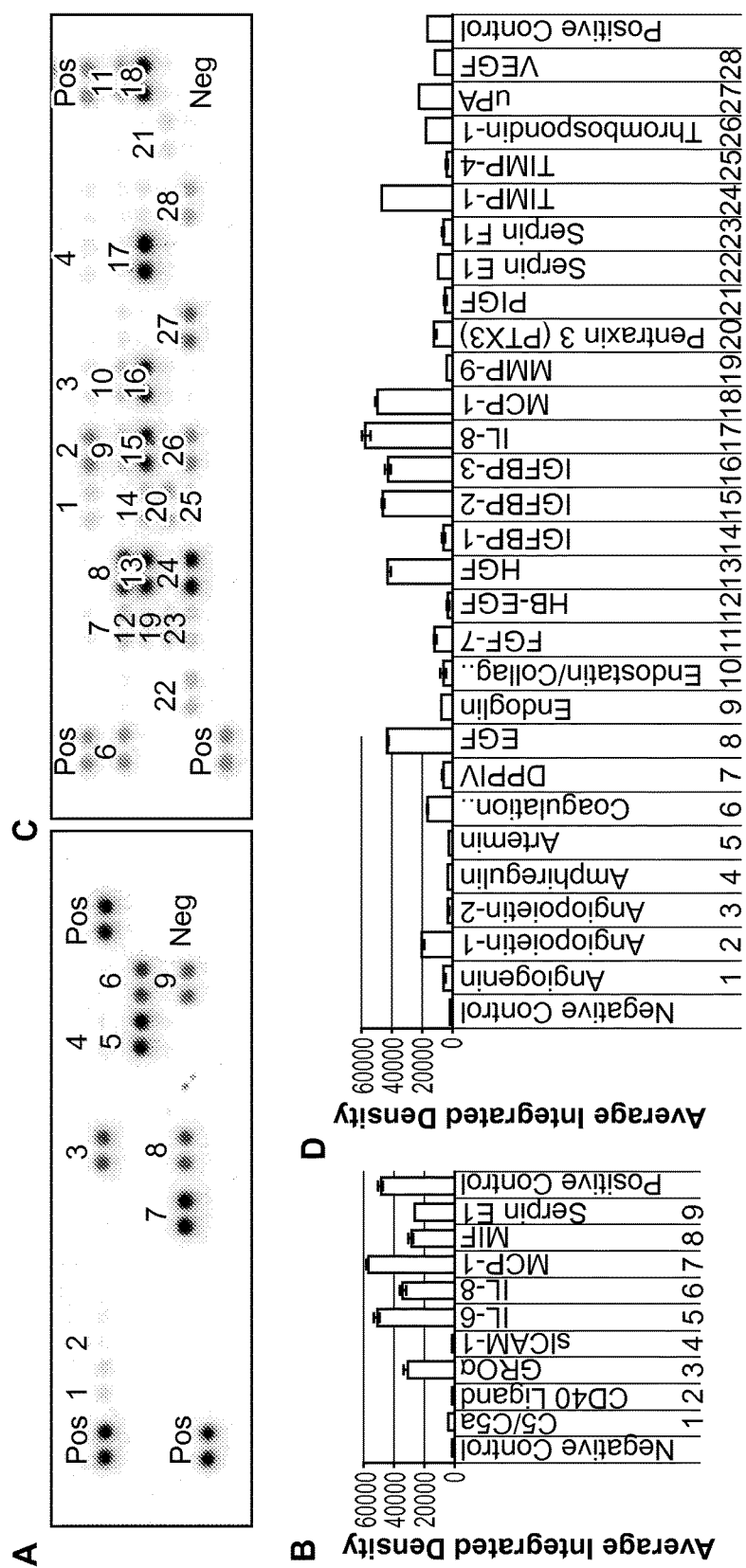
FIGS. 3A-3D show detection of secreted cytokines using the Panel A human cytokine array kit (A, B) and numerous immunomodulatory and chemotactic cytokines such as GROα, IL-6, IL-8, MCP-1, and MIF-1, as well as cytokines important for ECM remodeling such as Serpin E1. Cytokines detected by human angiogenesis array (C, D) included several immunomodulatory and angiogenic cytokines such as Angiogenin, Angiopoietin-1, HGF, IL-8, MCP-1, PTX3, TIMP-1, Thrombospondin-1, and VEGF.

Cytokine array assays showed that human C-mpSCs express angiogenic and immunomodulatory cytokines, e.g. Angiogenin, Angiopoietin-1, HGF, VEGF, IL-8, MCP-1, uPA (FIG. 3). The presence of these cytokines in the supernatant of C-mpSC cultures indicates that C-mpSCs may act via a paracrine mechanism to regenerate local tissue. To facilitate the identification of human C-mpSCs in in vivo models, Applicants transduced C-mpSCs with Green Fluorescent Protein (GFP) and luciferase using a lentiviral vector as described previously (Dull, T. et al. (1998) Journal of Virology 72:8463-8471), and demonstrated that transduced C-mpSCs are viable in 3D collagen. Thus, this disclosure also provides the isolated cells comprising a detectable label, e.g., GFP, or a non-native polynucleotide.

Figure 4:
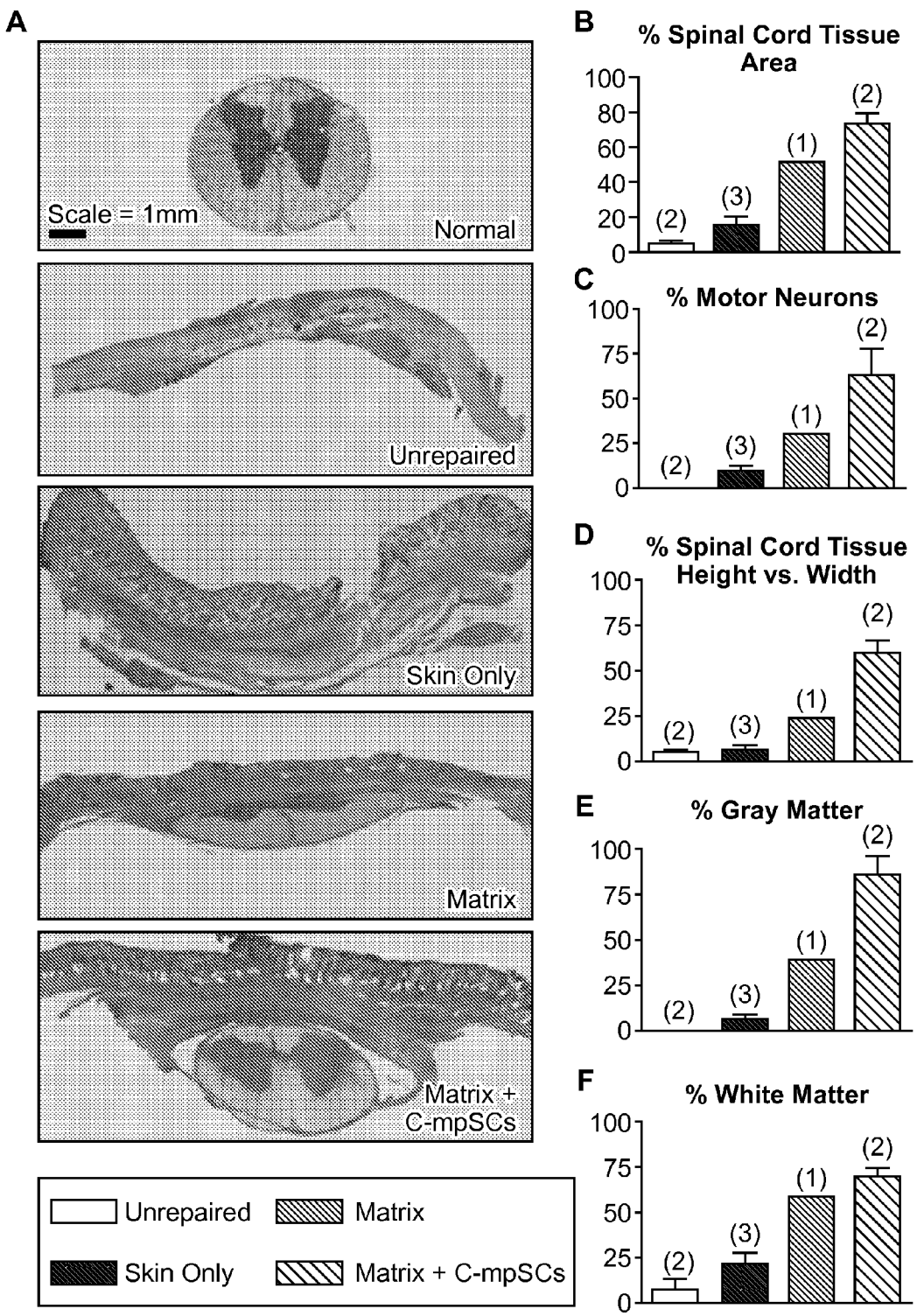
FIGS. 4A-4F show staining of spinal cord cross section. (A) Hematoxylin and Eosin staining of spinal cord cross sections at the level of the lesion in normal, unrepaired MMC, MMC skin-only repaired, MMC matrix-repaired and MMC matrix+C-mpSCs-repaired lambs highlight improved preservation of spinal cord tissue and morphology in C-mpSC treated lambs. Quantifications of spinal cord tissue area (B) and percent tissue area composed of gray and white matter (E, F) normalized to normal spinal cord tissue demonstrate increased preservation of all tissue in lambs treated with C-mpSCs, with particular gains in the preservation of grey matter. (D) Normalized quantification of spinal cord tissue height vs. width demonstrates that the thinning of the spinal cord associated with in utero trauma is substantially lessened in C-mpSC treated lambs compared to controls. (C) Similar improvements in the retention of motor neurons (identified by Cresyl Violet staining) are found in C-mpSC treated lambs compared to controls.

Applicants then extended their in vitro work into the well-accepted fetal lamb model of MMC. Applicants surgically created the MMC defect in fetal lambs at gestational age (GA) 75, as described previously (von Koch, C. S. et al. (2005) American Journal of Obstetrics and Gynecology 193(4):1456-1462; Meuli, M. et al. (1995) J. Pediatr. Surg. 30:1028-1033). Applicants repaired the defect at approximately GA-100, treating lambs as controls (e.g. no repair, closure of the skin only over the defect, collagen gel+ commercial ECM scaffold, autologous amnion patch) or with C-mpSC products (e.g. collagen gel+commercial ECM scaffold+C-mpSCs, collagen gel+autologous amnion patch+ C-mpSCs). All control lambs could not stand and did not exhibit normal hind limb motor reflexes. Remarkably, lambs repaired with C-mpSCs could stand, walk, run, and feed normally, and exhibited motor reflexes indistinguishable from those seen in lambs without MMC. Histopathological staining demonstrated dramatically improved retention of neural tissue area and motor neuron count in lambs treated with C-mpSCs (FIG. 4). The markedly increased preservation of grey matter in C-mpSC treated lambs is of particular interest in light of recent attention to the previously underrecognized importance of regenerating grey matter during spinal cord repair (Reier, P. J. (2004) NeuroRx: The Journal of the American Society for Experimental NeuroTherapeutics 1:424-451). Importantly, similarly improved motor function and spinal cord histopathology was observed in lambs treated with C-mpSCs and two different delivery vehicles (amnion and commercial ECM patches), supporting the role of C-mpSCs as the critical factor mediating the improvement in paralysis.

In Vivo Behavioral Data and Gross Histology
Isolation of Adherent Cell Populations from Placental and Bone Marrow Tissues:

All placental tissue was collected from routine procedures at UC Davis Medical Center in Sacramento, Calif. Placental tissues collected include term placenta from routine births, and pre-term placentas of gestational age 12-20 weeks from terminated pregnancies. Bone marrow was collected from discarded tissue from a lower limb amputation at the Sacramento Va. Hospital in Mather, Calif.

For explant culture, placental tissue was dissected and washed in sterile 1× phosphate-buffered saline (Hyclone) containing 1% penicillin-streptomycin (Invitrogen). Dissected tissue was then further cut into small pieces (<1 cm in width) and spread evenly across adherent cell culture dishes that were previously coated with CELLStart xeno-free substrate (Invitrogen) for 1 hour at 37° C. After 3-4 weeks adherent cells were harvested with TrypLE (Invitrogen) and passaged to a monolayer, and on subsequent passages were collected for immunostaining, differentiation, and other experiments detailed here.

Cells from chorionic villus tissue were also isolated by enzymatic dissociation of placenta tissue. For enzymatic dissociation, villus tissue was cut into small (1-2 cm) pieces and dissociated in a solution of 1 mg/mL collagenase IV (Sigma-Aldrich) in DMEM in a 37° C. incubator/shaker at 175 rpm for 30 minutes. Tissue was then mechanically dissociated by vigorous pipetting, and the suspension passed through a 100 μm nylon cell strainer. The filtered cell suspension was then centrifuged at 1700 rpm for 7 minutes, counted using a hemacytometer with Trypan Blue (Fisher Scientific) and then plated on adherent CELLstart coated dishes. Media was changed the following day to wash away any RBCs, tissue debris, dead and non-adherent cells. Cells were passaged upon 80-90% confluence and on subsequent passages were collected for immunostaining, differentiation, and other experiments detailed here.

Bone marrow MSCs were obtained by placing bone marrow aspirate on tissue culture-treaded plates in a low volume (3 mL) of cell culture media. After one week, tissue debris was removed and media replaced, leaving adherent MSCs. Bone marrow MSCs were then passaged upon confluence and collected for experimentation upon subsequent passages.

Culture media for all cells contained DMEM with 5% HyClone FBS (characterized) supplemented with 20 ng/mL recombinant human epidermal growth factor (Peprotech) and 20 ng/mL recombinant human fibroblast growth factor-basic (Peprotech) as well as 1% penicillin-streptomycin and 1% L-glutamine (Invitrogen).

Cell Growth-rate Analysis from CVS-size Tissue Samples:
Cell growth curves were generated from pre-term pMSCs by both explant and enzyme dissociation isolation methods in order to test the feasibility of obtaining cells from very small tissue samples within a relevant timeframe. For explant culture, preterm villus tissue was carefully dissected and washed in sterile IX PBS containing 1% penicillin-streptomycin. Dissected tissue was then further cut into smaller pieces (20-60 mg) analogous to the amount of tissue obtained in routine chorionic villus sampling (CVS). The CVS-size samples were then again dissected into smaller pieces and spread evenly across adherent E-well cell culture plates that were previously coated with CELLStart xeno-free substrate for 1 hour at 37° C. When cells reached 70-80% confluence, individual wells were passaged to 60 mm dishes and counted using a hemacytometer with Trypan Blue. Cells were counted at each subsequent passage until the third passage.

For enzymatically dissociated culture, pre-term chorionic villus tissue was dissected and washed in sterile IX PBS containing 1% penicillin-streptomycin. Dissected tissue was then further cut into smaller masses analogous to the amount of tissue obtained in routine chorionic villus sampling (CVS). The CVS-size tissue was then dissociated in a solution containing 1 mg/mL collagenase IV (Sigma-Aldrich) in a 37° C. incubator/shaker at 175 rpm for 30 minutes. Tissue was then mechanically dissociated by vigorous pi petting, and the suspension strained through a 100 μm nylon cell strainer. The filtered cell suspension was then centrifuged at 1700 rpm for 7 minutes, and plated on 35 mm tissue culture-treated CELLstart coated dishes. Media was changed the following day to wash away any RBCs, tissue debris, and non-adherent cells. When adherent cells grew to 70-80% confluence they were passaged to 60 mm dishes and counted using a hemacytometer with Trypan Blue. Cells were counted at each subsequent passage until the third passage.

Immunophenotyping of Placenta and Bone Marrow MSCs by Flow Cytometry:

Flow cytometry was performed using a BD Fortessa LSR Cell Analyzer. Cells were harvested using Accutase (Invitrogen), centrifuged and counted using a hemacytometer and Trypan Blue. Samples were split into fractions with roughly $1\times10^6$ cells each and stained with various antibodies for analysis. Cells were analyzed for several neural, hematopoietic, mesenchymal, and other surface markers. Neural-related markers include CD56 (PE, Biolegends, 39D5), CD271 (AlexaFluor 647), CD57 (FITC), and 15 (PE), and well-established MSC surface markers CD44 (FITC), CD90 (PE-cy5), CD73 (PE), and CD105 (AlexaFluor 647) were also examined. Additionally, cells were stained for hematopoietic and endothelial cell markers CD34 (PE), CD45 (FITC), and CD31 (AlexaFluor 647) as well as integrins CD29 (PE), CD49f (AlexaFluor 647), CD49d (PE) and the chemokine receptor CD184 (PE-cy5). All antibodies used (with the exception of CD56) were purchased from BD Pharmingen.

Dead cells were identified and removed from analysis usmg LIVE/DEAD® Fixable Aqua Dead Cell Stain Kit (Molecular Probes). Cells were fixed for 30 minutes in 4% paraformaldehyde after staining, prior to data collection. Software analysis of collected data was performed using the software program FlowJo by Treestar, Inc.

Identification of Neural-related Proteins by Immunocytochemistry:

For all immunostaining, samples were fixed in 4% paraformaldehyde in PBS for 15 minutes, followed by membrane permeabilization with 0.5% Triton X-100 in PBS for 10 minutes. The cells were then incubated with the primary antibodies for 2 hours, and then with AlexaFluor 488 or AlexaFluor 546—conjugated secondary antibodies for 1 hour. Cell nuclei were then counterstained with DAPI for 5 minutes. Images were collected at 100, 200, or 400× magnification using a Zeiss fluorescence microscope.

Undifferentiated PMSCs were stained with antibodies for neural-related proteins including Nestin (Millipore), Neurofilament medium (Sigma Aldrich), and Schwarm cell marker S100β (Sigma Aldrich). In addition, cells were also stained with antibodies for stem cell transcription factors related to neural development, migration, and angiogenesis including Sox2 (R&D Systems), Sox10 (Sigma-Aldrich), Sox17 (R&D Systems), Snail (Santa Cruz Biotech), and Slug (Santa Cruz Biotech). Multinucleated cells discovered in pre-term pMSC cultures were examined for their expression of NCAM/CD56 (Sigma Aldrich), p75/CD271 (Abeam), Nestin, NFM, and S100β.

Targeted Induction of Cells into Ectodermal and Mesodermal Phenotypes:

To induce differentiation into neurons, cells were cultured in DMEM F12 media supplemented with N2 (Invitrogen), 10 ng/mL BDNF (Peprotech), 10 ng/mL NGF (R&D Systems), 10 ng/mL GDNF (Peprotech) and 1 mM dibutyryl-cAMP (Sigma-Aldrich) for at least 2 weeks. Cells were then fixed in 4% paraformaldehyde and immunostained with NFM (Sigma Aldrich) and Tuj 1 (Covance) to assess successful differentiation into neurons.

To induce differentiation into Schwann cells, cells were cultured in DMEM F12 supplemented with N2, 10 ng/mL CNTF (Peprotech), 10 ng/mL bFGF, 20 ng/mL heregulin β-1 (Peprotech) and 1 mM dibutyryl-cAMP for 2-3 weeks. Cells were then fixed in 4% paraformaldehyde and immunostained for GFAP (Millipore) and S100β (Sigma-Aldrich) to assess successful differentiation in Schwann cells.

To induce osteogenic differentiation, cells were grown to confluence and cultured for 2-3 weeks in DMEM medium containing 10% fetal bovine serum (FBS), 10 mM β-glycerol phosphate (Sigma Aldrich), 0.1 μM dexamethasone (Sigma Aldrich) and 200 μM ascorbic acid (Sigma Aldrich). Cells were then fixed in 4% paraformaldehyde and stained with Alizarin Red (Sigma-Aldrich) to identify calcified matrix, and immunostained for alkaline phosphatase (R&D Systems) to identify osteogenesis.

To induce adipogenic differentiation, cells were grown to 70% confluence and media changed to StemPro® Adipogenesis Differentiation media (Invitrogen) for 3-4 weeks. Phase contrast images were collected, and cells were then fixed in 4% paraformaldehyde and stained with Oil Red 0 (Sigma-Aldrich) for lipids and fat.

To induce chondrogenic differentiation, cells were cultured as cell pellets (<1 mm in diameter) in suspension for 3 weeks in StemMACS ChondroDiff Media (Miltenyi). The pellets were then fixed in 4% paraformaldehyde for 20 minutes and embedded in OCT compound (Fisher Scientific) before being cryosectioned. The sections of the pellets were then immunostained for collagen II (Abeam) and stained for glycosaminoglycans by using Alcian Blue (Sigma-Aldrich).

Array Analysis of Secreted Cytokines from Placenta MSCs:

To identify any potential paracrine effects that pMSCs could have on other cells in their immediate environment, cytokines in the supernatants of three pMSC cultures (term and pre-term explant, and pre-term enzyme dissociated) were analyzed using two cytokine array kits: (1) Human Cytokine Array Panel A and (2) Human Angiogenesis Antibody Array (R&D Systems ARY005 & ARY007, respectively). Cells were seeded at a density of $7.5\times10^5$ per 100 mm culture dish and after 4 days supernatant was collected, centrifuged to remove particulates and then assay performed according to manufactures instructions. Data collected was analyzed using ImageJ analysis software and plotted using Microsoft Excel.

Figure 5:
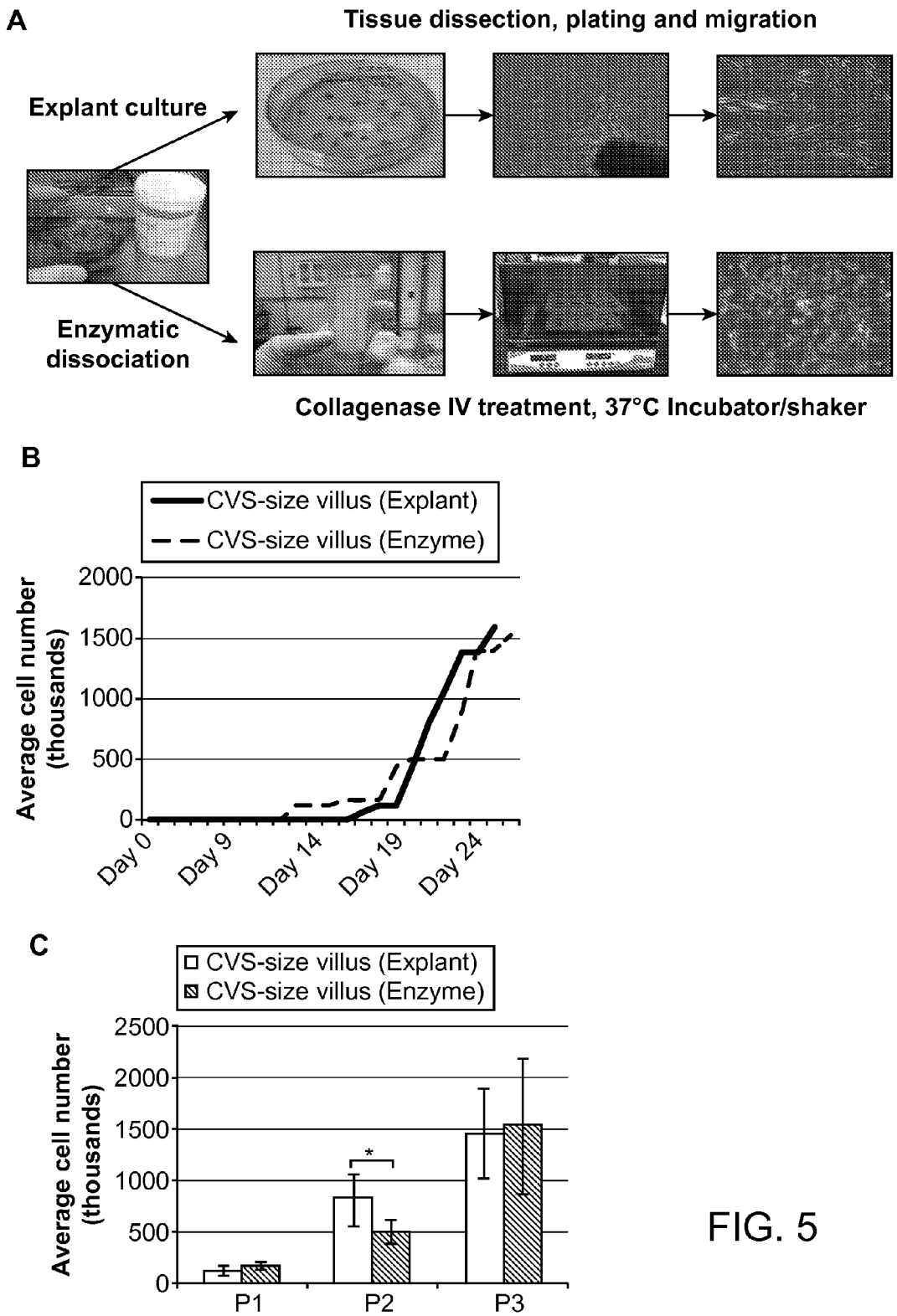
FIGS. 5A-5C show placental MSCs obtained from CVS-size tissues less than 4 weeks. Cell growth-rate analysis of pMSCs obtained from pre-term, CVS-size villus tissue samples (A) were isolated by two methods: tissue explant culture (n=12), and enzymatic dissociation (n=4). (B) Averages of cell counts over the observed time period and (C) average cell numbers at each passage. Bars show standard deviation, *p-value<0.01; calculated by t-test.

Results
Placental MSCs Obtained from CVS-size Tissues Less Than 4 Weeks:

Mesenchymal stem cells were isolated from pre-term chorionic villus tissue using two methods. The isolation methods assessed were traditional explant culture and enzymatic dissociation of tissue using collagenase IV (FIG. 5A). CVS-size (20-60 mg) tissue samples were dissected from pre-term placenta and cells cultured using both methods independently to assess the time needed to obtain viable, growing cells. The data suggests that the resulting cell growth was quite similar between isolation methods and cells from both methods reached the third passage within a 26 day period (FIGS. 5B and 5C). Cell counts at the second passage were found to be significantly different between isolation methods (n=12 explant, n=4 enzyme dissociated, analyzed by t-test, *p-value<0.01), but were not by the statistically different by the third passage.

Regardless of the isolation method, over $10^6$ cells could be obtained reliably by the third passage somewhere before 4 weeks for either method, even from tissue samples as small as 20 mg.

Immunophenotyping by Flow Cytometry Reveals Typical MSC Profile:

Flow cytometry immunophenotyping was conducted using pre-term pMSCs (from explant and enzymatic dissociation), term pMSCs (from explant), and bone marrow MSCs. Each cell population was stained with pre-conjugated antibodies for 15 surface markers and results from each cell type were found to be quite similar (FIG. 6A). In general, all groups were all or mostly positive for known MSC markers CD73, CD44, CD90, and CD105, integrins CD29, CD49d and CD49f, as well as chemokine receptor CD184. Conversely, all groups were found all or mostly negative for CD15, CD57, and hematopoietic and endothelial markers CD34, CD45, and CD31. Expression of integrin CD49f varied between groups, with at least some if not most cells expressing it.

Figure 6:
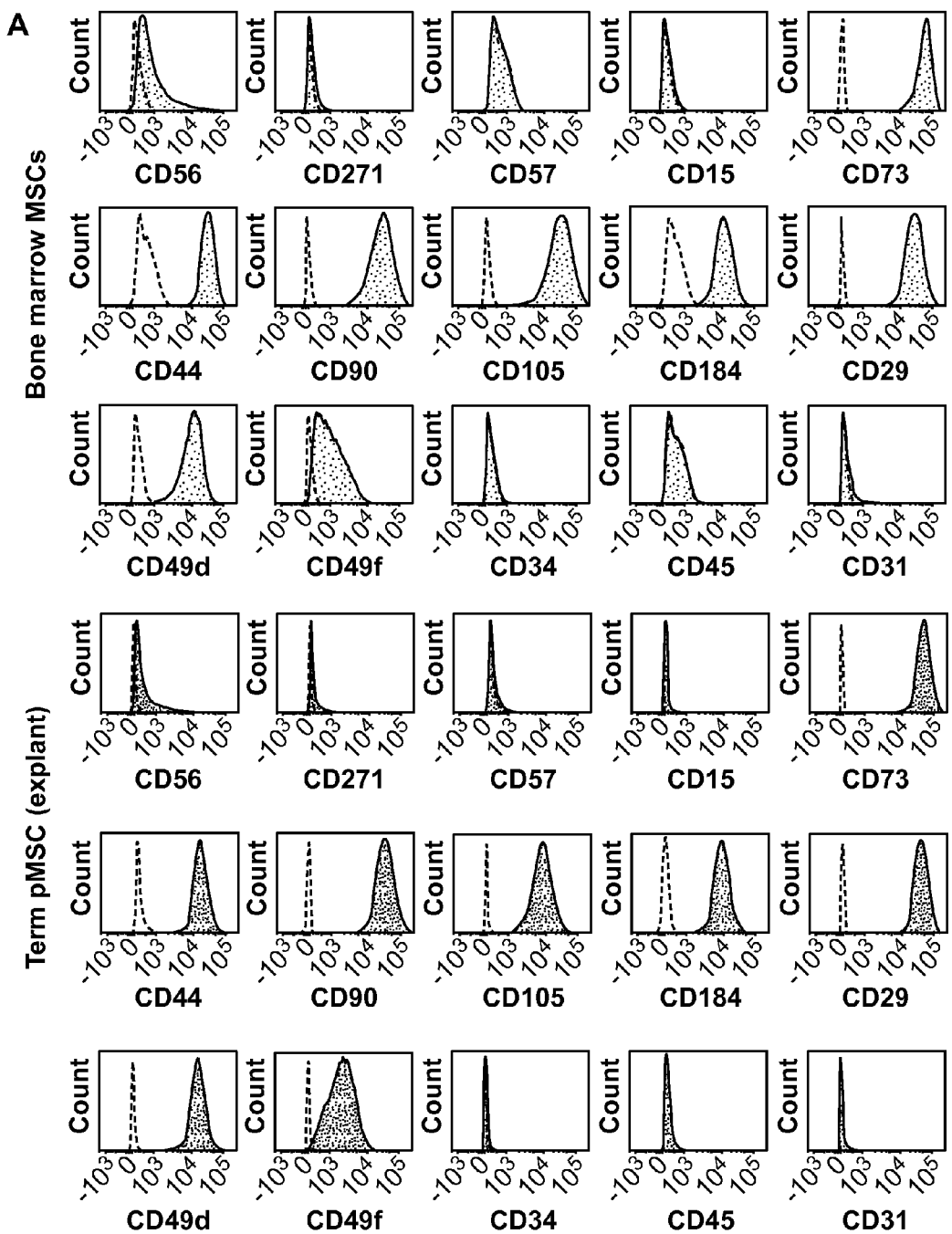
FIGS. 6A-6B depict flow cytometry immunophenotyping revealing MSC profile. (A) Analysis of 15 surface markers by flow cytometry in four cell populations: bone marrow MSCs, term pMSCs (from explant), pre-term pMSCs (from explant), and pre-term pMSCs (from enzymatic dissociation). (B) Bivariate plots show coexpression of CD56 and CD271 in each cell population analyzed.

CD56 and CD271 Expression/Coexpression:

All four cell groups had populations of cells positive for CD56 (24-30%) and CD271 (4-17%), with bone marrow MSCs having the highest percentage of cells expressing CD56 (~30%) and pre-term pMSCs from explant culture having the most cells expressing CD271 (~17%) (FIGS. 2A and 2B). Additionally, a double positive subset was observed in all four groups and ranged from ~4-16% (FIG. 6).

Figure 7:
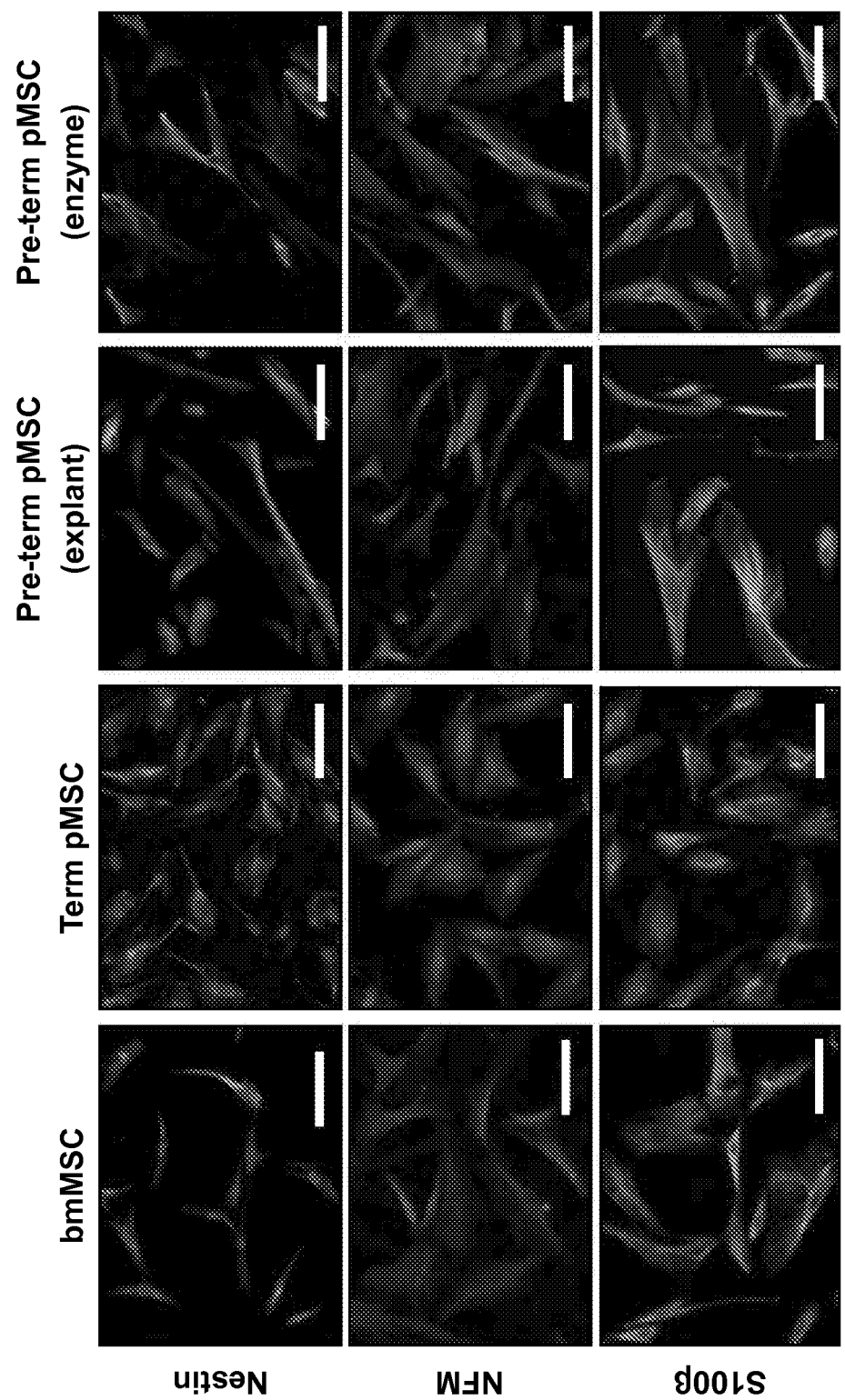
FIG. 7 depicts analysis of intraceullar proteins by immunocytochemistry. Immunostaining of intracellular neural-related markers in undifferentiated bone marrow, term (via explant), and pre-term (via explant and enzyme dissociation) pMSCs. Cells were stained for intermediate filament protein Nestin, Neurofilament medium (NFM), Schwann cell marker S100β and counterstained with DAPI in blue, (shown in gray-scale). Scale bar=100 μm.

Analysis of Neural-Related Proteins and Transcription Factors by Immunocytochemistry:

Undifferentiated pre-term pMSCs obtained from both isolation methods along with term pMSCs (explant) and bone marrow MSCs were analyzed for neural-related proteins and transcription factors using immunocytochemistry. All four cell groups stained positively for two neural-related filament proteins: Nestin, and Neurofilament medium (NFM), as well as the Schwann cell-associated protein S100β (FIG. 7).

Figure 8:
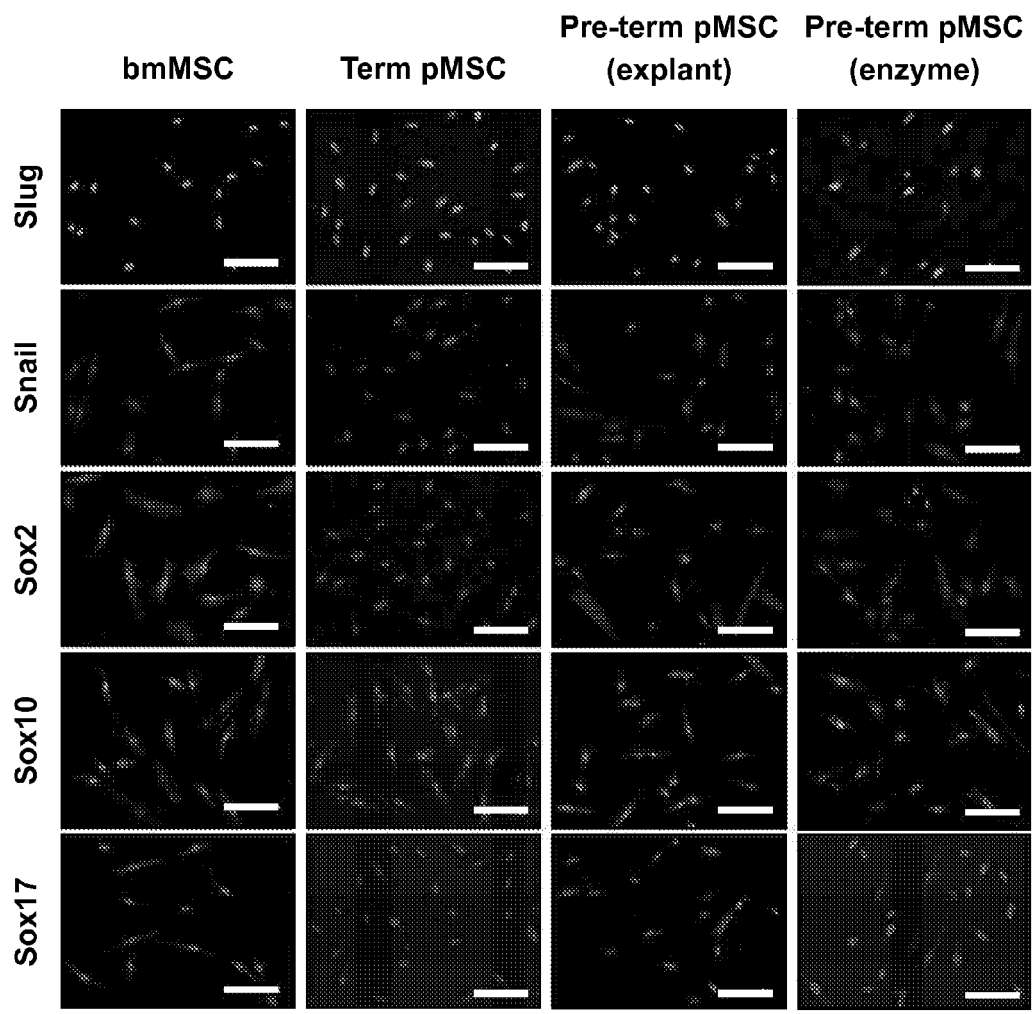
FIG. 8 shows analysis of transcription factors by immunocytochemistry. Immunostaining analysis for various transcription factors in bone marrow, term (via explant), and preterm (via explant and enzyme dissociation) pMSCs. Cells were stained for transcription factors Slug, Snail, Sox2, Sox10, and Sox17 and nuclei counterstained with DAPI in blue, (shown in gray-scale). Scale bar=100 μm.

Additionally, transcription factors related to neurogenesis, migration, and angiogenesis were also examined using immunocytochemistry (FIG. 8). All four undifferentiated cell types expressed the transcription repressor Slug and neural crest migration-associated transcription factor Sox10. Pre-term pMSCs and bone marrow MSCs expressed the transcriptional repressor Snail, although it was found to be lacking in term pMSCs. As well, term pMSCs lacked Sox2 expression and showed very dim staining of Sox17 where the other three cell types were observed positive for both.

Differentiation into Ectodermal and Mesodermal Lineages:

Capacity of pre-term enzyme dissociated pMSCs towards differentiation into ectodermal and mesodermal lineages was assessed alongside term pMSCs and bone marrow MSCs (FIGS. 9A and 9B). All three cell populations were also capable of differentiation into ectodermal phenotypes including Schwann cells and neurons (FIG. 9A). In Applicants' experiment, bone marrow MSCs appeared to progress much slower towards ectodermal lineages and, in fact, many cells did not differentiate at all. With term and pre-term villus MSCs, most cells took on morphological characteristics of neural and Schwann cells and were positive for immunostaining markers TUJ1 and NFM for neurons and S100β and GFAP for Schwann cells.

All three cell groups also showed ability to generate cells of the mesodermal lineages (FIG. 9B). Osteogenic differentiation was verified by positive immunostaining for alkaline phosphatase and by staining calcium deposition with Alizarin Red. Additionally, all three cell groups displayed positive Oil Red staining for adipogenic differentiation and positive Alcian blue and collagen II staining for chondrogenic differentiation. Bone marrow MSCs driven to adipogenic differentiation generated lipid bubbles that were slightly larger than the placenta samples, but aside from this differentiation capacity toward mesodermal lineages was very similar between samples.

Figure 10:
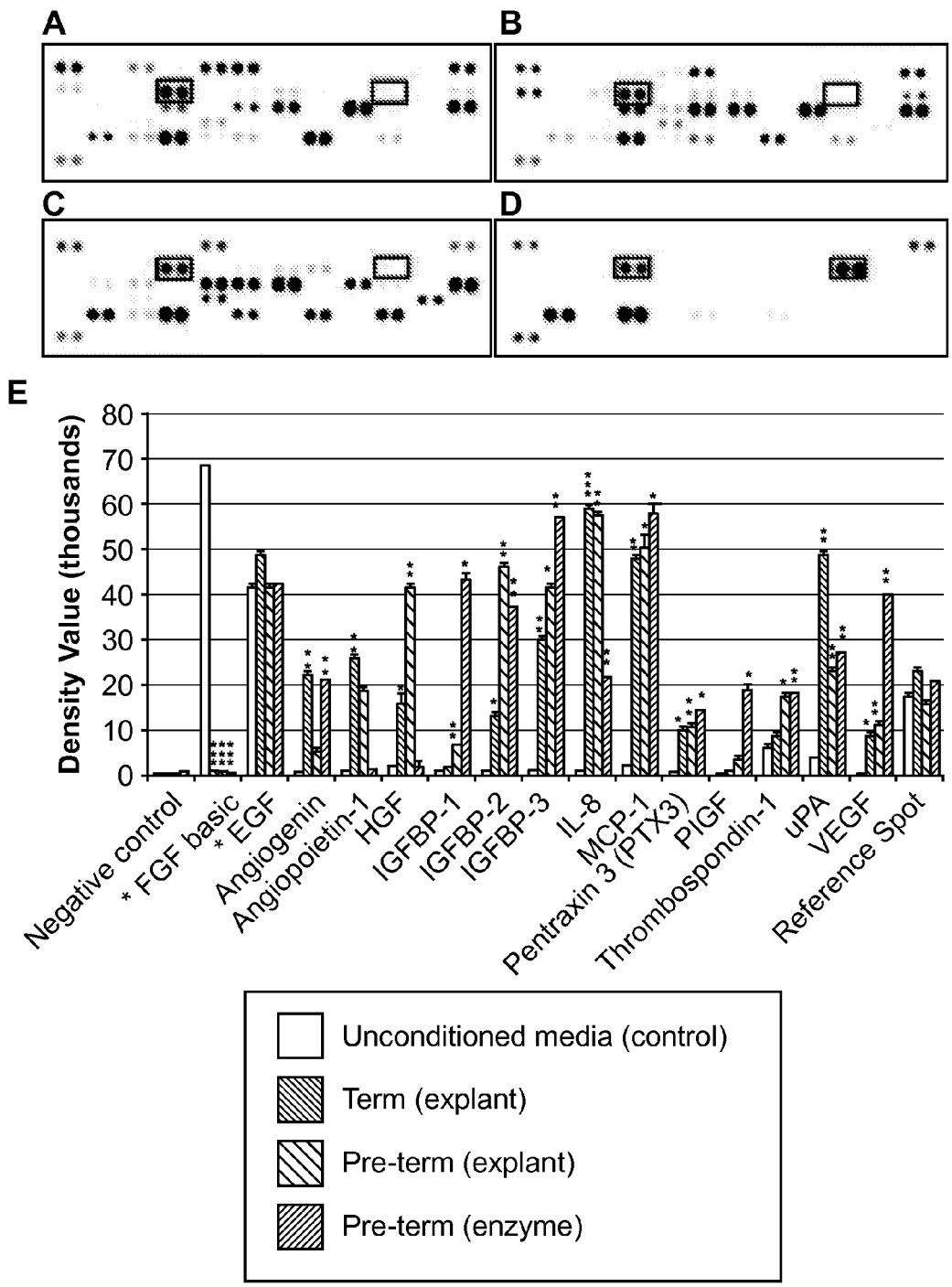
FIGS. 10A-10E show secreted cytokines detected by Human Angiogenesis array. (A-D) Results of angiogenesis array including original images of original array membranes. Blue boxes denote spots on the membranes representing epidermal growth factor (EGF) and red boxes denote spots for basic fibroblast growth factor (bFGF), (shown in gray-scale). (E) Integrated density measurement for selected cytokines detected in the supernatant of all or some of the cell populations at a level above that of the unconditioned media. Asterisks denote media components EGF and bFGF, respectively. Error bars show standard deviation. *p-value<0.05, * *p-value<0.01, * * *p-value<0.001; analyzed by t-test against unconditioned media.

Secretion of Angiogenic and Immunomodulatory Cytokines Detected by Array:

Supernatants of pre-term PMSCs from both isolation methods and term PMSCs were collected and secreted cytokines were analyzed using two cytokine array kits which combined are capable of probing for over 70 cytokines Negative controls using unconditioned cell culture media were also set up to determine any bias that could be introduced by the culture media and its supplements. Chemiluminescence was observed on original membranes incubated with supernatant from each sample using both arrays (FIGS. 10A-10D, 11A-11D). In the human angiogenesis array, many of the 55 cytokines detectable on the array membrane were present to some degree in Applicants' three cell samples, but not the media control. The array detected high levels of bFGF, EGF, TIMP-1, and Serpin E1 in the unconditioned media serving as Applicants' negative control. bFGF and EGF are components of Applicants' standard culture media, and their membrane spots are highlighted by red and blue rectangles and their positions on the accompanying graph by red and blue asterisks (converted to black & white, see FIG. 10). Interestingly, bFGF was detected at a high level in the unconditioned media sample but not in any of the cell supernatant samples, indicating that these cells were taking up bFGF and that within 4 days they were capable of depleting 20 ng/mL of the cytokine. At the same time, EGF levels remained constant in all four samples. An additional 13 cytokines detected in cell supernatant samples were found at levels significantly above that of the unconditioned media control (FIG. 10E). Those detected at levels significantly above unconditioned media controls include Angiogenin, Angiopoietin-1, HGF, IGFBP-1, IGFBP-2, IGFBP-3, IL-8, MCP-1, PTX3, P1GF, Thrombospondin-1, uPA, and VEGF.

Figure 11:
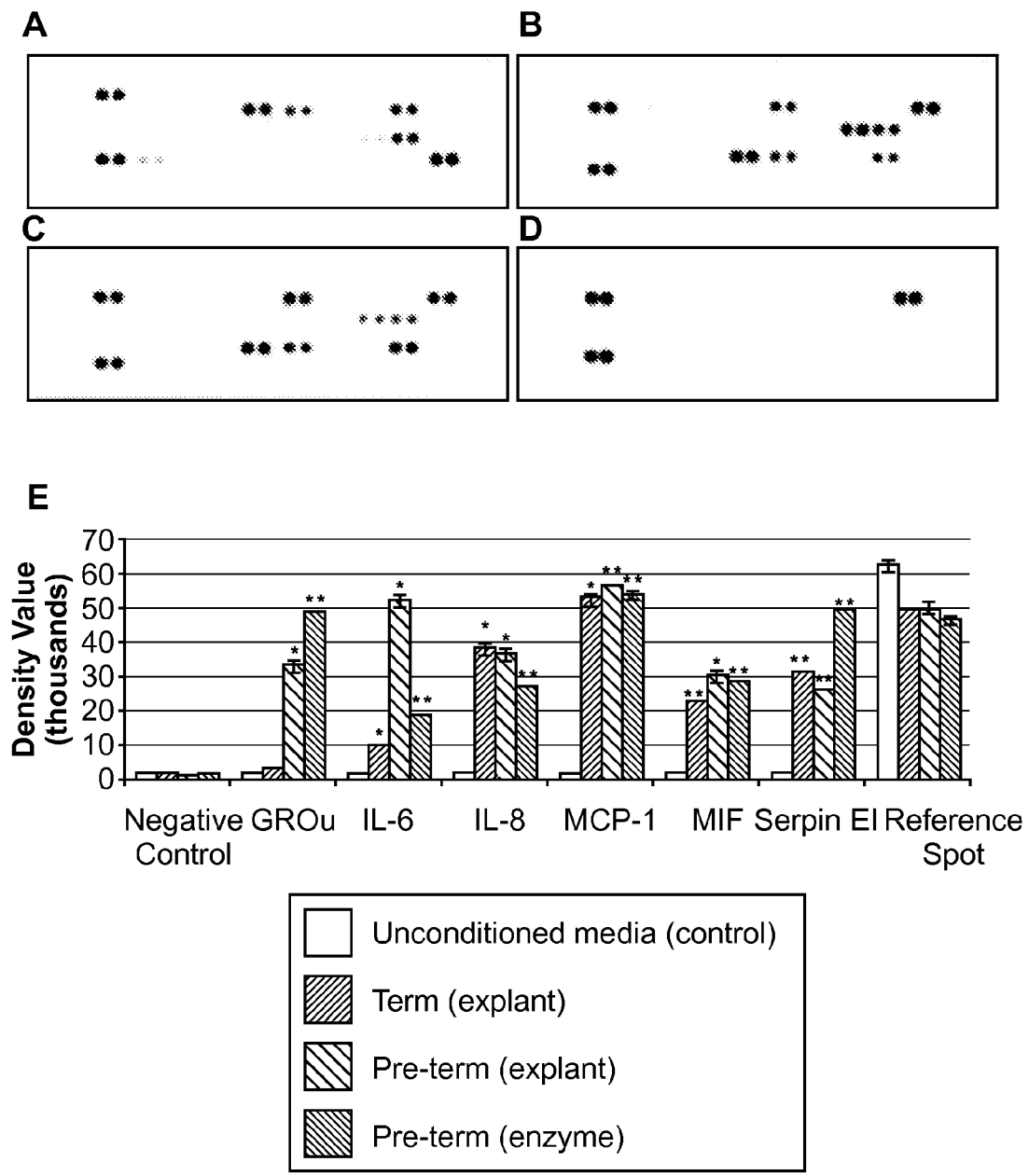
FIGS. 11A-11E show secreted cytokines detected by Human Panel A array. (A-D) Results of human proteome profiler array including images of original membranes. (E) Side-by-side comparisons of integrated density measurements of 6 cytokines (GROα, IL-6, IL-8, MCP-1, MIF, and Serpin E1) detected in the supernatant of all or some of the cell population at a level above that of the unconditioned media. Error bars represent standard deviation, *p-value<0.05, **p-value<0.01; analyzed by t-test against unconditioned media.

The Panel A human cytokine array is capable of detecting less cytokines than the angiogenesis array (36 in total), but contains several cytokines important for cell functions such as proliferation, migration and inflammation that are absent from the angiogenesis array. All three cell types were found to have significantly increased secretion of five cytokines detected at much lower levels in the control: GROα, IL-6, IL-8, MCP-1, MIF, and Serpin E1 (FIG. 11E). GROα is the one exception in that while it was detected in the supernatant of both pre-term pMSC groups, it was largely absent from the term pMSC supernatant. MCP-1 was the most intensely detected cytokine in all three cell groups, and IL-6 secretion was found to be much higher in the pre-term pMSCs from explant culture than the other two groups.

Discovery of Novel Multinucleated Cells Positive for NCAM and p75:

Discussion

Pre-term chorionic villus tissue is a unique cell source capable of yielding robust multipotent MSCs well-suited for autologous in utero cell therapy. Pre-term pMSCs isolated from CVS-size samples using both explant culture and enzyme dissociation were consistently able to achieve populations on the order of $10^6$ cells in less than 4 weeks, indicating that both methods are feasible means of obtaining cells for an autologous fetal cell therapy. With in utero MMC repair in humans typically occurring before 26 weeks gestational age, Applicants' data shows that CVS tissue obtained late in the first-trimester could conceivably produce cell populations with numbers in the order of $10^6$ cells in 4 weeks and which could likely be grown to $10^7$ before the repair would even be performed. Cell populations obtained from enzymatic dissociation culture morphologically appear to be varied and heterogeneous before the first passage. Despite this early discrepancy, fibroblast-like MSCs appear to dominate the cultures within three passages. Both methods are suitable to obtain healthy and viable cells in a relatively short period of time, and pMSCs remain excellent candidates for autologous in utero cell therapy.

Immunophenotyping by flow cytometry was employed to establish a surface marker profile and to determine that these cells are indeed MSCs. The CD56+ and CD271+ subsets made up variable proportions of the overall cell population for each cell group. Co-expression of these two markers was observed in all cell samples analyzed, possibly indicating some currently unknown relationship between them. Though any functional significance of these subsets is not known, this data indicates clearly that these subsets persist MSCs from both bone marrow and placenta tissue. Each cell population exhibited a similar surface marker phenotype generally associated with MSCs: positivity for well-established MSC markers CD73, CD44, CD90, and CD105 as well as integrin CD29 and cytokine receptor CD184 (CXCR4) while negative for hematopoietic and endothelial markers CD34, CD45, and CD31 as well as neural-related markers CD15 and CD57. This expression profile is typical of MSCs and was found in the populations examined here and confirmed the identification of these cells as MSCs.

Analysis of cells by immunocytochemistry demonstrated that pMSCs obtained from the different isolation methods shared a similar expression profile for transcription factors related to neurogenesis (Sox2, Slug and Snail), migration and development of the neural crest (Sox10), and angiogenesis (Sox17). Pre-term pMSCs in general were found to have a profile quite similar to that displayed by bone marrow and term pMSC (with the exception of some markers in term pMSCs such as Snail and Sox2). Sox2 is critical for maintenance of the neural phenotype. Researchers have recently shown that mouse and human fibroblasts can be reprogrammed directly to neural stem cells using Sox2 alone (Ring, K. L. et al. (2012) Cell Stem Cell 11(1):100-109). Slug and Snail are zinc-finger transcription factors which play significant roles in the development of the nervous system. Both are members of the Snail family of transcription repressors and are expressed in and related to the neural crest region during neural development (Vernon, A. E. et al. (2006) Development 133:3359-3370). Pre-term MSCs also expressed Sox10, a transcription factor believed to regulate multipotency and inhibit complete neural differentiation in neural progenitor cells (Kim, J. et al. (2003) Neuron 38(1): 17-31). Sox10 is also another key protein regulating neural crest development as well as peripheral glial cell development (Kelsh, R. N. (2006) Bioessays 28(8):788-798; Britsch, S. et al. (2001) Genes and Development 15:66-78). Interestingly, pre-term pMSCs also expressed Sox17, a transcription factor essential for the differentiation of ESCs during cardiac myogenesis and postnatal angiogenesis (Liu, Y. et al. (2007) Proceedings of the National Academy of Sciences of the United States of America 104(10):3859-3864; Matsui, T. et al. (2006) Journal of Cell Science 119:3513-3526). Sox17 expression could indicate a capacity of these cells to participate critical portions of wound repair such as neovascularization.

Pre-term pMSCs are multipotent, and can generate mature cells with mesodermal and ectodermal phenotypes. The plasticity of pre-term pMSCs illustrated here is comparable to that of bone marrow and term pMSCs, and they appear better suited to undergo ectodermal differentiation. Abundant differentiation of bone marrow MSCs into neural and Schwann phenotypes was not seen here; although previous reports have indicated that bone marrow MSCs are capable of differentiating into these lineages as well (Shea, G. K. H. et al. (2010) Experimental Neurology 224(2):448-458). External confounding variables related to the tissue donor's age or health may have affected the differentiation of these cells. In contrast, pre-term pMSCs appeared to readily differentiate into all lineages examined.

The human cytokine array assays were performed in order to gain insight into pMSC cytokine secretion, keeping in mind the proclivity of MSCs to affect their environment through paracrine signaling. The human angiogenesis array was able to identify several cytokines present in cell supernatants and not in the unconditioned media control such as Angiogenin, Angiopoietin-1, HGF, IGFBP-1, IGFBP-2, IGFBP-3, IL-8, MCP-1, P1GF, PTX3, Thrombospondin-1, uPA, and VEGF. These cytokines have a wide variety of functions, and are important in angiogenesis, immunomodulation, and wound repair and healing. Angiogenin, Angiopoietin-1, HGF, IL-8, P1GF, Thrombospondin-1 and VEGF are known to regulate angiogenesis among other effects (Park, J. E. et al. (1994) The Journal of Biological Chemistry 269(41):25646-25654; Lawler, J. (2002) Journal of Cellular and Molecular Medicine 6(1):1-12; Li, A. et al. (2003) Journal of Immunology 170(6):3369-3376; Kagiwada, H. et al. (2008) Journal of Tissue Engineering and Regenerative Medicine 2(4):184-189; Liu, X. H. et al. (2008) Microvascular Research 76(1):23-30; Soleymaninejadian, E. et al. (2011) American Journal of Reproductive Immunology 67:1-8; Liu, X. B. et al. (2012) Journal of Zhejian University Science 13(8):616-623). Thrombospondin-1, unlike the other cytokines listed here, is involved in the inhibition of angiogenesis and would suggest that these cells have the ability to not only induce, but to suppress angiogenesis (Lawler, J. et al. (2002) Journal of Cellular and Molecular Medicine 6(1):1-12). Placenta growth factor, or P1GF, is a member of the VEGF family of growth factors and has been shown to actually potentiate the action of lower concentrations of VEGF in vitro and in vivo (Park, J. E. et al. (1994) The Journal of Biological Chemistry 269(41): 25646-25654). Insulin-like growth factor (IGF) binding proteins IGFBP-1, IGFBP-2 and IGFBP-3 are carriers of IGF in circulating plasma and are found in tissues and fluid throughout the body (Rajaram, S. et al. (1997) Endocrine Reviews 18(6):801-831). IGFBP-2 also is a critical protein for triggering osteogenesis in bone marrow MSCs (Hamidouche, Z. et al. (2010) BMC Cell Biology 11(44):1-9). MCP-1, IL-8, and PTX3 are all involved in recruitment of cells in immune response and modulation of inflammation (Hoogduijn, M. J. et al. (2010) International Immunopharmacology; Boomsma, R. A. et al. (2012) PLoS ONE 7(4): e35685; Kunes, P. et al. (2012) Mediators of Inflammation 2012:1-10; Najar, M. et al. (2013) International Immunopharmacology). uPA, or urokinase-type plasminogen activor, is involved in signaling pathways crucial for ECM remodeling during cancer and inflammation (Smith, H. W. et al. (2010) Nature Reviews Molecular Cell Biology 11:23-36.). Detection of bFGF in the unconditioned media control but none of the cell samples indicates uptake of bFGF by cells with no replacement (secretion), while detection of EGF in all samples indicates either no uptake of EGF, or uptake of EGF with secreted replacement. Overall, secretion of these cytokines found here indicates the potential for pMSCs to aid in repair of damaged tissue and modulation of immune response and inflammation.

The Panel A human cytokine array detected secretion of 5 factors (GROα, IL-6, IL-8, Serpin E1, MIF, and MCP-1) that were secreted by pMSCs at levels significantly greater than detected in the unconditioned media control. Of particular interest are GROα and IL-6, which were observed secreted in greater quantity by preterm pMSCs than by term placental MSCs. GROα, or CXCL1, produces chemotactic activity while IL-6 is an interleukin that has both pro- and anti-inflammatory effects. IL-8, which was also detected in the angiogenesis array, has angiogenic and immunomodulatory effects (Li, A. et al. (2003) Journal of Immunology 170(6):3369-3376; Najar, M. et al. (2013) International Immunopharmacology). MCP-1 was the most highly secreted molecule for all 3 pMSC groups examined. MCP-1, or CCL2 is secreted in response to inflammatory processes, is known to induce migration in bone marrow MSCs and can have a "protective" effect on cells grown in hypoxic conditions (Boomsma, R. A. et al. (2012) PLoS ONE 7(4): e35685). MCP-1 expression could relate directly to MSC homing abilities and could enhance this effect in in vivo cell therapies. Serpin E1, an inhibitor of uPA, while not detected in the unconditioned media in this assay, was detected in that of the angiogenesis array assay and thus further investigation is necessary to assess the degree to which it is truly secreted by pMSCs. The wealth of information regarding cytokine secretion in pMSCs obtained here can be used as a basis for future in vitro and in vivo research directed at the secretion pattern of individual cytokines and the any observable paracrine effects.

Figure 12:
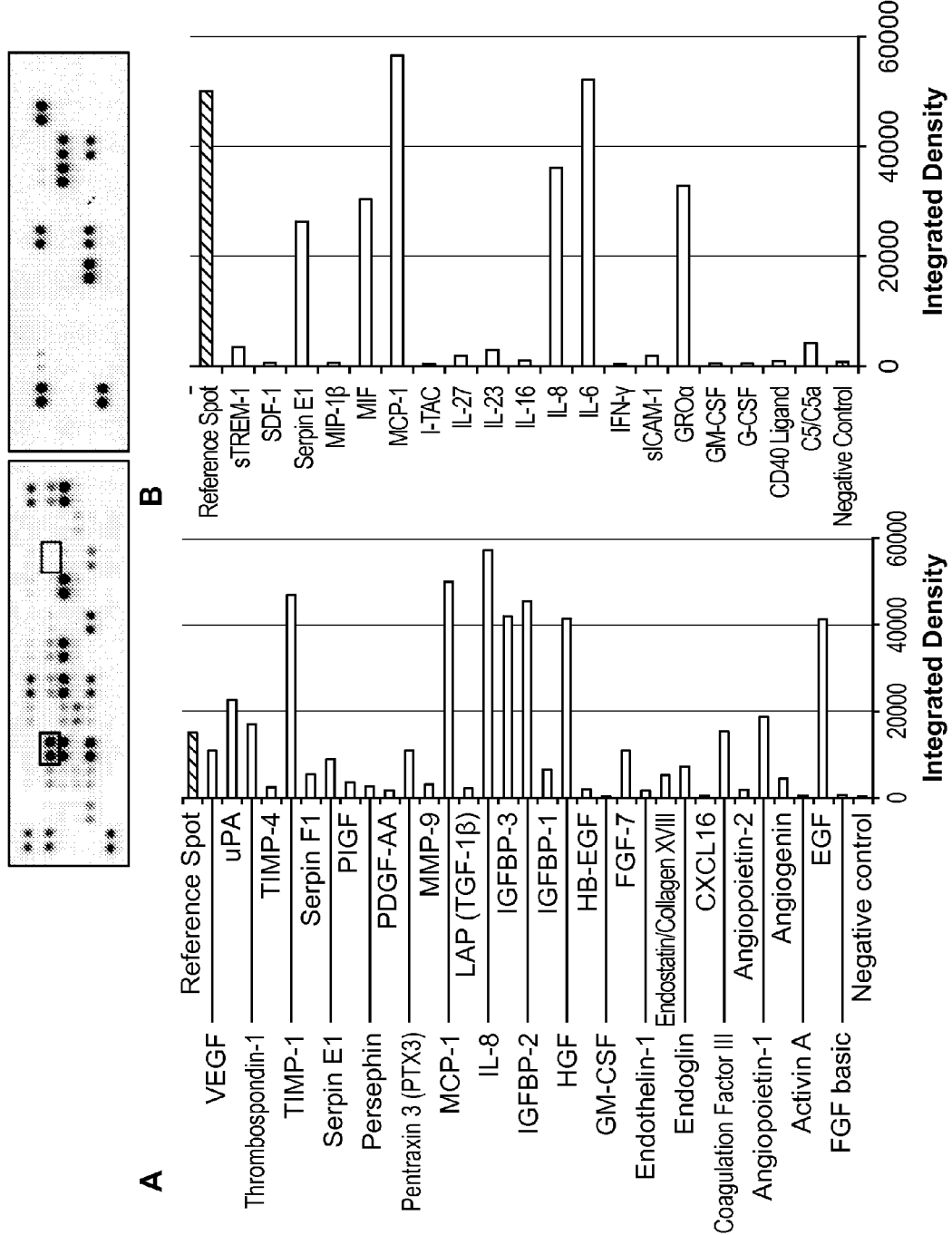
FIGS. 12A-12B show that pMSCs secrete angiogenic and immunomodulatory cytokines Array membranes and integrated density measurements from culture supernatants examined with angiogenesis (A) and proteome profiler (B) kits show that pMSCs secrete an array of paracrine factors.

Cytokine array assays show that in standard culture pMSCs express angiogenic and immunomodulatory cytokines (e.g. Angiogenin, Angiopoietin-1, HGF, VEGF, IL-8, MCP-1, uPA) (FIG. 12).

Figure 13:
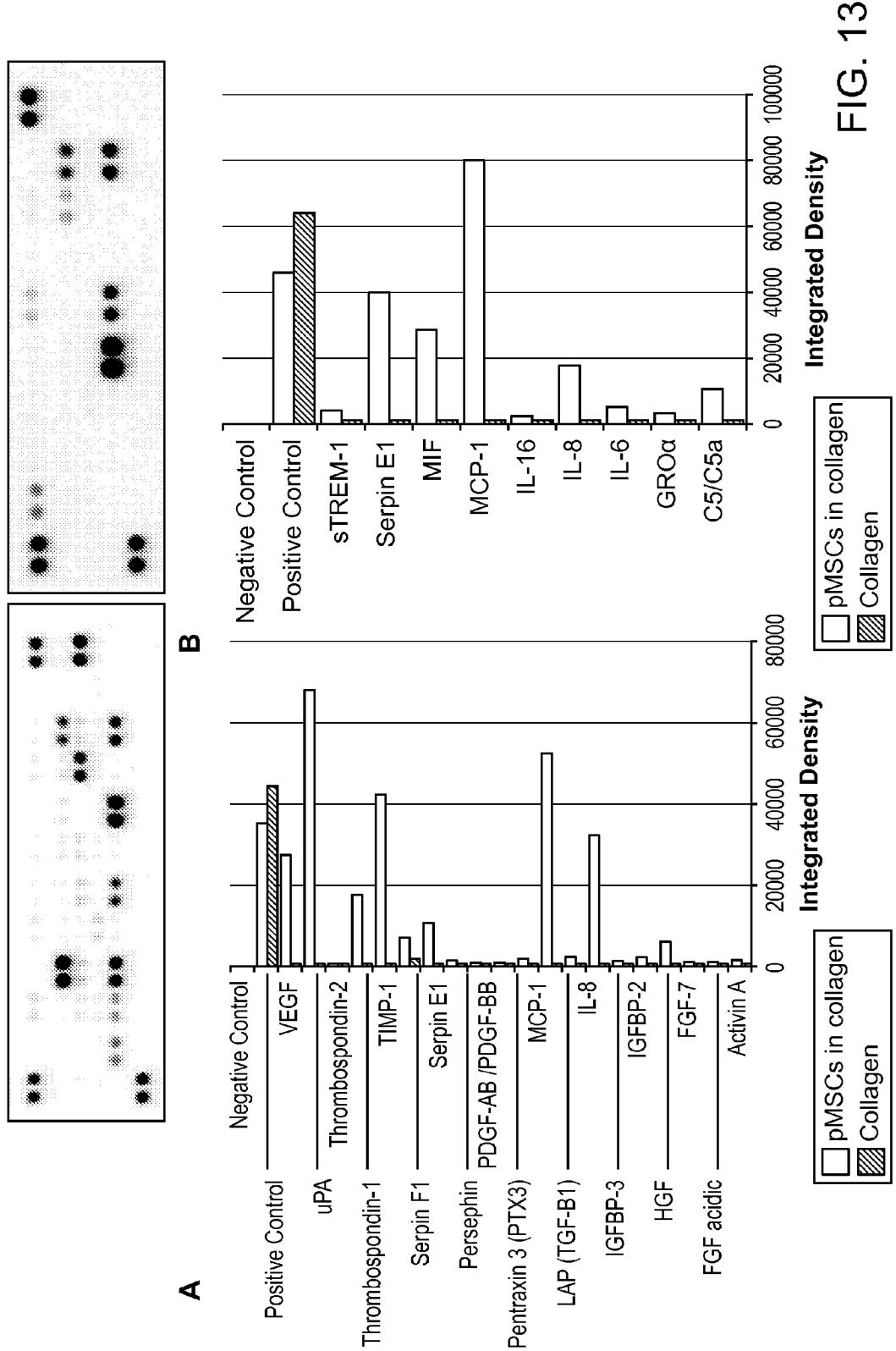
FIGS. 13A-13B show that pmSCs seeded in collagen gel continue to secrete cytokines Array membranes and integrated density measurements from collagen that was seeded with pmSCs and examined with angiogenesis (A) and proteome profiler (B) kits show that pmSCs secrete an array of paracrine factors.

Cytokine array assays after pMSCs are seeded in a laboratory-grade collagen hydrogel demonstrate that pMSCs continue to secrete immunomodulatory and angiogenic cytokines after they are introduced into a collagen hydrogel (FIG. 13). The presence of these cytokines in the culture supernatant and collagen hydrogel indicates that pMSCs may act via a paracrine mechanism to regenerate local tissue.

Concentrations of various secreted cytokines and growth factors were quantified using ELISAs. Supernatants were collected from bone marrow MSC (bmMSC) and pMSC cultures with an initial seeding density of $7.5 \times 10^5$ cells per 100 mm dish. Human BDNF, VEGF, HGF, MMP-9, MCP-1, and IL-8 levels were detected using Quantikine ELISA kits from R&D Systems. Human GDNF levels were detected using a DuoSet kit from R&D Systems. All ELISAs were performed according to the manufacturer's instructions and absorption measured using a Molecular Devices plate reader.

Figure 14:
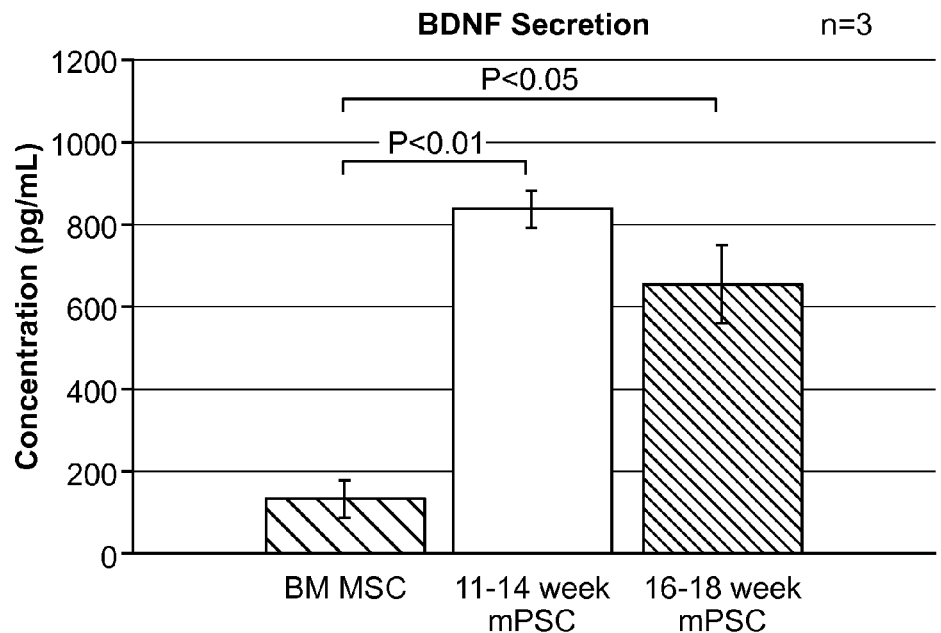
FIG. 14 shows that first- and second-trimester pmSCs secrete significantly more BDNF than BM-MSCs. 3 samples were analyzed for each study group using an ELISA kit. Samples were analyzed for statistical significance using paired t-test. p-value<0.05=*, p-value<0.01=**

BDNF is a neurotrophic factor that is vital to healing in the nervous system. Compared to BM-MSCs, pMSCs secrete significantly greater quantities of BDNF, potentially indicating an enhanced potential to promote healing and regeneration in the spinal cord (FIG. 14).

Experiment No. 2

In Vitro Neurorescue Assay

Neurorescue functionality of pMSC conditioned media (CM) was assessed using a neurorescue assay. Primary mouse cortical neurons were obtained from cortex tissue isolated from normal E16 pups after approval by the Institutional Animal Care and Use Committees (IACUC). Cortex tissue was dissected in smaller fragments (2-3 mm) and enzymatically dissociated using 0.25% Trypsin-EDTA (Sigma Aldrich) to produce a single cell suspension that was then plated on 24-well plates pre-coated with poly-D-lysine (Sigma Aldrich). Primary neuron culture media consisted of Neurobasal-A (Invitrogen) supplemented with B27 (Invitrogen) and 10 ng/ml nerve growth factor (R&D Systems). CMs collected from bmMSC and pMSC cultures at 72-96 hours were concentrated 12-80 fold using Amicon Ultra-15 Centrifugal Filter Units (EMD Millipore), and applied to neuron samples by supplementing normal neuron media with 100 µg/ml of CM protein. Primary cortex neurons were damaged by treatment with 100 µM 6-OHDA (Sigma Aldrich) for six hours, and subsequently treated for 24 hours with either neuron media containing CM protein supplement or neuron media alone as a positive control. Normal untreated neurons served as a negative control. Experiments were conducted on DIV 5-7 and plates fixed in 4% PFA at the end of the 24 hour period post-OHDA treatment. Viability of neurons was evaluated with immunocytochemical staining for MAP2 (EMD Millipore) and active Caspase-3 (EMD Millipore). Quantification of neuron survival was performed by counting DAPI, MAP2, and Caspase-3 positive cells from 5 fields of view in each well at 20× magnification, and counts were performed in each of the triplicate wells. Statistical analysis was performed using one-way ANOVA and Student's T-test.

Figure 15:
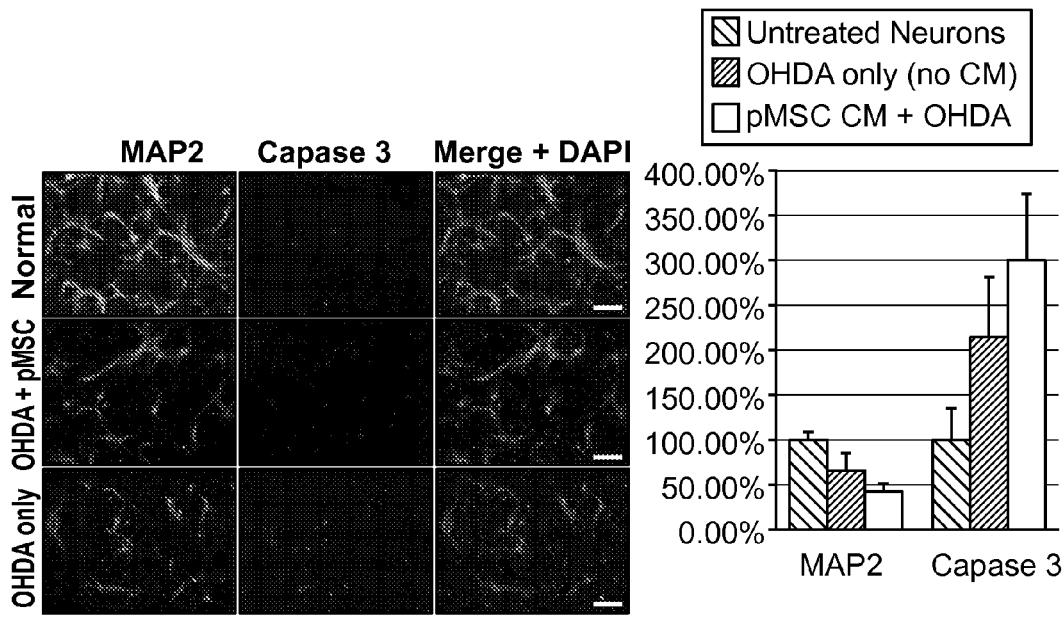
FIG. 15 (panels and graph) shows representative images of immunocytochemical staining of MAP2 and active Caspase 3 in normal E16 murine cortex neurons and neurons treated with 6-hydroxydopamine for 6 hours followed by either normal neuron media (positive control) or neuron media supplemented with 100 μg/ml pMSC conditioned media. Scale bars=100 μm. Counts of 5 fields of view from duplicate wells reveal ability of pMSC conditioned media to rescue MAP2 expression and decrease active caspase 3 after toxin treatment.
Figure 16:
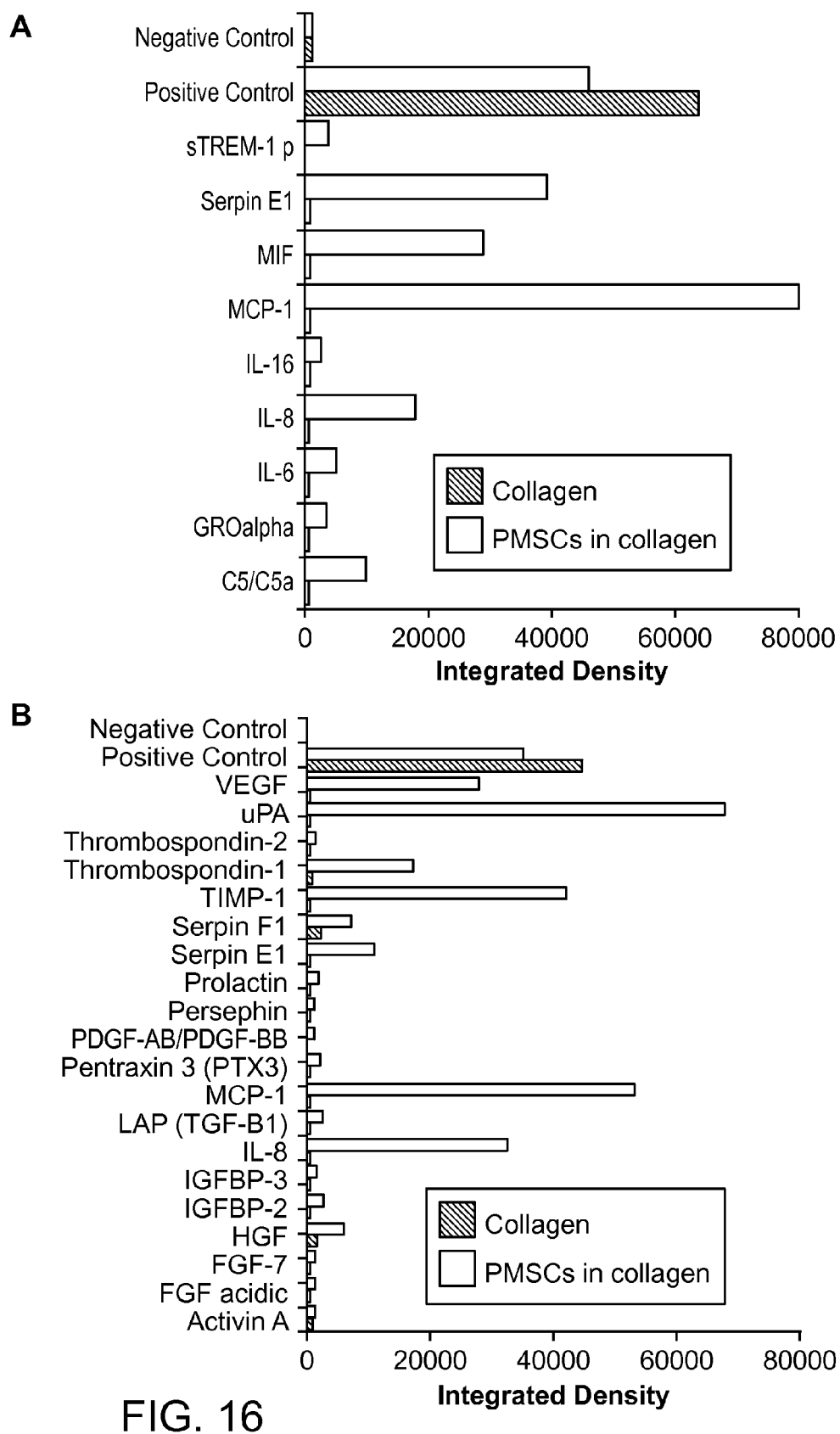
FIGS. 16A-16H show that characterization of early gestational age placental stem cells revealed unique paracrine properties. (A) Cytokine array analysis from $5 \times 10^5$ GFP+ PMSCs seeded in a collagen hydrogel demonstrated a diverse array of immunomodulatory and chemotactic cytokines including Serpin E1, MIF, MCP-1, IL-6, IL-8 and C5/C5a present in the secretome. (B) Human angiogenesis cytokine demonstrated several angiogenic factors including VEGF, Thrombospondin-1, and HGF, as well as immunomodulatory factors uPA, TIMP-1, MCP-1 and IL-8 being secreted by the GFP+ PMSCs. ELISAs were used to compare the secreted factors from three separate BM-MSC lines to the one PMSC line used in the studies. (C-H) The PMSC line displayed significantly higher levels of BDNF, HGF, and IL-8 in culture supernatants compared to the average levels secreted by the three BM-MSC lines (p=0.013, p=0.047, and p<0.0001, respectively). However, the PMSC line did not display a significant difference in levels of VEGF, MCP-1, and TIMP-1 compared to the average levels of the three BM-MSC lines.
Figure 16:
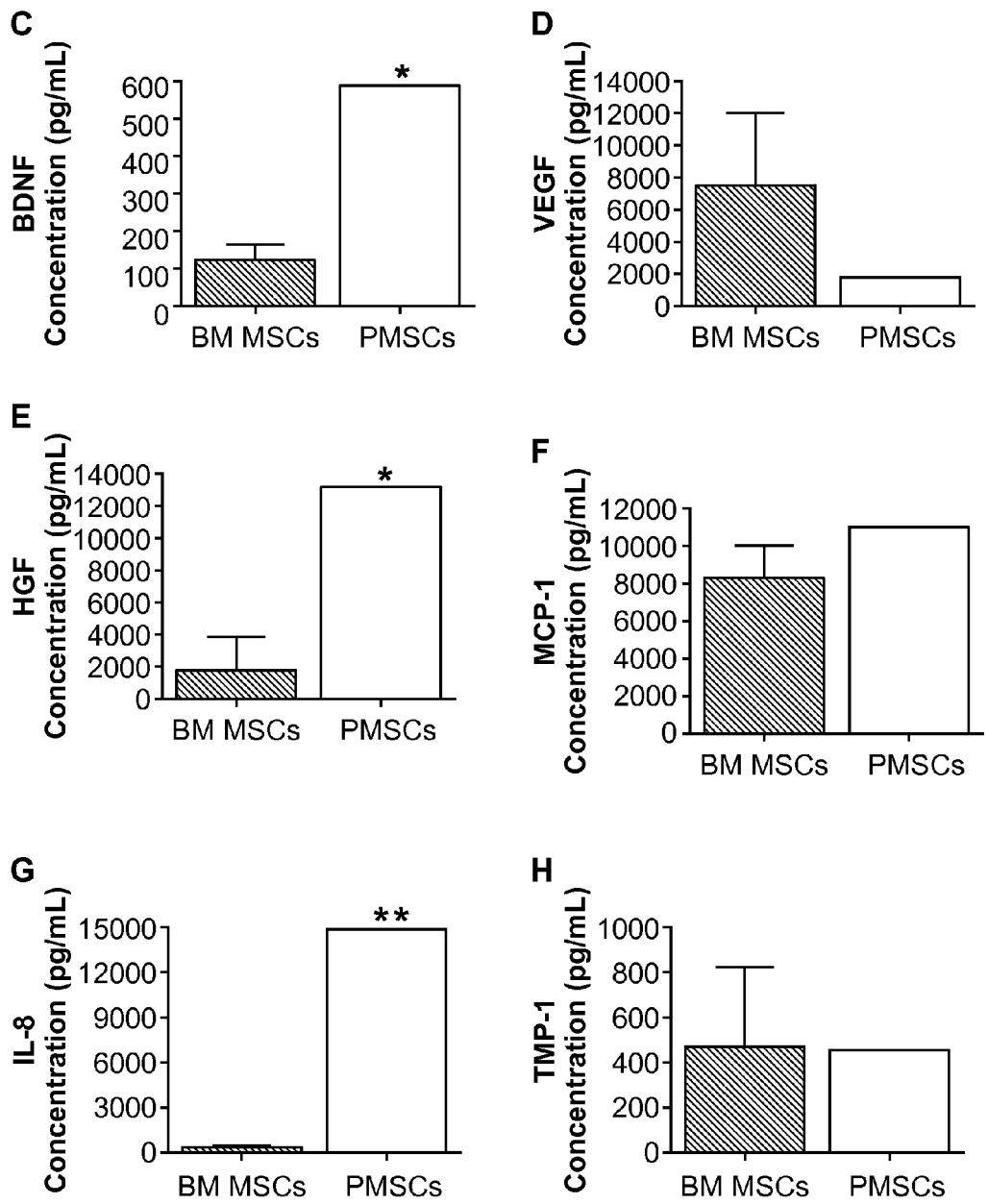

The results showed that pMSC conditioned media demonstrated a significant neurorescue effect on cortical neurons exposed to 6-OHDA in vitro with a statistically significant increase in the average percentage of MAP2 and a decrease in Casp3 positive cells in comparison to positive controls (FIG. 15).

Experiment No. 3

In this Experiment, Applicants support in a defined large animal model that human PMSCs can significantly augment in utero repair of MMC and improve associated neurologic deficits. Applicants demonstrate that PMSCs secrete neuroprotective and pro-healing paracrine factors and that PMSC conditioned media can significantly improve neuronal survival in vitro. Using the fetal sheep model of MMC, Applicants show that PMSCs applied at the time of in utero repair significantly improve postnatal motor function and increase preservation of large spinal cord neurons.

Materials and Methods

Isolation and Culture of PMSC Line from Human Pre-Term Placenta and BM-MSC Lines Donated placental tissue was collected at the UC Davis Medical Center with approval from the University of California, Davis Institutional Review Board. Applicants isolated PMSCs using an explant culture method from one randomly selected sample of gestational age (GA) 17 week old placenta. Briefly, Applicants dissected chorionic villus tissue into <5 mm pieces and washed it vigorously in sterile 1×PBS containing 1% penicillin-streptomycin. Applicants then dissected the tissue into smaller pieces and spread them across adherent culture dishes previously coated with CELLStart xeno-free substrate for 1 hour at 37° C. (Invitrogen). Applicants harvested adherent cells at 3-4 weeks and passaged the cells to a monolayer once residual tissue was removed. Applicants' standard culture media for all experiments was DMEM high glucose with 5% FBS, 100 units/mL of penicillin, 100 μg/mL of streptomycin, 20 ng/ml recombinant human bFGF (Peprotech) and 20 ng/ml recombinant human EGF (Peprotech).

Adult human bone marrow MSCs (BM MSCs) were a gracious gift from Claus Sondergaard, PhD (University of California, Davis). Cells were thawed from cryopreservation at passage 2 and conditioned media collected at passage 3-4 for each line. Culture dishes were pre-coated with CELL-Start xeno-free substrate as described above, and culture media for BM MSCs was identical to that used for PMSCs.

Flow Cytometry Analysis of PMSC Line

Applicants harvested PMSCs for flow cytometry using Accutase (Invitrogen) and counted PMSCs using Trypan Blue. Resuspended cells were split into fractions containing approximately $1\times10^6$ cells and stained with: FITC-CD44 (560977), PECy5-CD90 (555597), PE-CD73 (561014), Alexa Fluor 647-CD105 (561439), PE-CD29 (561795), PE-CD34 (560941), Alexa Fluor 647-CD31 (561654) (all B. D. Biosciences). Samples were counterstained using LIVE/DEAD® Fixable Aqua Dead Cell Stain Kit (Molecular Probes) to detect dead cells, and fixed in 4% paraformaldehyde (PFA) after staining Applicants collected flow cytometry data using a BD Fortessa LSR Cell Analyzer and analyzed the data with FlowJo (Treestar, Inc).

Immunocytochemistry of PMSC Line

Prior to immunostaining, PMSCs were fixed in 4% PFA in PBS, followed by membrane permeabilization with 0.5% Triton X-100 in PBS. Applicants incubated PMSCs with one of the following primary antibodies overnight at 4° C.: Sox1 (Millipore, AB15766)), Sox2 (R&D Systems, MAB2018), Sox9 (Abcam, AB3697), Sox10 (Sigma-Aldrich, MAB2864), Sox17 (R&D Systems, MAB1924), Nestin (Millipore, MAB5326), Twist (Sigma-Aldrich, T6451), Snail (Santa Cruz Biotech, SC-28199), Slug (Santa Cruz Biotech, SC-166476), S100β (Sigma-Aldrich, S2532), NFM (Santa Cruz Biotech, SC-16143), TUJ1 (Covance), MRB435P, or Oct4 (Santa Cruz Biotech, SC-5279). Applicants incubated the samples with AlexaFluor 546—conjugated secondary antibodies (Molecular Probes, A10040) for 1 hour at 22° C. Cell nuclei were counterstained with DAPI (Biotium, 40011). Images were collected with a Carl Zeiss Axio Observer D1 inverted microscope.

Multipotency Analysis of PMSC Line

To induce osteogenic differentiation, PMSCs were cultured in DMEM containing 10% FBS, 10 mM β-glycerol phosphate (Sigma Aldrich), 0.1 μM dexamethasone (Sigma Aldrich) and 200 μM ascorbic acid (Sigma Aldrich) for 3-4 weeks. To confirm osteogenic differentiation, cells were fixed in 4% PFA and stained with Alizarin Red (Sigma-Aldrich) to identify calcified matrix, and immunostained for the osteogenic marker osteocalcin (Epitomics).

To induce chondrogenic differentiation, PMSCs were cells were cultured as cell pellets in suspension in DMEM containing 10% FBS, 10 ng/ml transforming growth factor beta-3 (Peprotech), and 200 μM ascorbic acid (Sigma Aldrich) for 3-4 weeks. Following chondrogenic differentiation, chondrogenic pellets fixed in 4% PFA before subsequently being embedded in Optimal Cutting Temperature (OCT) compound (Fisher Scientific). Cross sections were immunostained for collagen II (Abcam) and stained with Alcian Blue (Sigma-Aldrich) to detect glycosaminoglycans.

To induce adipogenic differentiation, PMSCs were cultured in DMEM containing 10% FBS, 1 μM dexamethasone (Sigma Aldrich), 10 μg/ml insulin (Sigma Aldrich), 5 μM isobutylxanthine (AdipoGen), and 200 μM indomethacin (MP Biomedicals) for 3-4 weeks. Following adipogenic differentiation, cells were fixed in 4% PFA and stained with Oil Red 0 (Sigma-Aldrich) to identify lipid accumulation, and immunostained for lipid-associated protein perilipin (R&D Systems).

Enzyme-Linked Immunosorbent Assays

Concentrations of various secreted cytokines and growth factors were quantified using ELISAs. Supernatants were collected from BM-MSC and pMSC cultures with an initial seeding density of $7.5\times10^5$ cells per 100 mm dish. Human BDNF, VEGF, HGF, MMP-9, MCP-1, and IL-8 levels were detected using Quantikine ELISA kits from R&D Systems. All ELISAs were performed according to the manufacturer's instructions and absorbance measured using a Molecular Devices plate reader instrument.

In Vitro Neuroprotection Assay

The neuroprotective effects of PMSC conditioned media (CM) was assessed using a neuro-rescue assay. Primary mouse cortical neurons were isolated from normal E16 pups with approval from the University of California, Davis Institutional Animal Care and Use Committees (IACUC). Cortex tissue from separate mouse embryos were dissected into smaller fragments (2-3 mm) and enzymatically dissociated using 0.25% Trypsin-EDTA (Sigma Aldrich) to produce a single cell suspension that was then plated on 96-well plates pre-coated with poly-D-lysine (Sigma Aldrich) at a density of $10^5$ neurons per $cm^2$. Primary neuron culture media consisted of Neurobasal-A (Invitrogen) supplemented with B27 (Invitrogen) and 10 ng/ml nerve growth factor (R&D Systems) and 100 units/mL of penicillin, 100 μg/mL of streptomycin. CM collected from the pMSC culture at 72 hours were concentrated 70 fold using Amicon Ultra-15 Centrifugal Filter Units (EMD Millipore), and applied to neuron samples by supplementing normal neuron media with 100 μg/ml of CM protein. Primary cortex neurons were damaged by treatment with 100 μM 6-OHDA (Sigma Aldrich) for six hours, and subsequently treated for 24 hours with either (1) neuron media containing CM protein supplement or (2) neuron media alone as a positive control, or (3) with neuron media containing 100 μg/ml of vehicle control (pMSC base media collected from non-cell culture at 72 hours and concentrated similarly as cell-containing CM). Experiments were conducted on days in vitro 4-7. At the end of the 24 hour period post-OHDA treatment, cells were stained using a live/dead fluorescent assay kit (Molecular Probes, L3224) and viability analyzed using fluorescence intensity measurements collected using an i3 SpectraMax plate reader from Molecular Devices.

GFP Transduction of PMSCs

For cell tracking in the in vivo portion of this study, cells were transduced with a GFP-containing lentiviral vector (pCCLc-MNDU3-LUC-PGK-EGFP-WPRE construct from UC Davis/CIRM Institute for Regenerative Cures, Sacramento, Calif.). Cells were plated at a density of $7.5\times10^5$ cells per 100 mm and allowed to adhere overnight. The following morning, media was changed to 2 ml of transduction media (8 µg/ml protamine sulfate and 10 µg/ml lentiviral vector) for 6 hours; the culture was washed twice and normal culture media reintroduced. GFP expression was confirmed 72 hours later with fluorescent microscopy.

Seeding GFP-tagged PMSCs onto a Hydrogel Delivery Vehicle

GFP-labeled PMSCs were harvested from adherent cultures, pelleted and resuspended in complete media before being mixed at 4° C. (to prevent premature crosslinking) into a $5 \times 10^5$ cells/ml solution of 2 mg/ml rat tail collagen (B. D. Biosciences), water, PBS and 0.1N NaOH. Following homogenization and introduction of GFP-PMSCs, 1 ml of cell/collagen solution was placed into a 35 mm suspension culture dish and allowed to gel for at least 45 minutes at 37° C. After gelation was complete, 1 ml of complete culture media was added to the dish, covering the hydrogel layer. Control collagen gels were prepared identically, but no PMSCs were added to the mixture.

Cytokine Profile of GFP-tagged PMSCs Suspended in Hydrogel Delivery Vehicle

Cytokine array assays were performed on culture supernatants collected at 24-hours from GFP-PMSC containing and control collagen gels that were prepared in parallel with gels used for in vivo experiments. Cytokine secretion of GFP-PMSC seeded in collagen gels was identified using a Human Cytokine Array Panel A (R&D Systems) and Angiogenesis Array (R&D Systems). Assays were performed according to the manufacturer's instructions and membranes were read using a Bio-Rad ChemiDoc MP imaging system and further analyzed using ImageJ software and DotBlot analysis plugin.

In Vivo MMC Defect Creation and Repair

All protocols were approved by the University of California, Davis IACUC, and all animal care was in compliance with the Guide for the Care and Use of Laboratory Animals. All facilities used over the course of this study are accredited by the Association for the Assessment and Accreditation of Laboratory Animal Care International (Institute of Laboratory Animal Resources (1996)).

One week prior to surgery, time-mated, pregnant ewes were delivered to the housing facility where they had unrestricted access to food and water except for the 24-hour period directly preceding surgery. The first operation was performed at approximately GA-75. All ewes underwent survival laparotomy and hysterotomy, followed by creation of the MMC defect as previously described in detail (Meuli, M. et al. (1997) J. Pediatr. Surg. 32(3):448-452; von Koch, C. S. et al. (2005) American Journal of Obstetrics and Gynecology 193(4):1456-1462). Briefly, the MMC defect was surgically created in each fetal lamb by laminectomy of six lumbar vertebrae and removal of the dura overlying the spinal cord. The maternal hysterotomy and laparotomy incisions were closed in a routine fashion.

Approximately 25 days later, a second survival laparotomy and hysterotomy were performed to repair the MMC defect. Any overlying fibrinous exudate on the spinal cord was removed to allow for direct application of the treatment onto the open neural placode. Lambs were randomly divided into control and experimental groups. Lambs in the control group were treated with 1 mL of collagen applied directly to the neural placode. To hold the collagen in place, a singly-ply layer of Oasis, a commercially available extracellular matrix (ECM) patch, was secured over the defect with interrupted 6-0 monofilament sutures. The skin was then closed over the patch. Lambs in the experimental group were repaired with 1 mL of collagen gel seeded with $5 \times 10^5$ GFP-tagged PMSCs followed by ECM patch and skin closure in an identical fashion.

Motor Function Analysis

Lambs were delivered at term (approximately GA-145 days). After birth, motor function was evaluated for all lambs plus 3 normal, negative controls using the Sheep Locomotor Rating (SLR). In brief, motor function in seven categories was observed and scored on a scale of 1-15. A grade of 15 indicates completely normal function; grades of 0-4, 5-9, and 10-14 indicate severe, moderate and mild motor deficits, respectively. Locomotor testing was performed in person by two examiners within 24 hours; the best performance was used for analysis. Assessments were recorded by video camera. Two examiners, blinded to treatment group and live locomotor score, evaluated and scored all videos independently. All examiners met as a group to discuss scores; videos were reviewed to reconcile differences, and a consensus score was assigned to each lamb based on both live and video scores.

Histopathological Analysis

After completion of the motor function analysis, all lambs were euthanized and perfused with lidocaine and heparin, followed by 1 L of 0.9% NaCl and 2 L of 4% paraformaldehyde. The spinal cords of each lamb were dissected for analysis. After gross inspection, the cord was blocked into lumbar spinal segments and then embedded in Optimal Cutting Temperature compound for cryosectioning. A series of 20 µm sections were taken through each spinal segment. Nissl (Cresyl Violet) staining was performed on the tissue sections.

The full lumbar spinal cord was imaged for all lambs. A sample of 6 sections per lumbar segment for each animal were analyzed by ImageJ and averaged to determine height, width, and cross-sectional area of the grey matter, white matter, and entire spinal cord. The GNU Image Manipulation Program was used to create spinal cord tracings. The proportion of grey and white matter were calculated by dividing the respective tissue cross-sectional area by the total cross-sectional area of the spinal cord. The epicenter of the MMC lesion was defined as the lumbar segment with the greatest degree of deformation (defined by the cross-sectional height divided by the width). Large neurons, cells with a diameter of 30-70 µm as previously described (Gensel, J, C. et al. (2006) J. Neurotrauma 23(1):36-54), were counted with an inverted bright field microscope (Carl Zeiss Axio Observer D1) at 10× magnification using Nissl stained sections. All counts were performed by a single, blinded individual to maintain consistency. Epicenter counts were performed three times for each section to ensure accuracy, and the average number of neurons was calculated for each epicenter. Large neuron density was calculated by dividing the average number of neurons by the total cross-sectional area of grey matter to normalize for variability in the amount of grey matter present.

Statistical analyses were performed for the entire lumbar cord; subset analysis was performed to analyze the epicenters. In order to normalize the variability of cord size in different spinal cord segments, all calculations, including determining the lesion epicenter, were normalized by dividing by the average cross-sectional area for the corresponding lumbar segment in normal newborn lambs (n=3). Statistical analyses were performed using Student's T-test for continuous variables and Mann-Whitney U test for ordinal variables. Linear regression analysis was performed to evaluate the relationship between large neuron density and SLR score. Applicants included 3 normal controls in the regression analysis in addition to the 12 experimental animals. As the controls have no defined epicenter, the L3 lumbar segment was chosen as this was the most common level for the disease epicenter by both mean and median.

Immunohistochemical Analysis of Cellular Retention

To evaluate the presence of transplanted PMSCs in the sheep spinal cord tissue, fluorescence microscopy and immunohistochemical analysis with anti-GFP antibody (Invitrogen, A-11122) were used to detect GFP expression. Immunohistochemical analysis was performed at the lesion epicenter for all animals included in histopathologic analysis (n=12). Five-hundred thousand GFP-tagged cells were directly injected into the spinal cord of one lamb immediately after euthanization to serve as a positive control. Analysis focused on only the epicenter for all animals. Twelve cross-sections per animal were analyzed: 6 for GFP analysis, 3 for secondary antibody only, and 3 for isotype control. Immunostaining was performed as described previously (Wang, A. et al. (2011) Biomaterials 32(22):5023-5032). Briefly, the samples were washed in phosphate buffer saline (PBS) for 10 min, followed by permeabilization of cells with 0.5% Triton X-100 in PBS for 5 min. For primary antibody incubation, samples were incubated with anti-GFP antibody (1% BSA: 1:250) (6 sections), IgG isotype control (Invitrogen, A10040, 1% BSA: 1:625) (4 sections), and 1% BSA (4 sections) for 24 hours at 4° C. All samples were then incubated with AlexaFluor 546-conjugated secondary antibody (Molecular Probes, A10040, 1×PBS: 1:500) for 1 hour at 22° C. Finally, cell nuclei were counterstained with DAPI (Biotium, 40011, W: 1:5000) for 5 min 22° C. GFP analysis was performed by examining all sections using an inverted fluorescence microscope (Carl Zeiss Axio Observer D1) at 20× magnification.

Results

Early Gestational Human PMSCs Display Unique Paracrine Properties

Applicants harvested stem cells from human early gestational placenta in order to fully characterize Applicants' cells and investigate their in vtiro paracrine properties. Flow cytometry confirmed that cells were positive for established MSC markers CD105, CD90, CD73, CD44, and CD29, and negative for hematopoietic stem cell marker CD34 and endothelial cell marker CD31. Immunocytochemistry demonstrated that the cells uniformly express stem cell transcription factors Sox1, Sox2, Sox 9, Sox10, Sox17, Slug, Snail, and Twist, and intracellular neural and stem cell-related markers Nestin, TUJ1, NFM, and S100β. Some cells also stained positive for Oct 4, a transcription factor normally seen in pluripotent or more primitive stem cells. Using differentiation induction protocols, Applicants found that the cells can differentiate into osteogenic, chondrogenic and adipogenic lineages, as is characteristic of MSCs. Based on this characterization, Applicants concluded with confidence that Applicants' cells were PMSCs, and noted that, compared to classic BM-MSCs, they express markers suggestive of a more primordial state.

In order to prepare the cells for in vivo studies, Applicants transduced them with a lentiviral vector carrying the gene for green fluorescent protein (GFP), as described previously (Dull, T. et al. (1998) Journal of Virology 72(11):8463-8471). GFP has been widely used to label and track human stem cells introduced into animal models (Parr, A. M. et al. (2008) Neuroscience 155(3):760-770; Vroemen, M. et al. (2003) The European Journal of Neuroscience 18(4):743-751). To characterize the cells within the delivery vehicle, Applicants conducted cytokine array analysis of GFP' PMSCs seeded in collagen hydrogel. Applicants found that PMSCs secrete a wide array of paracrine factors within the first 24 hours after seeding, a time point comparable to when the cells would be implanted in vivo. The most highly secreted factors were uPA, VEGF, TIMP1, HGF, Thrombospondin-1, MCP-1, IL-8, Serpin E1, Serpin F1, and MIF, many of which have been previously implicated in the innate immune response to injury.

Applicants further analyzed the paracrine activity of Applicants' cells by quantifying the secretion of factors previously recognized to bolster wound healing, particularly in the spinal cord. Using ELISAs, Applicants compared PMSCs to BM-MSCs, which are already in early phase clinical trials as a treatment for spinal cord injury (Martinez, A. M. et al. (2014) World Journal of Stem Cells 6(2):179-194). ELISAs revealed that the PMSCs secreted significantly higher levels of BNDF (p=0.013), HGF (p=0.047), and IL-8 (p<0.0001) than BM-MSCs (FIGS. 16C-16H). There were no statistical differences in VEGF (p=0.38) and MCP-1 (p=0.29) secretion between BM-MSCs and PMSCs.

To ascertain whether PMSC paracrine secretion can significantly improve the survival of traumatized central nervous system neurons, Applicants performed an in vitro neuroprotection experiment. PMSC conditioned media demonstrated a notable neurorescue effect on cortical neurons previously exposed to the neurotoxin 6-OHDA. While the exact mechanism of this neuroprotective effect cannot be determined from these studies, the complex PMSC cytokine profile clearly improves neuronal survival.

Applying PMSCs in Utero Significantly Improves Postnatal Motor Function in the MMC Fetal Lamb Model After full cell characterization, the next step was to test the effects of PMSCs in the fetal ovine model of MMC. Applicants hypothesized that the unique in vitro profile of the cells in combination with the impressive rescue of neurons seen in Applicants' neuroprotection experiments may result in improved motor function when PMSCs are used to augment in utero repair in the fetal lamb. The study included all lambs surviving to term (n=12). Applicants surgically created a MMC defect in fetal lambs at an average gestational age (GA) of 77.3 days (range: 73-81) by removing six lumbar laminae and excising the dura in a standardized fashion. The average length of the resultant spinal column defect was 3.1 cm (±0.2 cm). Applicants noted direct cord damage at the time of defect creation in one lamb subsequently treated with PMSCs; no other complications were noted during the defect creation surgeries. Applicants performed the second operation for defect repair at an average GA of 103.5 days (range: 97-107). There were no complications noted during the repair operations.

The average GA at birth was 145.7 days (range: 138-152 days). Motor function was scored within 24 hours of birth for all 12 experimental lambs plus 3 normal controls using the Sheep Locomotor Rating (SLR) scale (Brown, E. G. et al. (2014) J. Pediatr. Surg. (Under Review)). One vehicle only-repaired lamb sustained a tibial fracture during delivery that was discovered after euthanization. The injury may have negatively biased the lamb's motor function score. However, the SLR scores for the injured limb and the contralateral, uninjured limb were similar, indicating that the lamb's overall motor function score was likely representative of actual function.

All three normal lambs were able to ambulate normally shortly after birth (SLR score: 15). Lambs in the PMSC-treated group received significantly higher neurologic scores compared to lambs in the vehicle only group (p=0.0108) (FIG. 18). Of the lambs treated with PMSCs, two lambs demonstrated completely normal locomotion (SLR score: 15), two had only mild neurologic deficits (SLR scores: 10, 13), two had moderate deficits (SLR scores: 5, 8) and, importantly, none had severe deficits. Of note, the PMSC-treated lamb with the lowest SLR score was the lamb that suffered direct cord damage during defect creation. Sixty seven percent of the lambs treated with PMSCs were capable of ambulation. No lambs in the vehicle only group were able to ambulate, and none exhibited only mild motor deficits. Two vehicle control lambs displayed moderate deficits (SLR scores: 6, 8), but the majority (4/6) demonstrated severe neurologic deficits (SLR scores: 2, 2, 4, 4). Notably, in this study Applicants operated on two sets of twins, animals with ostensibly identical genetic backgrounds and intrauterine environmental conditions. For both sets of twins, Applicants treated one lamb with PMSCs and the other with the vehicle only. Both lambs treated with PMSCs were capable of normal ambulation, while their twins exhibited moderate to severe neurologic deficits.

Histopathologic Analysis and Cell Retention after in Utero Application of PMSCs

Histopathologic analysis was performed to see if the exciting locomotor recovery seen in PMSC-treated lambs correlated with histologic preservation of the elements of the spinal cord or normal spinal cord architecture. Following euthanization, perfusion, and spinal cord dissection, gross pathological inspection noted marked compression of the cord at the level of the MMC lesion for all 12 MMC lambs compared to the normal controls. Applicants did not note any other gross abnormalities of the spinal cord or complications of stem cell application, such as tumor formation.

Figure 17:
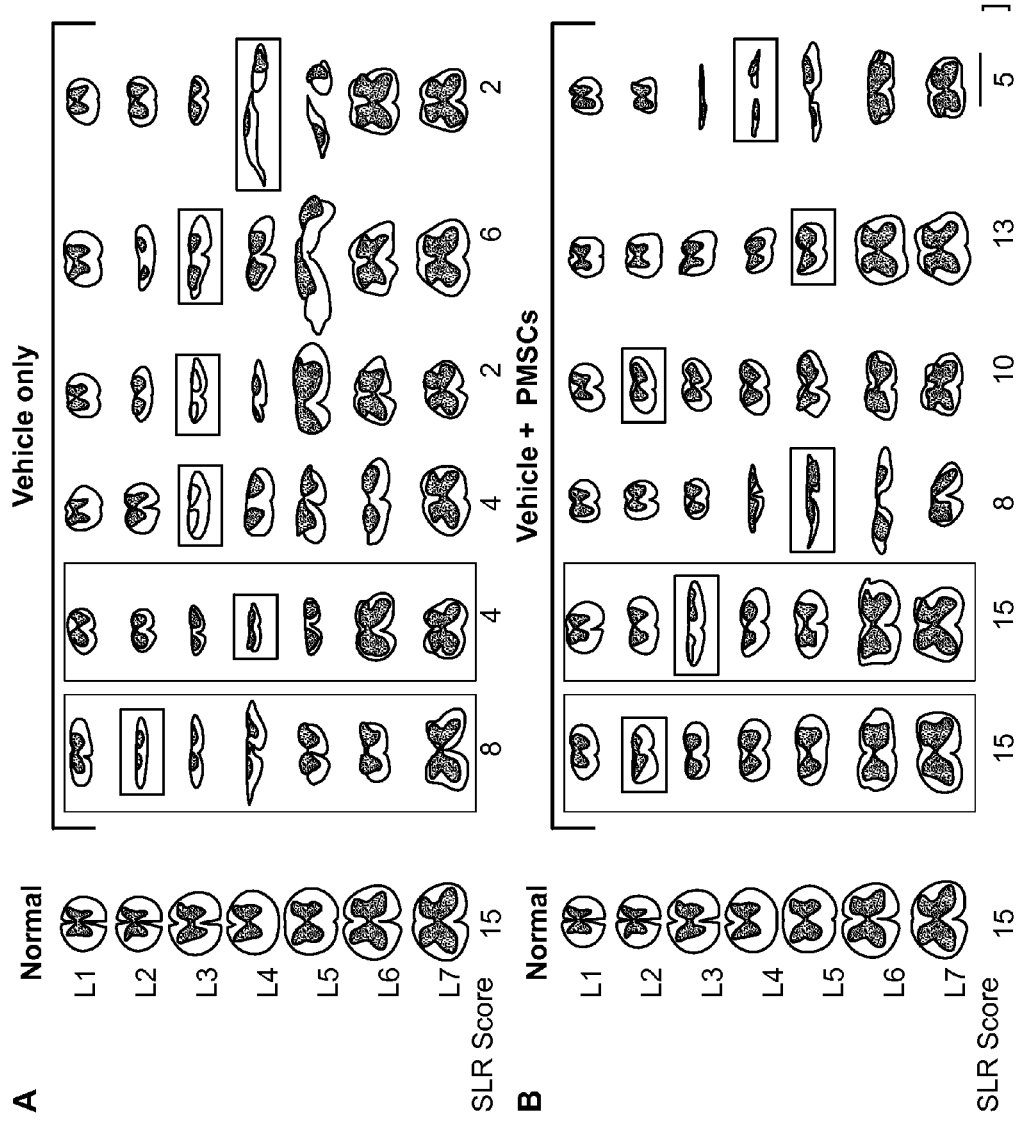
FIGS. 17A-17B show cross sectional histologic analysis was completed for 15 lambs, (normal n=3, vehicle only n=6, vehicle+PMSCs=6). Sections were cut at a thickness of 20 μM for each dorsal root segment from L1-L7 where the MMC defect was created. Resulting sections were then stained with cresyl violet and tracings were created to highlight the grey (shown in blue) and white matter (shown in green). The red box for each animal designates the lesion epicenter, the area with the greatest degree of cord deformation, (shown in gray-scale). (A) The six animals treated with vehicle only are shown in comparison to a normal cord with the SLR score for each animal listed below the lumbar segments. (B) The six animals treated with vehicle+PMSCs are pictured in the lower panel with their corresponding SLR scores listed below. The asterisk marks the spinal cord that was noted to have direct cord damage during the MMC defect creation. The blue and purple boxes highlight the lumbar segments for the two sets of twins, with one twin lamb treated with vehicle+PMSCs and the other corresponding twin lamb treated with vehicle only in each set of twins, (shown in gray-scale). Scale Bar=5 mm
Figure 19:
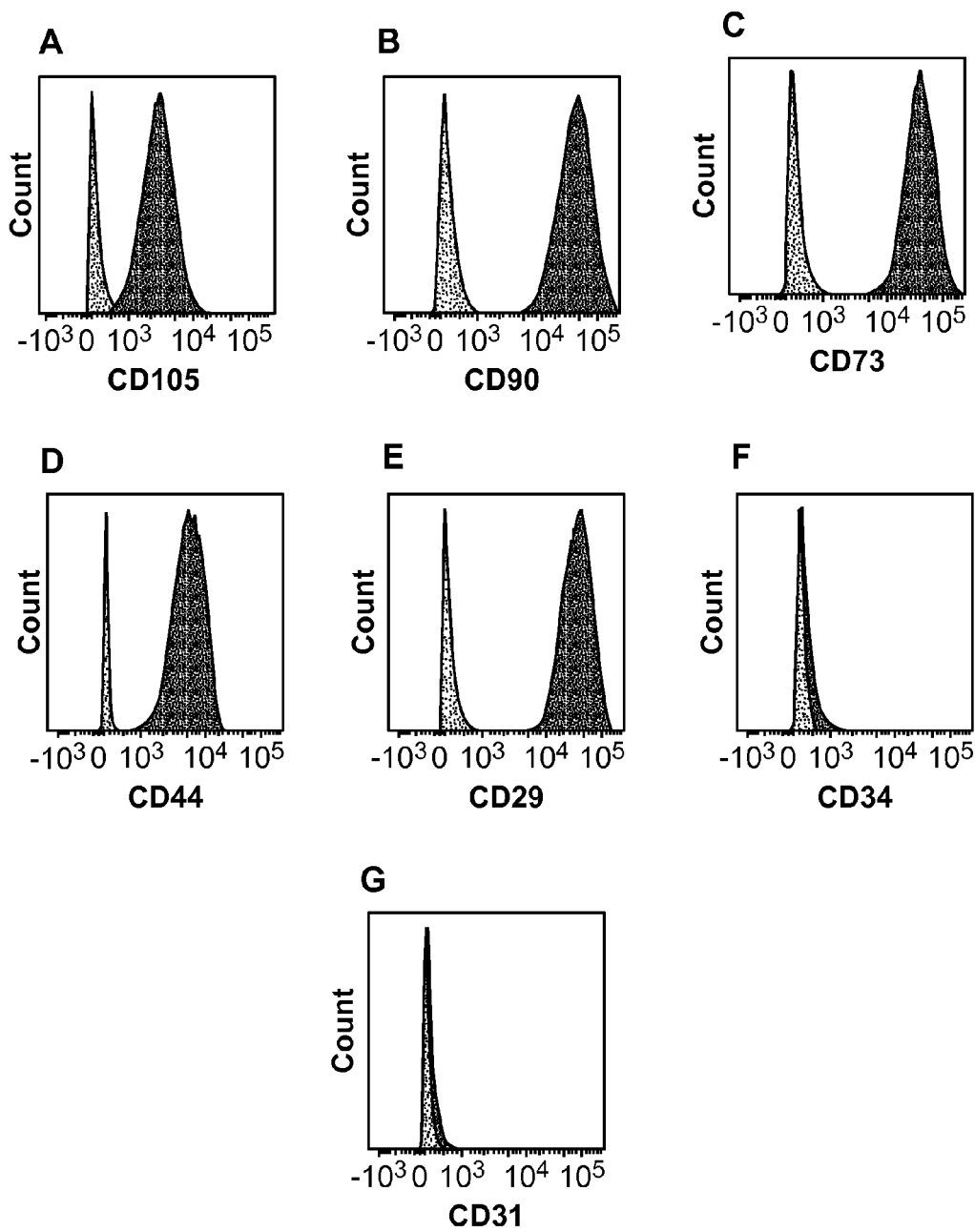
FIGS. 19A-19G show that flow cytometry immunophenotyping indicates typical MSC surface profile for this pMSC line. Cells were positive for MSC markers CD105, CD90, CD73, CD44, and CD29 and were negative for hematopoietic and endothelial lineage markers CD34 and CD31, respectively. Stained sample profile is shown in red and negative control (either isotype specific control or unstained cells in the case of CD90 and CD44), (reproduced in gray-scale).
Figure 20:
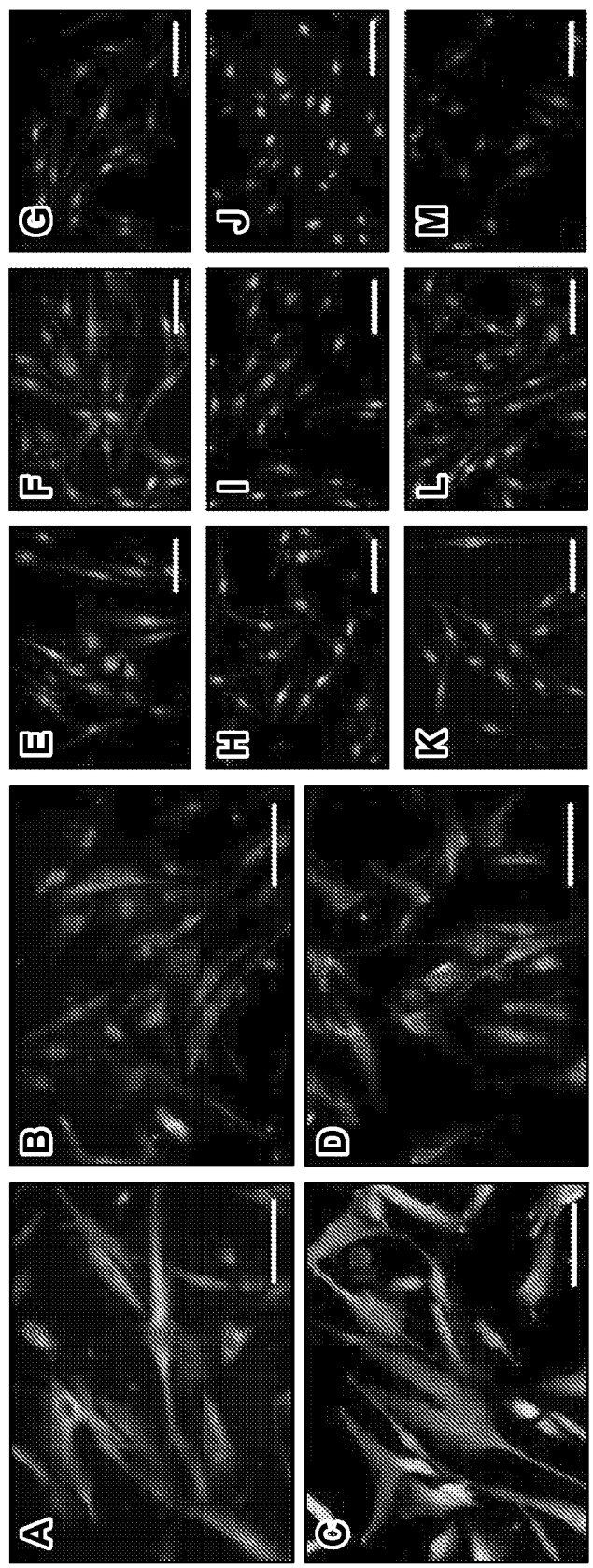
FIGS. 20A-20M show immunocytochemistry of intracellular proteins and transcription factors. PMSCs displayed positivity for proteins commonly associated with neural lineage such as TUJ1 (A), Nestin (B), NFM (C), and S100β (D) as well as transcription factors Sox1 (E), Sox2 (F), Sox9 (G), Sox10 (H), Sox17 (I), Slug (J), Snail (K), and Twist (L); and some positivity for Oct4 (M), (shown in gray-scale). Scale bars=100 μm.
Figure 21:
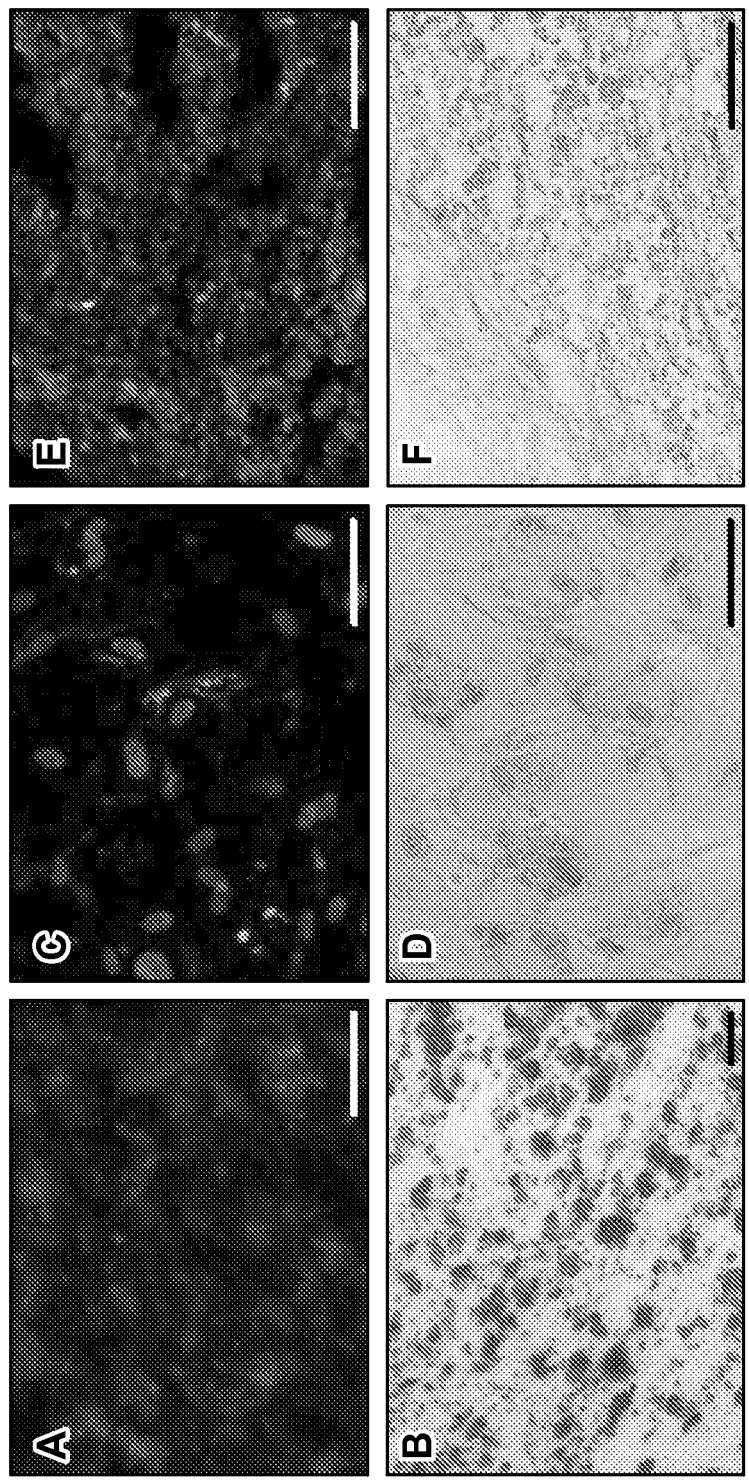
FIG. 21 (panels A-F) shows directed differentiation of PMSC line. Osteogenic differentiation confirmed by osteocalcin immunostaining and Alizarin Red staining Adipogenic differentiation confirmed by Perilipin immunostaining and Oil Red staining Chondrogenic differentiation confirmed by collagen II immunostaining and Alcian Blue staining, (reproduced in gray-scale). Scale bars=100 μm.
Figure 22:
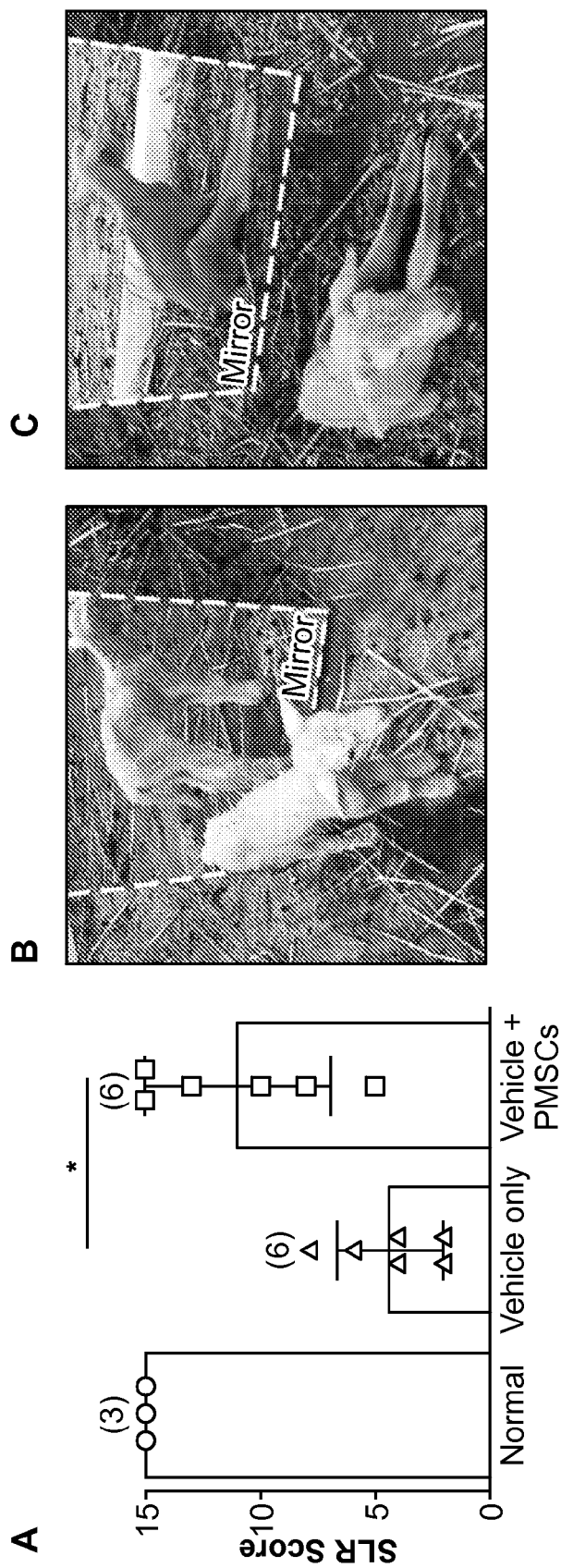
FIGS. 22A-22C show that lambs treated with PMSCs exhibit improved motor function. (A) Sheep Locomotor Recovery (SLR) scores, ranging from 0-15, for PMSC treated SB lambs, as well as vehicle controls and normal controls. (B and C) Behavioral recovery of twin SB lambs treated with human PMSCs+vehicle (B) and the vehicle only as a control (C). The twin treated with PMSCs exhibited normal hind limb motor function (B), while the twin treated with the vehicle alone displayed hind limb paralysis characteristic of SB (C).
Figure 23:
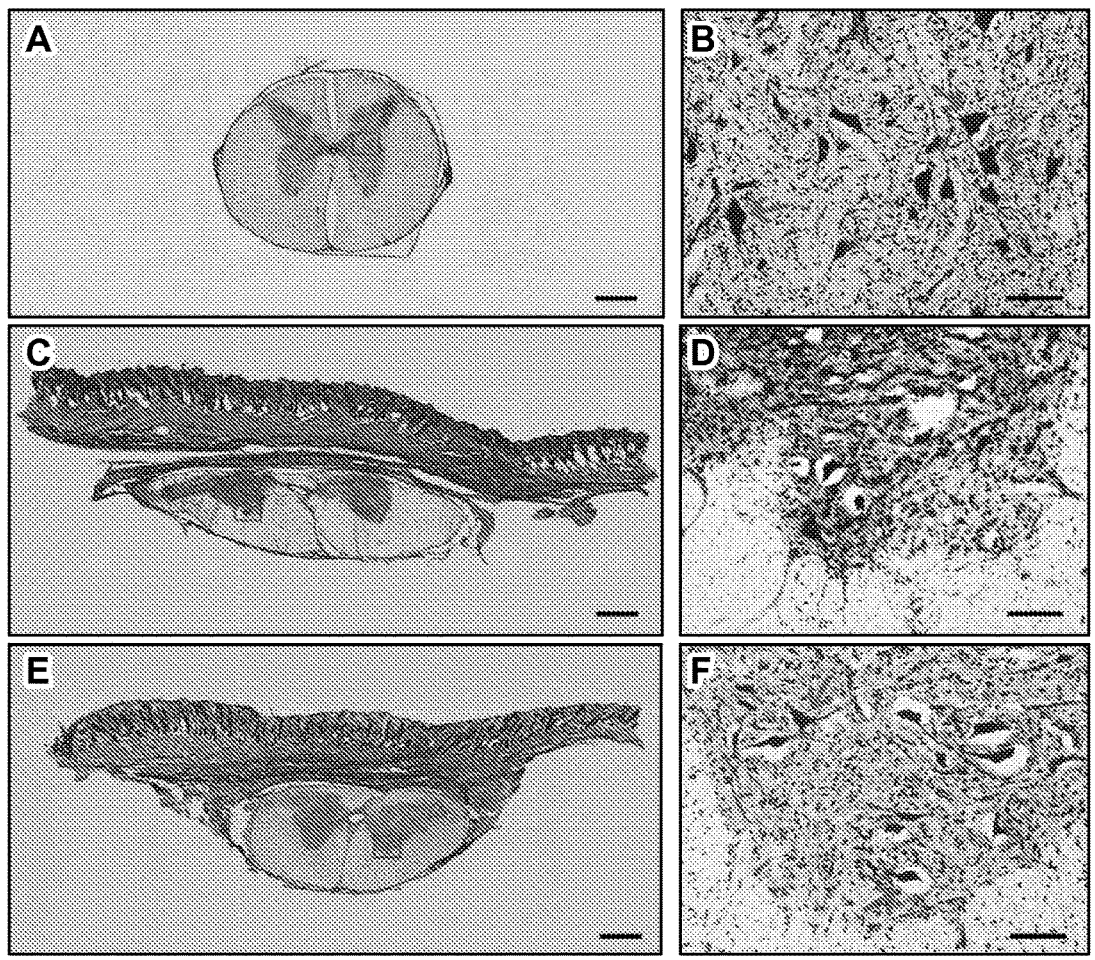
FIGS. 23A-23F shows increased large neuron density in the spinal cord of PMSC treated lambs. Crysel violet stained images taken from the epicenter of the SB lesion illustrate the differing density of large neurons (cell size>30 um) in normal controls (A and B), lambs treated with the vehicle only (C and D) and PMSC treated lambs (E and F). Large neuron density is significantly higher in PMSC treated lambs than in the vehicle only lambs. Scale bars represent 1 mm in A, C, and E and 100 um in B, D and F.

Cross-sectional tracings through the length of the lumbar spinal cord displayed prominent cord compression in all 12 MMC animals in contrast to the normal lumbar cords of the normal controls (FIG. 17). However, the degree of deformation varied throughout the lumbar cord, and by animal. At the lesion epicenter, or the level of greatest spinal cord deformation as determined by height/width normalized by lumbar segment, no significant differences in spinal cord cross-sectional area ($p=0.711$), degree of deformation ($p=0.245$), or proportional area composed of grey or white matter ($p=0.969$ and $p=0.571$, respectively) was present between the two MMC groups. However, the density of large neurons—number of neurons 30-70 um in diameter normalized to the cross-sectional area of grey matter—was significantly greater in PMSC-treated animals in comparison to vehicle controls ($p=0.0125$) FIG. 27. Linear regression analysis confirmed a positive, significant association between increased density of large neurons and higher SLR scores ($R^2=0.5108$, $p=0.0028$m).

Applicants performed both fluorescence microscopy and immunohistochemistry with anti-GFP antibody (Invitrogen, A-11122) to evaluate PMSC retention in the lamb spinal cord. Applicants saw no evidence of GFP+ cells in the spinal cord or surrounding tissues in any cell-treated animal, suggesting that the PMSCs did not migrate or integrate into the cord tissue.

Discussion

This study is the first to use PMSCs derived from early gestational chorionic villus to augment in utero repair of MMC in a rigorously defined large animal model. The placenta is a well-known source of progenitor cells (Genbacev, O. et al. (2011) Stem Cells 29(9):1427-1436; Bacenkova, D. et al. (2011) Cytotherapy 13(9):1047-1056). Applicants selected early gestational PMSCs as Applicants' therapeutic cells based on clinically feasible time points for autologous therapy.

Applicants' PMSCs exhibited a comparable in vitro profile to other placenta-derived MSCs described in the literature (Barlow, S. et al. (2008) Stem Cells and Development 17(6):1095-107; Hass, R. et al. (2011) Cell Communication and Signaling: CCS 9:12). Applicants' cell line expressed MSC markers CD105, CD90, CD73, CD44, and CD29 as well as transcription factors, such as Oct4 and Sox2, often associated with pluripotent stem cells and embryonic stem cells (Avilion, A. A. et al. (2003) Genes & Development 17(1):126-140; Niwa, H. et al. (2000) Nature Genetics 24(4):372-376). The expression of these factors suggest that PMSCs may be more primitive compared to BM-MSCs. Importantly, the PMSCs used in this study also exhibited a unique secretory profile. The PMSCs secreted substantially and significantly more HGF, IL-8 and BDNF than BM-MSCs, which have already been used to treat spinal cord injury in clinical trials (Martinez, A. M. et al. (2014) World Journal of Stem Cells 6(2):179-194). HGF is a potent angiogenic factor shown to activate endothelial cell migration and proliferation and may have contributed to wound healing in vivo by promoting rapid neo-vascularization (Bussolino, F. et al. (1992) The Journal of Cell Biology 119(3):629-641; Ferrara, N. et al. (2003) Nat Med. 9(6):669-676; Yancopoulos, G. D. et al. (2000) Nature 407 (6801):242-248). IL-8 is a cytokine with a well-documented, powerful effect on the innate immune response (Baggiolini, M. et al. (1992) FEBS Letters 307(1):97-101). Additionally, during pregnancy placental natural killer cells secrete IL-8 as part of tissue remodeling and neoangiogenesis (Vacca, P. et al. (2013) Journal of Reproductive Immunology 97(1):14-19). BDNF, a powerful neurotrophin, has widespread effects on the nervous system, and affects synaptic plasticity, nerve fiber regrowth, and inflammation after injury (Lu, B. et al. (2014) Handbook of Experimental Pharmacology 220:223-250; Weishaupt, N. et al. (2012) Experimental Neurology 238(2):254-264). Heightened secretion of BDNF may play a role in the in vitro and in vivo neuroprotective effects of PMSCs. The critical finding that PMSC-conditioned media protects cortical neurons from toxic damage suggests that PMSCs may function through a paracrine mechanism to spare central nervous system neurons and promote spinal cord healing.

Corroborating Applicants' locomotor findings, treatment with PMSCs significantly increases the density of large neurons in the spinal cord grey matter. Applicants' prior work in this model has shown that little spinal cord tissue and few large neurons remain at the level of the lesion in unrepaired lambs (Brown, E. G. et al. (2014) J. Pediatr. Surg. 49(1):133-137, discussion at pages 137-138). Applicants, and others, have shown that physical protection of the exposed spinal cord mediates histological improvements (Brown, E. G. et al. (2014) J. Pediatr. Surg. 49(1):133-137, Discussion 137-138; Meuli, M. et al. (1997) J. Pediatr. Surg. 32(3):448-452; Adzick, N. S. (2010) Semin. Fetal Neonatal Med. 15(1):9-14). Vehicle only-repaired lambs in this study did exhibit some degree of tissue and large neuron preservation, likely indicating that the extra physical protection conferred by applying the delivery vehicle bestows some benefit compared to no treatment. However, treatment with PMSCs significantly increased large neuron density at the lesion epicenter compared to vehicle control, a critical therapeutic benefit given the significant relationship between increased large neuron density and improved SLR score on regression analysis. Interestingly, there was no difference in spinal cord cross-sectional area or spinal cord deformation between the two groups, indicating that while the PMSCs were able to rescue neurons, they were not able to reconstitute the normal cytoarchitecture of the spinal cord.

This study presents the first evidence of a stem cell therapy that dramatically improves functional outcome compared to animals treated with the vehicle alone in a well-established large animal MMC model that consistently produces severe motor deficits. PMSCs possess distinctive neuroprotective properties in vitro and in vivo and demonstrate an amazing rescue of distal motor function.

Preclinical Studies in Support of Utility and Efficacy

Applicants' have shown that PMSCs have the capability to protect neurons from damage in the fetal lamb model of SB. The neuroprotective capabilities of PMSCs and C-pmSCs are then examined in a rat hemisection model of adult SCI at T9 spinal cord segment. At 7 days and 14 days after lesion, rats are treated with PMSCs delivered by a collagen-based hydrogel, treated with the hydrogel alone as a negative control, or kept as an untreated control. The rats are sacrificed at 2 weeks and 3 months post transplantation. The 2-week time point is for the examination of spinal cord tissue remodeling at early time points. The 3-month time point is for histological analysis of spinal cord tissue after functional recovery. To determine functional recovery of disabled limb function, behavior test using BBB locomotor rating scale is performed every other week for 3 months. Histological analysis at 2-week and 3-month time points are performed to determine the effects of different treatments on neuronal survival, axon growth, glial scar formation, astrocyte population, angiogenesis and the distribution and fate of implanted PMSCs.

Experiment No. 5

Clinical Application

For clinical administration, PMSCs are thawed and release tests (gram stain and viability) are conducted. Prior to delivery to the operating room, PMSCs are transferred into the matrix and packaged into a sterile syringe kept on ice. Chain of custody is recorded and strictly controlled in accordance with standard operating practices.

Without being bound by theory, PMSCs can derive their therapeutic potential from a transient release of paracrine factors that protect damaged neurons in the exposed spinal cord. In vivo studies in the fetal sheep model of spina bifida revealed that animals treated with PMSCs exhibit a significantly higher density of neurons in the grey matter of the spinal cord, and Applicants' in vitro studies revealed that PMSCs secrete a substantial amount of neuroprotective growth factors and cytokines No cellular engraftment was observed in the spinal cord.

Histological inspection of the spinal cord of spina bifida lambs revealed a significant increase in neuron density in the grey matter of the spinal cords of the PMSC treated lambs compared to that of the vehicle only lambs. Applicants did not observe significant differences between size of the spinal cord and the proportion of white and gray matter in the cord between the PMSC-treated and vehicle control lambs. These results indicate that the locomotor recovery observed in the PMSC treated lambs is due to the neuroprotective effects of the cells as opposed to remodeling of the spinal cord structure. Regression analysis revealed that neuron density was significantly associated with motor function.

Cytokine array assays conducted on Applicants' PMSCs displayed numerous immunomodulatory and angiogenic cytokines (e.g., Angiogenin, Angiopoietin-1, HGF, VEGF, IL-8, MCP-1 and uPA), indicating that PMSCs have the potential to modulate tissue healing via paracrine activity. Notably, PMSCs secreted significantly higher amounts of HGF, IL-8, and BDNF than adult bone-marrow mesenchymal stromal cells (BM-MSCs), whose regenerative properties have been widely reported. HGF is a potent angiogenic factor that has been shown to activate endothelial cell migration and proliferation and may have contributed to wound healing in vivo by promoting quick vascularization (Bussolino F, et al. J. Cell Biol. 1992; 119(3):629-641). IL-8 is a cytokine with a well-documented and powerful effect on the innate immune response (Baggiolini M, et al. FEBS Letters. 1992; 307(1):97-101); IL-8 is also secreted during pregnancy by placental natural killer cells as part of tissue remodeling and neoangiogenesis (Vacca P, et al. J Reprod Immunol. 2013; 97(1):14-19). BDNF is a powerful neurotrophin, with widespread effects on the nervous system. BDNF affects neuronal survival, synaptic plasticity, nerve fiber regrowth, and inflammation after injury (Lu B, Handb. Exp. Pharmacol. 2014; 220:223-250. Weishaupt N, et al. Exp. Neurol. 2012; 238(2):254-264). Significant levels of BDNF secretion may play a critical role in the observed in vivo neuroprotective effects of PMSCs.

Applicants have developed a reliable protocol to isolate PMSCs from human preterm placental tissue of gestational age (GA) of 17 weeks. Applicants' in vitro studies demonstrate Applicants can isolate and rapidly expand PMSCs to a substantial quantity. For example, from 50 mg of placental tissue of this gestational age, Applicants can obtain over $10^8$ cells within 2 months of in vitro expansion. Placenta PMSCs exhibit 99% purity in terms of surface marker expression (positive for CD105, CD90, CD73, CD44, CD29 and negative for CD31, CD34, CD45) after they have been cultured for five passages.

In Applicants' large animal studies, the dose was defined as $5 \times 10^5$ PMSCs in a 1 ml of collagen based matrix. The exact final dose for administration to humans or other mammals can be determined by extrapolation of this dosing by the treating physician or veterinarian. A single product dose will be topically applied to the open wound of the fetal spinal defect during in utero surgical repair. No further doses may be needed, but the treatment protocol will be determined by the treating physician, the condition being treated and the subject undergoing treatment.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for treating spina bifida in a subject in need thereof comprising administering to the subject an effective amount of an isolated pre-term placenta-derived multipotent stem cell or cells (PMSCs) or culture conditioned media therefrom.

2. The method of claim 1, wherein the PMSCs comprise chorionic villus (CV)-derived multipotent stem cells (C-mpSCs).

3. The method of claim 1, wherein the PMSCs or the culture conditioned media therefrom are administered in a pharmaceutically acceptable carrier or a biocompatible matrix.

4. The method of claim 1 or 3, wherein the subject is a fetus and the PMSCs or the culture conditioned media therefrom is administered to the fetus in utero.

5. The method of claim 1, wherein said PMSCs express one or both markers of $CD56^+$ or $CD271^+$.

6. The method of claim 5, wherein said PMSCs express one or more markers of $CD105^+$, $CD90^+$, $CD73^+$, $CD44^+$ or $CD29^+$.

7. The method of claim 5, wherein said PMSCs express the marker $CD184^+$.

8. The method of claim 1, wherein said PMSCs express an integrin receptor comprising one or both of CD49d or CD49f.

9. The method of claim 1, wherein said PMSCs express an intracellular marker comprising one or more of Nestin, Vimentin, S100β or neurofilament medium (NFM).

10. The method of claim 1, wherein said PMSCs express a transcriptional factor comprising one or more of Sox2, Sox10, Sox17 or Slug.

11. The method of claim 1, wherein said PMSCs lack expression of one or more endothelial markers or hematopoietic markers.

12. The method of claim 11, wherein said marker is one or more of CD31, CD34 or CD45.

13. The method of claim 1, wherein the conditioned media is concentrated in an amount selected from the group of at least about 5 fold; at least about 10 fold; at least about 15 fold; at least about 20 fold; at least about 25 fold; at least about 30 fold; at least about 35 fold; at least about 40 fold; at least about 45 fold; at least about 50 fold; at least about 55 fold; at least about 60 fold; at least about 65 fold; at least about 70 fold; at least about 75 fold; at least about 80 fold; at least about 85 fold; or at least about 90 fold.

* * * * *